US007816529B2

(12) United States Patent
Wilson et al.

(10) Patent No.: US 7,816,529 B2
(45) Date of Patent: Oct. 19, 2010

(54) PYRIMIDINES USEFUL AS MODULATORS OF VOLTAGE-GATED ION CHANNELS

(75) Inventors: Dean Mitchell Wilson, San Diego, CA (US); Esther Martinborough, San Diego, CA (US); Timothy Donald Neubert, San Diego, CA (US); Andreas Peter Termin, Encinitas, CA (US); Jesus E. Gonzalez, III, San Diego, CA (US); Nicole Zimmerman, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1706 days.

(21) Appl. No.: 10/884,865

(22) Filed: Jul. 2, 2004

(65) Prior Publication Data

US 2005/0049247 A1    Mar. 3, 2005

Related U.S. Application Data

(60) Provisional application No. 60/484,362, filed on Jul. 2, 2003, provisional application No. 60/500,200, filed on Sep. 4, 2003.

(51) Int. Cl.
| | |
|---|---|
| *C07D 239/42* | (2006.01) |
| *C07D 401/04* | (2006.01) |
| *C07D 401/14* | (2006.01) |
| *C07D 403/04* | (2006.01) |
| *C07D 403/14* | (2006.01) |
| *C07D 401/06* | (2006.01) |
| *A61K 31/506* | (2006.01) |
| *A61P 19/02* | (2006.01) |

(52) U.S. Cl. .................................... 544/326; 514/256
(58) Field of Classification Search ................. 544/326; 514/256
See application file for complete search history.

(56) References Cited

U.S. PATENT DOCUMENTS

| 3,040,047 | A | 6/1962 | Sirakawa |
| 3,759,922 | A | 9/1973 | Kim et al. |
| 3,850,928 | A | 11/1974 | Kim et al. |
| 3,850,931 | A | 11/1974 | Kim et al. |
| 3,860,596 | A | 1/1975 | Kim et al. |
| 2002/0183335 | A1 | 12/2002 | Hewawasam et al. |

FOREIGN PATENT DOCUMENTS

| DE | 23 41 925 | 3/1975 |
| EP | 0 257 102 | 3/1988 |
| FR | 2263750 | 3/1974 |
| GB | 901749 | 7/1962 |
| GB | 1 512 101 | 5/1978 |
| JP | 51-100088 | 9/1976 |

| WO | WO 03/097615 | * 10/2003 |

OTHER PUBLICATIONS

Almeida et. al., Neurotherapeutics 4(1), 88-96, 2007.*
Ekberg et al.,, The International Journal of Biochemistry & Cell Biology, 38, 2005-2010, 2006.*
Markman et al, Journal of Pain, 7(15), 538-547, 2007.*
Kombov et al., Izvestiya Akademii Nauk, Seriya Khimicheskaya, 8, 1469-1474, 1994; CA 122: 160592, 1995.*
El-Bahaie et al., Pharmazie, 46(1), 26-28, 1991; CA 114: 228864, 1991.*
Machon et al., European Journal of Medicinal Chemistry, 19(4), 359-363, 1984; CA 102: 45867, 1985.*
Robev et al., Dokalady Bolgarskoi Akademii Nauk 31(5), 551-554, 1978; CA 90: 186887, 1979.*
Robev et al., Dokalady Bolgarskoi Akademii Nauk 31(9), 1131-1134, 1979; CA 90: 137763, 1979.*
Gupta et al., Journal of Heterocyclic Chemistry 12(6), 1311-1312, 1976; CA 84: 135585, 1976.*
Kosegi et al., JP 03112985; CA 115:159153, 1991(CAPLUS Abstract provided).*
Yoneda et al., Bulletin of Chemical Society of Japan, 46(12), 3849-3853; CA 80: 47947, 1974(CAPLUS Abstract provided).*
Santilli et al., Journal of Heterocyclic Chemistry, 9(2), 309-313, 1972; CA 77: 48423, 1972(CAPLUS Abstract provided).*
Kim et al., Chemistry & Industry (London, United Kingdom)(1969), (14), 458-9; CA 71:3347, 1969 (CAPLUS Abstract provided).*
Kampe, Angewandte Chemie (1982), 94(7), 543-4; CA 97: 109955, 1982 (CAPLUS Abstract provided).*
Juby et al. "4-Anilinopyrimidine-5-carboxylic Acids and Esters with Anti-Inflammatory and Analgetic Properties" J. Med. Chem., vol. 10, pp. 954-957, 1967.
Kim et al. "Reactions of 4-(2-Hydroxyethylamino)-2-phenyl-5-pyrimidinecarboxylic Acid with Acetic Anhydride. Syntheses of 8,9-Dihydro-6a-methyl-2-phenyl-5H,6aH-oxazolo-[2,3-b]pyrimido[4,5-d][1,3]oxazin-5-one and 8,9-Dihydro-8,8-dimethyl-2- phenyl-5H-oxazolo[2',3':6,1]pyrido[2,3-d]pyrimidin-5-one," J. Org. Chem. vol. 37 No. 18, pp. 2854-2857 (1972).
Kim et al. "Pyrimido[4,5-e][1,4]diazepin-5-ones and 4,4-Ethylenediaminobis(2-phenyl-pyrimidine-5-carboxylic acid) Diethyl Esters" J. Med. Chem., vol. 12, pp. 1121-1122,1969.
Koppel et al. "Pyrimidines. X. (Antibiotics. II) Synthesis of Bacimethrin, 2-Methoxy Analog of Thiamine, and Related Alkoxypyrimidines" J. Org. Chem., vol. 27, pp. 3614-3617, 1962.
Saad et al. "Functionalization and Heteroannelation of Ethyl 2-(4'-chlorophenyl)-4-mercapto-6-methylpyrimidine-5-caboxylate", Bull. Korean Chem. Soc., vol. 22, No. 3, pp. 311-314, 2001.
Hainsworth et al. "Effects of Extracellular pH on the Interaction of Sipatrigine and Lamotrigine with High-voltage-activated (HVA) Calcium Channels in Dissociated Neurones of Rat Cortex" Neuropharmacology, vol. 40, pp. 784-791, 2001.

(Continued)

*Primary Examiner*—Venkataraman Balasubramanian
(74) *Attorney, Agent, or Firm*—Wei-Chuan Chen

(57) ABSTRACT

The present invention relates to compounds useful as inhibitors of voltage-gated ion channels. The invention also provides pharmaceutically acceptable compositions comprising the compounds of the invention and methods of using the compositions in the treatment of various disorders.

22 Claims, No Drawings

OTHER PUBLICATIONS

Robert Forsyth et al. "The Tautomerism of Amidines. Part VI. Methylation of 4- Anilino—2-phenyl-6-methyl-pyrimidine." J.Chem. Soc. (2502-2510).

Dong Han Kim et al. "Ring Closure Reaction of 4-(2-Hydroxyanilino)-2-phenyl-5-pyrimidinecarboxylic Acid With Acetic Anhydride. Synthesis of Pyrimido[5,4-c] [1,5] benzoxazepin-5([]II)ones." J. Het. Chem. 1347-1354, vol. 9 (6).

Yoshifumi Maki et al. "The Double Smiles Rearrangement" Chem. Pharm. Bull. Tokyo pp. 607-609, vol. 20 (3) (1972).

J. S. Moffatt et al. "Contributions to the Chemistry of Synthetic Antimalarials. Part IX. Some Pyrimidine Derivatives." J. Chem. Soc. (1950) pp. 1603-1606.

Fumio Yoneda et al. "Syntheses of 2-Deoxo-2-phenyl-5-deazaflavins and 3-Phenyl-5-deazaflavins and Their Use in the Oxidation of Benzyl Alcohol and Benzylamine." Chem Pharm. Bull. (Tokyo) (1980) pp. 3514-3520, vol. 28 (12).

Shojiro Yurugi et al. "Studies on the Syntheses of N-Heterocyclic Compounds. II. Pyrimido [4,5-e]-, and Pyrido-[4,3-e]-1,2,3,5-tetrahydro [1,4]oxazepine-5-one." Chem. Pharm. Bull. (Tokyo) (1971) pp. 2354-2364, vol. 19 (11).

Moorthy S. S. Palanki et al. "Novel Inhibitors of AP-1 and NF-kB Mediated Gene Expression: Structure-Activity Relationship Studies of Ethyl 4-[(3-Methyl-2,5-Dioxo(3-pyrrolinyl))amino-2-(trifluoromethyl)pyrimidine-5-carboxylate" Bioorganic & Medicinal Chemistry Letters (2000) pp. 1645-1648, vol. 10.

H.L. Wheeler, "LX.-Research on the Cycloamidines: Pyrimidine Derivatives." American Chemical Journal (1898) pp. 481-490, vol. XX.

Narinder D. Venayak et al. "Enamidines. Part 3. Synthesis of 4-Aminopyrimidine Derivatives from N1-Alkenyl-N2-(alkylcarbamoyl)benzamidines." J. Chem Research (S). (1983) pp. 200-201.

* cited by examiner

PYRIMIDINES USEFUL AS MODULATORS OF VOLTAGE-GATED ION CHANNELS

CROSS-REFERENCE TO RELATED APPLICATIONS

The present application claims the benefit under 35 U.S.C. §119 to U.S. Provisional application No. 60/484,362, filed Jul. 2, 2003, entitled "PYRIMIDINES USEFUL AS INHIBITORS OF VOLTAGE-GATED SODIUM CHANNELS," and U.S. Provisional application No. 60/500,200, filed Sep. 4, 2003, entitled "PYRIMIDINES USEFUL AS INHIBITORS OF VOLTAGE-GATED SODIUM CHANNELS," the entire disclosures of each being incorporated herein by reference.

TECHNICAL FIELD OF THE INVENTION

The present invention relates to compounds useful as inhibitors of voltage-gated sodium channels and calcium channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

Table 1 (Abbreviations: CNS=central nervous system, PNS=peripheral nervous sytem, DRG=dorsal root ganglion, TG=Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µm | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TrX, lidocaine (See, Mao, J. and L. L. Chen (2000) "Systemic lidocaine for neuropathic pain relief" *Pain* 87(1): 7-17.) bupivacaine, phenytoin (See Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See Goldin, A. L. (2001) "Resurgence of sodium channel research" *Annu Rev Physiol* 63: 871-94.). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (ee, Akopian, A. N., V. Souslova, et al. (1999) "The tetrodotoxin-resistant sodium channel SNS has a specialized function in pain pathways" *Nat Neurosci* 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33.). It has a slow rate of inactivation and left-shifted voltage dependence for activation (ee Dib-Hajj, S., J. A. Black, et al. (2002) "NaN/Nav1.9: a sodium channel with unique properties" *Trends Neurosci* 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir (Wien)* 144(8): 803-10; discussion 810.). NaV1.6 and NaV1.7 are also expressed in dorsal root ganglion neurons and contribute to the small TTX sensitive component seen in these cells. NaV1.7 in particular my therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See. Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201)

Calcium channels are membrane-spanning, multi-subunit proteins that allow Ca entry from the external milieu and concurrent depolarization of the cell's membrane potential. Traditionally calcium channels have been classified based on their functional characteristics such as low voltage or high voltage activated and their kinetics (L, T, N, P, Q). The ability to clone and express the calcium channel subunits has lead to an increased understanding of the channel composition that produces these functional responses. There are three primary subunit types that make up calcium channels—$\alpha 1$, $\alpha 2\delta$, and $\beta$. The $\alpha 1$ is the subunit containing the channel pore and voltage sensor, $\alpha 2$ is primarily extracellular and is disulfide linked to the transmembrane $\delta$ subunit, $\beta$ is nonglycosylated subunit found bound to the cytoplasmic region of the $\alpha 1$ subunit of the Ca channel. Currently the various calcium channel subtypes are believed to made up of the following specific subunits:

L-type, comprising subunits $\alpha_{1C}\alpha_{1D}\alpha_{1F}$, or $\alpha_{1S}$, $\alpha 2\delta$ and $\beta_{3a}$ N-Type, comprising subunits $\alpha_{1B}$, $\alpha 2\delta$, $\beta_{1b}$ P-Type, comprising subunits $\alpha_{1A}$, $\alpha 2\delta$, $\beta_{4a}$ Q-Type, comprising subunits $\alpha_{1A}$ (splice variant) $\alpha 2\delta$, $\beta_{4a}$ R-Type, comprising subunits $\alpha_{1E}$, $\alpha 2\delta$, $\beta_{1b}$ T-Type, comprising subunits $\alpha_{1G}$, $\alpha_{1H}$, or $\alpha_{1I}$ Calcium channels play a central role in neurotransmitter release. Ca influx into the presynaptic terminal of a nerve process binds to and produces a cascade of protein-protein interactions (syntaxin 1A, SNAP-25 and synaptotagmin) that ultimately ends with the fusion of a synaptic vesical and release of the neurotransmitter packet. Blockade of the presynaptic calcium channels reduces the influx of Ca and produces a cubic $X^3$ decrease in neurotransmitter release.

The N type Ca channel (CaV2.2) is highly expressed at the presynaptic nerve terminals of the dorsal root ganglion as it forms a synapse with the dorsal horn neurons in lamina I and II. These neurons in turn have large numbers of N type Ca channels at their presynaptic terminals as they synapse onto second and third order neurons. This pathway is very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other hand may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

The N type Ca channel has been validated in man by intrathecal infusion of the toxin Ziconotide for the treatment of intractable pain, cancer pain, opioid resistant pain, and neuropathic and severe pain. The toxin has an 85% success rate for the treatment of pain in humans with a greater potency than morphine. An orally available N type Ca channel antagonist would garner a much larger share of the pain market. Ziconotide causes mast cell degranulation and produces dose-dependent central side effects. These include dizziness, nystagmus, agitation, and dysmetria. There is also orthostatic hypotension in some patients at high doses. The primary risk for this target involves the CNS side-effects seen with Ziconotide at high dosing. These include dizziness, nystagmus, agitation, and dysmetria. There is also orthostatic hypotension in some patients at high doses. It is believed that this may be due to Ziconotide induced mast cell degranulation and/or its effects on the sympathetic ganglion that like the dorsal root ganglion also expresses the N type Ca channel. Use-dependent compounds that block preferentially in the higher frequency range>10 Hz should be helpful in minimizing these potential side-effect issues. The firing rate in man of the sympathetic efferents is in the 0.3 Hz range. CNS neurons can fire at high frequencies but generally only do so in short bursts of action potentials. Even with the selectivity imparted by use-dependence intrinsic selectivity against the L type calcium channel is still necessary as it is involved in cardiac and vascular smooth muscle contraction.

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, and Ca channel antagonists preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

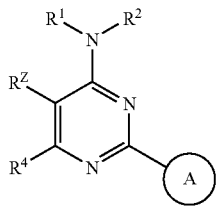

I or a pharmaceutically acceptable derivative thereof, wherein $R^1$, $R^2$, $R^z$, $R^4$, and ring A are as defined herein.

These compounds and pharmaceutically acceptable compositions are useful for treating or lessening the severity of a variety of diseases, disorders, or conditions, including, but not limited to, acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, and incontinence.

DETAILED DESCRIPTION OF THE INVENTION

I. General Description of Compounds of the Invention:

The present invention relates to compounds of formula I useful as inhibitors of voltage-gated sodium channels:

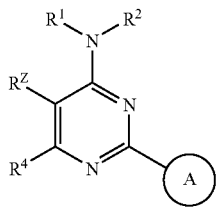

I or a pharmaceutically acceptable salt thereof, wherein:
$R^Z$ is —C(O)$R^3$, —C(O)O$R^3$, or $R^{Z1}$;
$R^{Z1}$ is —C(O)N(R')$_2$, —SO$_2$R', —SO$_2$NHR', —NHSO$_2$R', —P(O)(OR')$_2$, —C(O)N(CN)R', an optionally substituted 5-membered heteroaryl ring having 1-4 heteroatoms selected from O, S, or N, or an optionally substituted pyran-4-one-yl;

$R^1$ and $R^2$ are each independently hydrogen, or an optionally substituted group selected from $C_{1-6}$aliphatic, a 5-6 membered aryl ring having 0-5 heteroatoms independently selected from nitrogen, oxygen, or sulfur, or a 3-7-membered saturated or partially unsaturated ring having 0-3 heteroatoms independently selected from nitrogen, oxygen, or sulfur; or $R^1$ and $R^2$, taken together with the nitrogen atom to which they are bound, form an optionally substituted 3-8 membered heterocyclyl or heteroaryl ring having 1-3 heteroatoms independently selected from nitrogen, oxygen, or sulfur, wherein $R^1$, $R^2$, or any ring formed by $R^1$ and $R^2$ taken together, are each independently optionally substituted at one or more carbon atoms with 0-4 occurrences of —$R^5$, and at one or more substitutable nitrogen atoms with —$R^6$;

ring A is a 5-6 membered aryl ring or 8-10 membered bicyclic aryl ring, having 0-5 heteroatoms independently selected from nitrogen, oxygen, or sulfur, or a 3-7-membered saturated or partially unsaturated ring having 0-3 heteroatoms independently selected from nitrogen, oxygen, or sulfur, optionally substituted at one or more carbon atoms with 0-5 occurrences of —$R^7$, and at one or more substitutable nitrogen atoms with —$R^8$;

each occurrence of $R^3$, $R^4$, $R^5$, and $R^7$ is independently Q-$R^X$; wherein Q is a bond or is a $C_1$-$C_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of $R^X$ is independently selected from R', halogen, NO$_2$, or CN, provided that when $R^Z$ is —OR$^3$, then Q-$R^X$ is bonded to the oxygen atom through a carbon atom;

wherein each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur; and each occurrence of $R^6$ or $R^8$ is independently R', —COR', —CO$_2$(C$_{1-6}$ aliphatic), —CON(R')$_2$, or —SO$_2$R', provided that when $R^Z$ is $R^3$, then $R^3$ is bonded to the carbon atom of the carbonyl group through an atom other than oxygen, preferably, through a carbon atom.

In certain other embodiments$_{[KG1]}$, for compounds of the invention wherein $R^Z$ is —$R^3$ as described generally above and herein:

a) when ring A is unsubstituted phenyl, $R^3$ is methyl, and $R^4$ is =S or —SMe, then $R^1$ and $R^2$ taken together cannot be N-morpholino, N-pyrrolidinyl, or optionally substituted piperazinyl;

b) when ring A is N-morpholino, $R^3$ is H, and $R^4$ is Cl or Me, then $R^1$ is not Et, when $R^2$ is 4-Cl-phenyl, or $R^1$ and $R^2$, taken together, cannot be N-morpholino;

c) when ring A is N-pyrrolidinyl and $R^3$ is H, then:
i) when $R^4$ is —N(CH$_3$)COPh, then $R^1$ and $R^2$, taken together, cannot be pyrrolidinyl; and
ii) when $R^4$ is Cl, then $R^1$ is not Et, when $R^2$ is 4-Me-phenyl;

d) when ring A is N-piperidinyl, $R^3$ is hydrogen, and $R^4$ is methyl, then $R^1$ and $R^2$, taken together, cannot be N-piperidinyl;

e) when ring A is optionally substituted piperazinyl, $R^3$ is hydrogen, and $R^4$ is chloro, then when $R^1$ is Et, then $R^2$ is not 4-Cl-phenyl, 4-Me-phenyl, or 4-F-phenyl, or $R^1$ and $R^2$, taken together, cannot be thiomorpholino;

f) when ring A is 2,5-dimethyl-1H-pyrrol-1-yl, $R^3$ is hydrogen, and $R^4$ is OMe, then when $R^1$ is Me, then $R^2$ is not benzyl;

g) when ring A is 1-oxido-4-thiomorpholinyl, $R^3$ is hydrogen, and $R^4$ is OEt, then $R^1$ and $R^2$, taken together, cannot be piperizinyl;

h) when $R^3$ is $CH_3$ or optionally substituted phenyl $R^1$ is hydrogen, $R^2$ is optionally substituted phenyl, methyl, ethyl, COR', NR', or CONHR', and $R^4$ is =S, Me, SMe, or $SCH_2CO_2Me$, $SCH_2CN$, then ring A is not unsubstituted phenyl or 4-Cl-phenyl;

i) when $R^3$ is $CH_3$, $R^1$ is hydrogen, $R^2$ is ethyl, and $R^4$ is hydrogen, then ring A is not N-pyrrolidinyl, piperazin-1-yl, N-morpholinyl, or 1-piperidinyl;

j) when $R^3$ is $N(R')_2$, $R^1$ is hydrogen, $R^2$ is 3-,5-Cl-phenyl, 4-Cl-phenyl, methyl, optionally substituted cyclohexyl, 3-Cl, 4-OMe-benzyl, 4-Ac-phenyl, ethyl, i-propyl, 4-OEt-phenyl, 4-OMe-phenyl, benzyl, or $(CH_2)_2OR$, and $R^4$ is $CH_3$, hydrogen, or SMe, then ring A is not unsubstituted phenyl, piperidinyl, optionally substituted piperazinyl, morpholinyl, optionally substituted pyrrolidinyl, 5,8-dihydro-1,7-naphthyridin-7(6H)-yl, or 5,6-dihydro-8-imidazo[1,2-a]pyrazin-7-yl;

k) when $R^3$ is —CH=CHN$(CH_3)_2$, $CH_3$, —$(CH_2)_2$—N-morpholino, —$(CH_2)_2$—OMe, —$(CH_2)_2$—OH, —$CH_2$OMe, n-butyl, pyridin-2-ylmethyl, pyridin-2-yl, pyrimidin-5-yl, $CH_2SO_2$Me, —$(CH_2)_2$—NMe$_2$, —$(CH_2)_2$—N-(4-methylpiperazyl), —$(CH_2)_2$—NH-pyridin-3-yl, —$(CH_2)_2$—NH—$CH_2$-pyridin-3-yl, 1-methyl-1H-imidazol-2-yl, 5-amino-1,2-dimethyl-1H-imidazol-4-yl, 4-(dimethylamino)phenyl, 3,4-(methylenedioxy)phenyl, —$CH_2$=$CH_2$, —CH=$CH_2$, or —CH(CN)COOEt, $R^1$ is hydrogen, $R^2$ is optionally substituted benzyl or ethyl, $R^4$ is SMe or hydrogen, then ring A is not unsubstituted phenyl or optionally substituted pyrrolidinyl;

l) when $R^1$ is hydrogen and $R^2$ is hydrogen or 4,6-dimethylpyrimidin-2-yl, ring A is optionally substituted phenyl, $R^3$ is Me or unsubstituted phenyl, then $R^4$ is not SMe, =S, Me, or unsubstituted phenyl;

m) when $R^1$ is hydrogen and $R^2$ is optionally substituted benzyl, then $R^3$ is not 3,4,5-trimethoxyphenyl;

n) when $R^1$ and $R^2$ are both hydrogen, ring A is (2-fluorophenylmethyl)-1H-pyrazolo[3,4-b]pyridin-3-yl, $R^3$ is ethyl or 2-ethoxyethyl, then $R^4$ is not hydrogen;

o) when $R^1$ is hydrogen, $R^2$ is benzoyl, then $R^3$, $R^4$, and ring A are all not simultaneously unsubstituted phenyl;

p) when $R^1$ and $R^2$ are both hydrogen, ring A is 4-(4'-morpholinyl)-5-methyl-2-phenylthieno[2,3-d]pyrimidin-6-yl, 4-amino-5-methyl-2-phenylthieno[2,3-d]pyrimidin-6-yl, 4-(4-(4-fluorophenyl)-piperazyl)-5-methyl-2-phenylthieno[2,3-d]pyrimidin-6-yl, 4-(4,6-dimethyl-pyrimidin-2-yl)amino-5-methyl-2-phenylthieno[2,3-d]pyrimidin-6-yl, 4-(N-pyrrolidinyl)-5-methyl-2-phenylthieno[2,3-d]pyrimidin-6-yl, or unsubstituted phenyl, $R^3$ is methyl, then $R^4$ is not methyl or SMe;

q) when $R^1$ and $R^2$ both are hydrogen, $R^3$ is methyl, $R^4$ is =S or unsubstituted phenyl, then ring A is not unsubstituted phenyl; and r) when $R^1$ and $R^2$ taken together form a N-pyrrolidinyl ring, $R^3$ is —NHCH$_2$(4-trifluoromethylphenyl), $R^4$ is H, then ring A is not N-pyrrolidinyl, 3,4-dimethoxyphenyl, 2-methoxyphenyl, thiophen-3-yl, or thiophen-2-yl.

For certain other embodiments$_{[KG2]}$, when $R^Z$ in compound of formula I is $C(O)N(R')_2$, then:

a) when $R^1$ and $R^2$ are both hydrogen, then $N(R')_2$ is not $NH_2$ or NH—C(=NH)NH$_2$;

b) when $R^1$ is hydrogen, methyl, or ethyl, and $R^2$ is —$(CH_2)_2$—OH, —$(CH_2)_2$—OAc, 3,5-dichlorophenyl, or benzyl, $R^4$ is hydrogen or methyl, ring A is unsubstituted phenyl, then $N(R')_2$ is not NH$_2$, NHNH$_2$, NHMe, NH$(CH_2)_2$—OH, or NH-benzyl;

c) when $R^1$ is hydrogen and $R^2$ is methyl, $R^4$ is OH, ring A is unsubstituted phenyl, then $N(R')_2$ is not NHMe;

d) when ring A is optionally substituted phenyl, $R^1$ is hydrogen and $R^2$ is optionally substituted phenyl, $R^4$ is optionally substituted phenyl or unsubstituted naphthyl, then $N(R')_2$ is not NH$_2$;

e) when $R^1$ and $R^2$ are both hydrogen, $N(R')_2$ is NH$_2$, NH-(optionally substituted phenyl), N(optionally substituted C1-6 aliphatic)(optionally substituted phenyl), or NH(6,7,8,9-tetrahydro-5H-benzocyclohepten-6-yl), $R^4$ is hydrogen, then ring A is not 1-imidazolyl, 1-piperidyl, unsubstituted phenyl, optionally substituted 2-oxo-imidazolidin-1-yl or 1-[(2-fluorophenyl)methyl]-1H-indazol-3-yl;

f) when $R^1$ is hydrogen, $R^2$ is optionally substituted phenyl, ring A is unsubstituted phenyl, R4 is methyl or hydrogen, then $N(R')_2$ is not NHEt, N(Et)$_2$, NH(optionally substituted phenyl), g) when $R^1$ is hydrogen, $R^2$ is 2-pyridinyl, ring A is unsubstituted phenyl, $R^4$ is hydrogen, then $N(R')_2$ is not N-morpholinyl;

h) when $R^1$ is hydrogen, $R^2$ is hydrogen or $C_{1-4}$ aliphatic, $N(R')_2$ is NH(C1-4 aliphatic) or N(C1-4 aliphatic)$_2$, $R^4$ is hydrogen, then ring A is not N-piperidyl or optionally substituted N-piperazyl;

i) when $R^1$ is hydrogen, $R^2$ is 4-chlorophenyl, ring A is unsubstituted phenyl, $R^4$ is methyl, then $N(R')_2$ is not NHCH2-furan-2-yl;

j) ring A is not 2-formyl-pyrrolin-1-yl, optionally substituted hydroxymethyl-pyrrolidin-1-yl, hydroxypiperidinyl, or hydroxymethylpiperidinyl;

k) the following compounds are excluded:

| $R^1$ | $R^2$ | $N(R')_2$ | $R^4$ | Ring A |
|---|---|---|---|---|
| H | Optionally substituted cyclohexyl | N-morpholinyl | H | phenyl |
| H | Optionally substituted cyclohexyl | N-morpholinyl | H | N-pyrrolidinyl |
| H | Optionally substituted cyclohexyl | N-morpholinyl | H | phenyl |

-continued

| $R^1$ | $R^2$ | $N(R')_2$ | $R^4$ | Ring A |
|---|---|---|---|---|
| H | Optionally substituted cyclohexyl or benzyl | NMe$_2$ or NH(optionally substituted cyclohexyl) | H | N-morpholino |
| H | H | NH(6,7,8,9-tetrahydro-5H-benzocyclohepten-6-yl | H | pyridinyl |
| H | 4-nitrophenyl | 4-methylpiperazyl | methyl | phenyl |
| Methyl | methyl | NH-tetrazolyl | H | phenyl |
| H | optionally substituted cyclohexyl or benzyl | NH(Optionally substituted benzyl or cyclohexyl) | H | optionally substituted N-piperazyl or imidazol-1-yl or 2-hydroxypyrrolyl |
| H | optionally substituted benzyl | NH(optionally substituted cyclohexyl) | H | optionally substituted 2,3-dihydro-1H-isoindol-2-yl |
| H | optionally substituted benzyl | NH-pyridylmethyl | H | 2,3-dihydro-1H-isoindol-2-yl |
| H | optionally substituted benzyl | NHpyridylmethyl or NHCH$_2$CH$_2$—N-morpholino | H | 2-aminocarbonyl-prrolidin-1-yl or N-morpholino or 1H-imidazo[4,5-c]pyridine-(6-CO$_2$Me)-4,5,6,7-tetrahydro-1-yl or 1,2,3,4,6,7-hexahydro-3-oxo-5H-pyrazolo[4,3-c]pyridin-5-yl |
| H | (aryl or heteroaryl) substituted Cl-4 aliphatic | | H | 3,4-dihydro-(1H)-isoquinolin-2-yl or 5,6-dihydroimidazo[1,2-a]pyrazin-7(8H)-yl or 5,8-dihydro-1,7-napthyridin-7(6H)-yl or 5,7-dihydro-6H-pyrrolo[3,4-b]pyridin-6-yl or 2,3-dihydro-1H-indol-1-yl or 4,5,6,7-tetrahydro-isoxazolo[4,5-c]pyridin-5-yl or 6,7-dihydrothiazolo[5,4-c]pyridin-(4H)-5-yl |
| H | Optionally substituted benzyl | NH-pyridin-2-ylmethyl | H | 1-piperidinyl | l) when $R^1$ is H or optionally substituted $C_{1-4}$ aliphatic, $R^2$ is optionally substituted benzyl, $R^4$ is methoxy, then ring A is not optionally substituted N-piperazyl, 3,4-dihydro-(1H)-isoquinolin-2-yl, 5,6-dihydroimidazo[1,2-a]pyrazin-7(8H)-yl, or 6,7-dihydrothieno[3,2-c]pyridin-5(4H)-2-yl;

m) when $R^1$ and $R^2$ are both methyl, $R^4$ is hydrogen, ring A is 4-[(napth-2-yl)sulfonyl]piperazyl, then $N(R')_2$ is not NHOH or NH—O-(tetrahydro-2H-pyran-2-yl);

n) when $R^1$ is hydrogen, $R^2$ is optionally substituted benzyl, $R^4$ is hydrogen, $N(R')_2$ is NHCH$_2$(pyridin-2-yl), then ring A is not 3-(hydroxymethyl)2(1H)-isoquinolinyl; and o) when $R^1$ is hydrogen, $R^2$ is (aryl or heteroaryl) substituted $C_{1-4}$ aliphatic, $R^4$ is hydrogen, then ring A is not 3,4-dihydro-(1H)-isoquinolin-2-yl, 5,6-dihydroimidazo[1,2-a]pyrazin-7(8H)-yl, 5,8-dihydro-1,7-napthyridin-7(6H)-yl, 5,7-dihydro-6H-pyrrolo[3,4-b]pyridin-6-yl, 2,3-dihydro-1H-indol-1-yl, 4,5,6,7-tetrahydro-isoxazolo[4,5-c]pyridin-5-yl, or 6,7-dihydrothiazolo[5,4-c]pyridin-(4H)-5-yl; and o) when $R^1$ and $R^2$ taken together is 4-(2-naphthalenylsulfonyl)-1-piperazinyl, ring A is 4-(2-naphthalenylsulfonyl)-1-piperazinyl or 4-(2-naphthalenylsulfonyl)amino-piperidinyl and $R^4$ is hydrogen, then $R^3$ is not NH—O-(tetrahydro-2H-pyran-2-yl) or NHOH.

In certain other embodiments, when $R^Z$ is $R^{Z1}$ as generally described above and herein:

a) when $R^{Z1}$ is tetrazolyl, $R^1$ is hydrogen, $R^2$ is hydrogen or optionally substituted phenyl, $R^4$ is hydrogen, then ring A is not unsubstituted 1-pyrrolidinyl, 1-piperidyl, N-morpholinyl, 1-azepanyl, or phenyl.

In certain other embodiments, when $R^Z$ is $R^{Z1}$ as described above and herein:

a) when $R^{Z1}$ is —P(O)(OR')$_2$ and R' is $C_{1-4}$ aliphatic, $R^1$ and $R^2$ are both hydrogen, and $R^4$ is hydrogen, methyl, anino, —OCH$_2$OH, then ring A is not 1-[(2-fluorophenyl)methyl]-1H-pyrazolo[3,4-b]pyridin-3-yl or unsubstituted phenyl.

In certain other embodiments, when $R^Z$ is $R^{Z1}$ as generally described above and herein:

a) when $R^{Z1}$ is —SO$_2$NHR' and R' is hydrogen, $R^1$ and $R^2$ are both hydrogen, $R^4$ is amino, then ring A is not N-morpholino.

In certain other embodiments$_{[KG3]}$, for compounds of the invention wherein $R^Z$ is —OR$^3$ as described generally above and herein:

a) when $R^3$ is ethyl; $R^4$ is hydrogen; ring A is unsubstituted phenyl, and $R^1$ is hydrogen, then $R^2$ is not optionally substituted 2-pyridinyl, optionally substituted phenyl, optionally substituted benzyl, —CH$_2$CO$_2$H, —CH$_2$CN, n-propyl, methyl, ethyl, —CH$_2$(4-OMe-phenyl), —CH$_2$CON(Me)CH$_2$Ph, —CH$_2$C≡CH, —CH$_2$CH$_2$OMe, —CH$_2$CH═CH$_2$, or —(CH$_2$)$_3$OH;

b) when $R^3$ is ethyl; $R^4$ is hydrogen; ring A is thienyl; and $R^1$ is hydrogen; then $R^2$ is not optionally substituted phenyl;

c) when $R^3$ is ethyl; $R^4$ is hydrogen; ring A is unsubstituted phenyl; then when $R^1$ is methyl, ethyl, CH$_2$CH$_2$Ph, —CH$_2$CH$_2$morpholino, —CH$_2$CH$_2$NEt$_2$, —CH$_2$CH$_2$OMe, n-butyl, or optionally substituted phenyl, then $R^2$ is not —CH$_2$CH$_2$CN, —CH$_2$CN, or —CH$_2$CH$_2$OAc, or $R^1$ and $R^2$ taken together are not optionally substituted piperidinyl, morpholino, or thiomorpholino;

d) when $R^3$ is ethyl; $R^4$ is NH$_2$, Cl, Me, or Br, ring A is unsubstituted phenyl or morpholino, and $R^1$ is hydrogen, then $R^2$ is not optionally substituted phenyl, or COR';

e) when $R^3$ is ethyl, $R^4$ is hydrogen; and ring A is unsubstituted phenyl, then $R^1$ and $R^2$ are not simultaneously methyl;

f) when $R^3$ is methyl, then ring A, $R^4$, and $R^1$ and $R^2$ taken together, are not simultaneously piperidinyl;

g) when $R^3$ is ethyl, $R^1$ is hydrogen, $R^2$ is unsubstituted phenyl, and $R^4$ is methyl or thiomorpholino, then ring A is not unsubstituted phenyl, 4-OMe-phenyl, 2-pyridinyl, 4-Cl-phenyl, 2-Cl-phenyl, 3,4-dichlorophenyl, 4-Me-phenyl, 3,5-dichlorophenyl, 4-OH-phenyl, or 3CF$_3$—, 4-Cl-phenyl;

h) when $R^3$ is ethyl, methyl, or isopropyl, $R^1$ is hydrogen or ethyl, and $R^2$ is ethyl, COCH$_3$, isopropyl, —CH$_2$CH$_2$CN, benzyl, —CH$_2$CH$_2$NEt$_2$, —CH$_2$CH$_2$COOEt, or $R^1$ and $R^2$, taken together are piperazinyl, and $R^4$ is hydrogen, then ring A is not optionally substituted piperazinyl, pyrrolidinyl, morpholino, or piperidinyl;

i) when $R^3$ is ethyl, and $R^1$ is hydrogen, then $R^2$ is not optionally substituted cyclohexyl;

j) when $R^3$ is methyl, and $R^4$ is N(Me)COPh, then ring A and $R^1$ and $R^2$, taken together, are not simultaneously N-pyrrolidinyl;

k) when $R^3$ is ethyl, $R^4$ is optionally substituted phenyl, ring A is optionally substituted phenyl, and $R^1$ is hydrogen, then $R^2$ is not optionally substituted naphthyl, methyl, optionally substituted phenyl, or $R^1$ and $R^2$, taken together are not morpholino;

l) when $R^3$ is ethyl, then when one of $R^1$ and $R^2$, taken together or ring A is optionally substituted piperazinyl, then the other of $R^1$ and $R^2$, taken together or ring A is not thiomorpholino or morpholino;

m) $R^1$ and $R^2$, taken together and ring A are not simultaneously morpholino or thiomorpholino;

o) when $R^3$ is methyl, $R^4$ is hydrogen or OMe, ring A is unsubstituted phenyl, and $R^1$ is hydrogen, then $R^2$ is not methyl, 2,3-dimethylphenyl, or 3-CF$_3$phenyl;

p) when $R^3$ is ethyl, $R^4$ is hydrogen, and ring A is unsubstituted phenyl, then:
  i) $R^1$ and $R^2$ taken together do not form a 1-pyrrolidinyl, 4-methylpiperazinyl, or 1-piperidyl;
  ii) $R^1$ and $R^2$ both are not hydrogen, methyl, or ethyl;
  iii) when $R^1$ is hydrogen then $R^2$ is not 2-hydroxyethyl.

In still other embodiments, for compounds of the invention wherein $R^Z$ is —C(O)R$^3$, as described generally above and in subsets herein, $R^3$ is bonded to the carbon atom of the carbonyl group through an atom other than oxygen or nitrogen.

In yet other embodiments, for compounds of the invention wherein $R^Z$ is —C(O)R$^3$, as described generally above and in subsets herein, for $R^4$, Q is not O or S, when $R^X$ is optionally substituted furyl, or thiophene.

In still other embodiments, for compounds of the invention wherein $R^Z$ is —C(O)R$^3$, as described generally above and in subsets herein, when $R^1$ is hydrogen, $R^2$ is a group other than NR'.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(O)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(O)N(R°)$_2$; —OC(O)N(R°)$_2$; —S(O)$_2$R°; —SO$_2$N(R°)$_2$; —S(O)R°; —NR°SO$_2$N(R°)$_2$; —NR°SO$_2$R°; —C(=S)N(R°)$_2$; —C(=NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R⁺, —N(R⁺)$_2$, —C(O)R⁺, —CO$_2$R⁺, —C(O)C(O)R⁺, —C(O)CH$_2$C(O)R⁺, —SO$_2$R⁺, —SO$_2$N(R⁺)$_2$, —C(=S)N(R⁺)$_2$, —C(=NH)—N(R⁺)$_2$, or —NR⁺SO$_2$R⁺; wherein R⁺ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R⁺ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R³⁰, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R³⁰, or any other variable similarly defined herein) that are bound to different atoms and are taken together with both of those atoms to form a ring, for example where a phenyl group is substituted with two occurrences of OR°

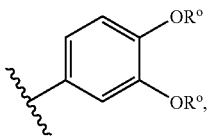

these two occurrences of $R^o$ are taken together with the oxygen atoms to which they are bound to form a fused 6-membered oxygen containing ring:

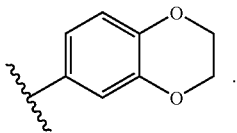

It will be appreciated that a variety of other rings can be formed when two independent occurrences of $R^o$ (or $R^{30}$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

In certain embodiments of the present invention, R' is hydrogen.

In certain embodiments of the present invention, R' is independently selected from an optionally substituted group selected from $C_{1-8}$ aliphatic, $C_{6-10}$ aryl, a heteroaryl ring having 5-10 ring atoms, or a heterocyclyl ring having 3-10 ring atoms.

In certain embodiments of the present invention, R' is an optionally substituted $C_{1-8}$ aliphatic group. In certain such embodiments, R' is $C_{1-4}$ aliphatic group optionally substituted with halo, OH, COOH, CN, —$OC_{1-4}$alkyl. Or, R' is $C_{1-4}$ aliphatic group optionally substituted with a 5-6 membered heterocyclic ring containing optional substituents. Examples of such heterocyclic ring includes, e.g., tetrahydrofuranyl, pyranyl, piperidinyl, and piperazinyl. Or, R' is $C_{1-4}$ aliphatic group optionally substituted with an aryl group containing optional substituents.

In other embodiments of the present invention, R' is an optionally substituted $C_{6-10}$ aryl group. Suitable aryl groups include phenyl and napthyl.

In certain other embodiments of the compounds of the present invention, R' is an optionally substituted heteroaryl ring having 5-10 ring atoms. Suitable heteroaryl rings include 5-membered heteroaryl rings such as, e.g., pyrrolyl, thienyl, and thiazolyl.

Or, R' is an optionally substituted heterocyclyl ring having 3-10 ring atoms. Such rings include, e.g., tetrahydrofuranyl, pyranyl, piperidinyl, and piperazinyl.

In other embodiments of the present invention, two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur. In certain embodiments, two occurrences of R' taken together with the atom(s) to which they are bound, form a 5-8 membered cycloalkyl ring. In certain other embodiments, two occurrences of R' taken together with the atom(s) to which they are bound, form a 5-8 membered heterocyclyl ring. In certain other embodiments, two occurrences of R' taken together with the atom(s) to which they are bound, form a 5-8 membered heterocyclyl ring having 0-3 heteroatoms independently selected from nitrogen, oxygen, or sulfur. In certain other embodiments, two occurrences of R' taken together with the atom(s) to which they are bound, form an aryl ring or they form a 5-8 membered having 0-3 heteroatoms independently selected from nitrogen, oxygen, or sulfur.

In some embodiments of the present invention, $R^1$ and $R^2$ are each independently hydrogen, or an optionally substituted group selected from $C_{1-6}$aliphatic, a 5-6 membered aryl ring having 0-5 heteroatoms independently selected from nitrogen, oxygen, or sulfur, or a 3-7-membered saturated or partially unsaturated ring having 0-3 heteroatoms independently selected from nitrogen, oxygen, or sulfur; or $R^1$ and $R^2$, taken together with the nitrogen atom to which they are bound, form an optionally substituted 3-8 membered heterocyclyl or heteroaryl ring having 1-3 heteroatoms independently selected from nitrogen, oxygen, or sulfur, wherein $R^1$, $R^2$, or any ring formed by $R^1$ and $R^2$ taken together, are each independently optionally substituted at one or more carbon atoms with 0-4 occurrences of —$R^5$, and at one or more substitutable nitrogen atoms with —$R^6$.

In certain embodiments of the present invention, neither $R^1$ nor $R^2$ is hydrogen. Or, $R^1$ and $R^2$ are each independently an optionally substituted $C_{1-6}$aliphatic group.

In certain other embodiments of the present invention, neither $R^1$ nor $R^2$ is hydrogen, and $R^1$ and $R^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2(NR)$, or $(NR)SO_2$.

In other embodiments of the present invention, both $R^1$ and $R^2$ are an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2(NR)$, or $(NR)SO_2$. In yet other preferred embodiments, one of $R^1$ and $R^2$ is an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2(NR)$, or $(NR)SO_2$. Preferred $R^1$ and $R^2$ groups are optionally substituted methyl, ethyl, cyclopropyl, n-propyl, propenyl, cyclobutyl, (CO)$OCH_2CH_3$, $(CH_2)_2OCH_3$, $CH_2(CO)OCH_2CH_3$, $CH_2(CO)$ OCH$_3$, CH(CH$_3$)CH$_2$CH$_3$, or t-butyl, or n-butyl. More preferred R$^1$ and R$^2$ groups include those shown below in Table 2.

In other embodiments of the present invention, R$^1$ and R$^2$ are both C$_{1-4}$ aliphatic or R$^1$ and R$^2$ taken together form a 5-6 membered heterocyclic ring. Preferred R$^1$ and R$^2$ include methyl, ethyl, or propyl; or R$^1$ and R$^2$, taken together form an optionally substiuted 1-pyrrolidinyl or 1-piperidinyl. In another embodiment, R$^1$ and R$^2$ both are simultaneously methyl or ethyl.

In other embodiments of the compounds of the present invention, R$^1$ and R$^2$ are both C$_{1-4}$ alphatic or R$^1$ and R$^2$ taken together form a 3-6 membered heterocyclic ring having up to 2 heteroatoms. Preferred R$^1$ and R$^2$ include methyl, ethyl, propyl; or R$^1$ and R$^2$, taken together form an optionally substituted 1-azetidinyl, 1-pyrrolidinyl, 1-piperidinyl, or 1-piperazinyl.: In one embodiment, R$^1$ and R$^2$ both are methyl or ethyl, or R$^1$ and R$^2$, taken together form a 1-pyrrolidinyl ring. In one embodiment, R$^1$ and R$^2$ both simultaneously are methyl or ethyl.

In other embodiments of the compounds of the present invention, R$^1$ and R$^2$ are both simultaneously C$_{1-4}$ aliphatic. Preferred R$^1$ and R$^2$ include methyl, ethyl, or propyl.

In other embodiments of the compounds of the present invention, R$^1$ and R$^2$ are both C$_{1-4}$ alphatic or R$^1$ and R$^2$ taken together form a 4-6 membered heterocyclic ring having up to 2 nitrogen heteroatoms. Preferred R$^1$ and R$^2$ include methyl, ethyl, propyl; or R$^1$ and R$^2$, taken together form an optionally substituted 1-pyrrolidinyl or 1-piperazinyl. In one embodiment, R$^1$ and R$^2$ both are methyl or ethyl, or R$^1$ and R$^2$, taken together form a 1-pyrrolidinyl ring, R$^3$ is ethyl or propyl. In another embodiment, R$^1$ and R$^2$ both are methyl or ethyl, In one embodiment of the present invention, R$^1$ and R$^2$ are both C$_{1-4}$ alphatic or R$^1$ and R$^2$ taken together form a 4-6 membered heterocyclic ring having up to 2 nitrogen heteroatoms. Preferred R$^1$ and R$^2$ include methyl, ethyl, propyl; or R$^1$ and R$^2$, taken together form 1-azetidinyl, 1-pyrrolidinyl, or 2,5-dihydropyrrolyl. Preferably, R$^1$ and R$^2$ are both methyl or ethyl.

In one embodiment of the present invention, R$^1$ and R$^2$ are both C$_{1-4}$ alphatic or R$^1$ and R$^2$ taken together form a 4-6 membered heterocyclic ring having up to 2 nitrogen heteroatoms. Preferred R$^1$ and R$^2$ include methyl, ethyl, propyl; or R$^1$ and R$^2$, taken together form an optionally substituted 1-azetidinyl, 1-pyrrolidinyl, 2,5-dihydro-1H-pyrrolyl, 1-piperidinyl, or 1-piperazinyl. In one embodiment, R$^1$ and R$^2$ are both C$_{1-4}$ alphatic. Preferably, R$^1$ and R$^2$ are both methyl or ethyl.

In one embodiment of the present invention, R$^1$ and R$^2$ are both C$_{1-4}$ alphatic Preferably, R$^1$ and R$^2$ are both methyl or ethyl. In other embodiments of the present invention, one of R$^1$ or R$^2$ is hydrogen and the other of R$^1$ or R$^2$ is an optionally substituted C$_{1-4}$aliphatic group, wherein one or more methylene units in the C$_{1-4}$aliphatic group are optionally replaced with NR, O, (CO)O, O(CO), NR(CO), (CO)NR, SO$_2$(NR), or (NR)SO$_2$.

In one embodiment of the present invention, R$^1$ is hydrogen or C$_{1-6}$ aliphatic and R$^2$ is optionally substituted C$_{1-6}$ aliphatic, or R$^1$ and R$^2$ taken together form an optionally substituted 4-7 membered saturated ring, wherein said ring optionally contains a second heteroatom selected from O or N. In a preferred embodiment, R$^1$ is hydrogen or C$_{1-6}$ aliphatic and R$^2$ is optionally substituted C$_{1-6}$ aliphatic, furanylmethyl, allyl, or benzyl, or R$^1$ and R$^2$ taken together is 4-carboethoxy-1-piperidinyl, 2-methylpiperidinyl, 2-hydroxymethylpiperidinyl, 3-hydroxypiperidinyl, 4-isobutylcarbamate-1-piperidinyl, 3-diethylaminocarbonyl-1-piperidinyl, 1-piperidyl, 1-pyrrolidinyl, 2-carboethoxypyrrolidinyl, N-morpholino, 3,5-dimethyl-N-morpholino, 4-methylpiperazinyl, 4-hydroxyethyl piperazinyl, 1-pyrrolyl, 2,4-dihydro-1-pyrrolyl, 1-azetidinyl, or 1-azepanyl. Preferably, R$^1$ is hydrogen or C$_{1-4}$ aliphatic and R$^2$ is C$_{1-4}$ aliphatic, furanylmethyl, allyl, or benzyl, or R$^1$ and R$^2$ taken together is 4-carboethoxy-1-piperidinyl, 2-methylpiperidinyl, 4-isobutylcarbamate-1-piperidinyl, 3-diethylaminocarbonyl-1-piperidinyl, 1-piperidyl, 1-pyrrolidinyl, 2-carboethoxypyrrolidinyl, 4-methylpiperazyl, 2,4-dihydro-1-pyrrolyl, 1-azetidinyl, or 1-azepanyl. Or, R$^1$ is hydrogen or C$_{1-4}$ aliphatic and R$^2$ C$_{1-4}$ aliphatic, furanylmethyl, allyl, or benzyl, or R$^1$ and R$^2$ taken together is 4-carboethoxy-1-piperidinyl, 2-methylpiperidinyl, 1-piperidinyl, 1-pyrrolidinyl, 4-methylpiperazyl, 2,4-dihydro-1-pyrrolyl, or 1-azetidinyl;

In another embodiment of the present invention, R$^1$ and R$^2$ are both methyl, or R$^1$ and R$^2$ taken together form 1-pyrrolidinyl, N-morpholinyl, 1-piperidyl, or 4-methyl piperidyl. Preferably, R$^1$ and R$^2$ are both methyl, or R$^1$ and R$^2$ taken together form 1-pyrrolidinyl, N-morpholinyl, 1-piperidyl, or 4-methyl piperidyl. Or, R$^1$ and R$^2$ are both methyl. Or, R$^1$ and R$^2$ taken together form 1-pyrrolidinyl, N-morpholinyl, 1-piperidyl, or 4-methyl piperidyl, preferably, 4-methyl piperidyl.

In another embodiment of the present invention, one of R$^1$ and R$^2$ is hydrogen, C$_{1-4}$ aliphatic, and the other of R$^1$ and R$^2$ is C$_{1-4}$ aliphatic, or benzyl, or R$^1$ and R$^2$ taken together form 1-pyrrolidinyl, 1-piperidinyl, or N-morpholinyl ring. Preferably, one of R$^1$ and R$^2$ is hydrogen, methyl, or ethyl, and the other of R$^1$ and R$^2$ is methyl, ethyl, or benzyl.

In other embodiments of the present invention, one of R$^1$ or R$^2$ is hydrogen and the other of R$^1$ or R$^2$ is a 5-6 membered aryl ring having 0-5 heteroatoms independently selected from nitrogen, oxygen, or sulfur, or a 3-7-membered saturated or partially unsaturated ring having 0-3 heteroatoms independently selected from nitrogen, oxygen, or sulfur. In other embodiments, one of R$^1$ or R$^2$ is hydrogen, and the other of R$^1$ or R$^2$ is an optionally substituted C$_{1-4}$aliphatic group, wherein one or more methylene units in the C$_{1-4}$aliphatic group are optionally replaced with NR, O, (CO)O, O(CO), NR(CO), (CO)NR, SO$_2$(NR), or (NR)SO$_2$.

In embodiments of the present invention, wherein R$^1$ or R$^2$ is a 5- or 6-membered aryl ring having 0-5 heteroatoms independently selected from N, O, or S, or a 3-7-membered saturated or partially unsaturated ring having 0-3 heteroatoms independently selected from N, O, or S, preferred R$^1$ and R$^2$ groups are selected from:

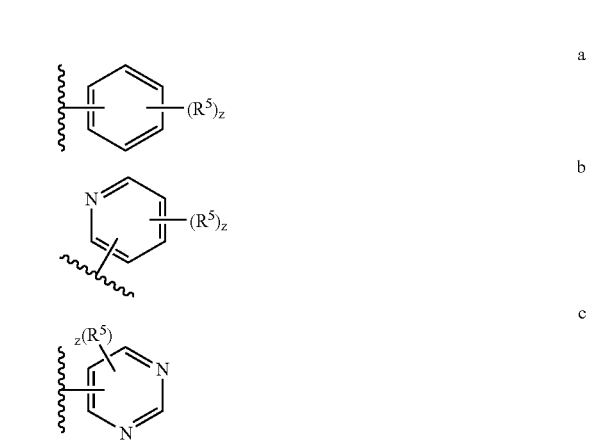

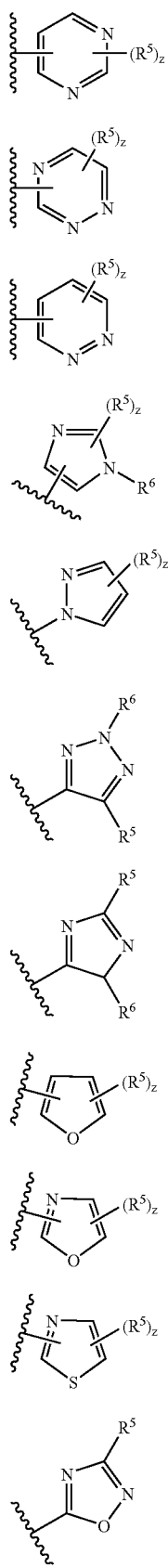
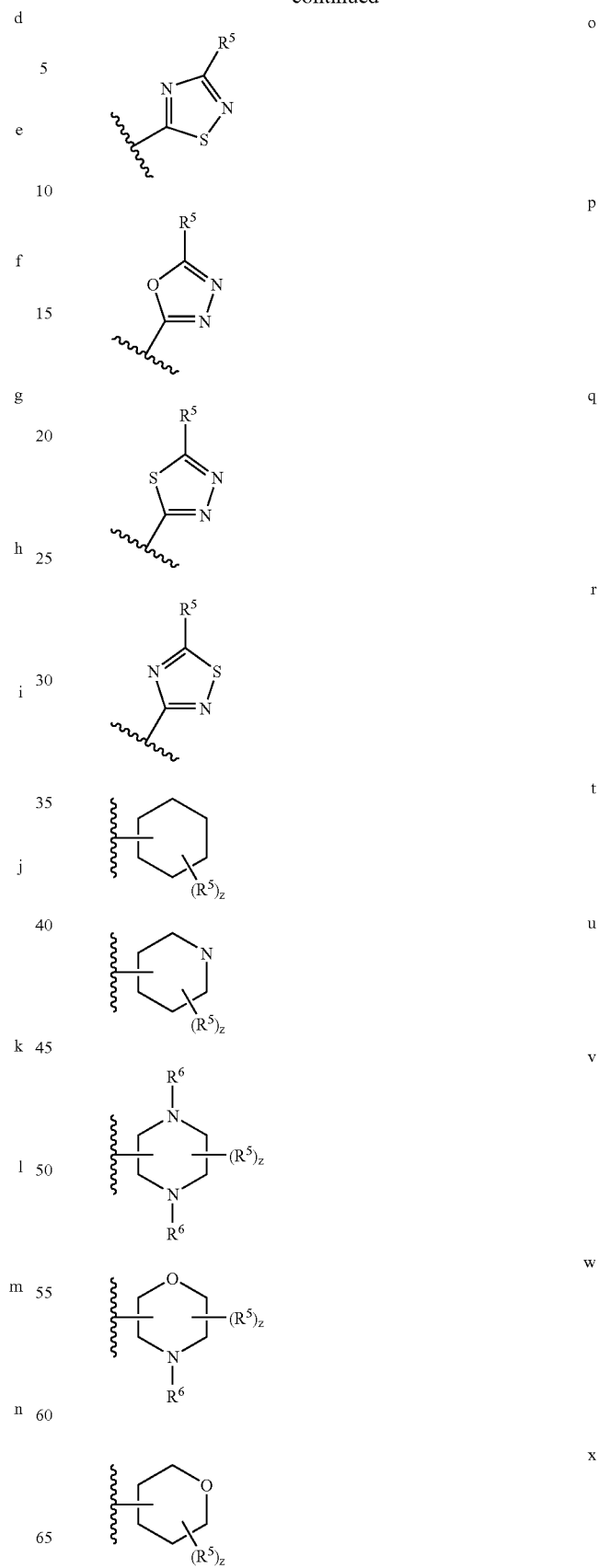

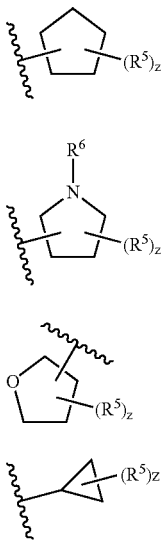

wherein $R^5$ and $R^6$ are as previously defined and z is 0-4. Most preferred rings include those shown below in Table 2.

In still other embodiments of the present invention, $R^1$ and $R^2$, taken together with the nitrogen atom to which they are bound, form an optionally substituted 3-8 membered heterocyclyl ring having 1-3 heteroatoms independently selected from nitrogen, sulfur, or oxygen. In certain preferred embodiments, $R^1$ and $R^2$ are taken together with the nitrogen atom to which they are bound and form a 3-8 membered heterocyclyl group selected from:

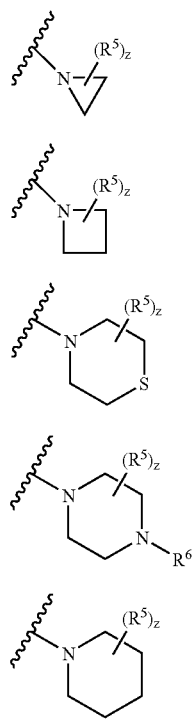

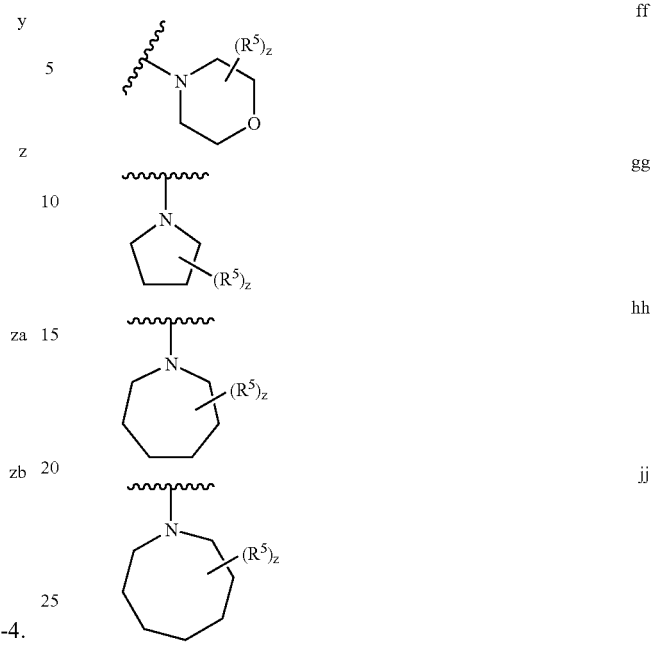

wherein $R^5$ and $R^6$ are as previously defined and z is 0-4.

In certain preferred embodiments of the present invention, $R^1$ and $R^2$ are taken together are an optionally substituted azetidinyl ring (bb). Or, $R^1$ and $R^2$ are taken together are an optionally substituted piperidinyl ring (ee). Or, $R^1$ and $R^2$ are taken together are an optionally substituted piperazinyl ring (dd). Or, $R^1$ and $R^2$ are taken together are an optionally substituted pyrrolidinyl ring (gg).

In other preferred of the present invention, $R^1$ and $R^2$ taken together are optionally substituted pyrrolidin-1-yl (ff), piperidinyl (ee), piperazin-1-yl (dd), or morpholin-4-yl (ee).

In certain other embodiments of the compounds of the present invention, $R^1$ and $R^2$ are each independently an optionally substituted $C_{1-6}$ aliphatic group, or $R^1$ and $R^2$ taken together form an optionally substituted pyrrolidinyl ring.

In certain other embodiments of the compounds of the present invention, $R^1$ and $R^2$ are each independently an optionally substituted $C_{1-6}$ aliphatic group, or $R^1$ and $R^2$ taken together form an optionally substituted piperidinyl ring.

In certain other embodiments of the compounds of the present invention, $R^1$ and $R^2$ are each independently an optionally substituted $C_{1-6}$ aliphatic group, or $R^1$ and $R^2$ taken together form an optionally substituted piperazinyl ring.

In certain other embodiments of the compounds of the present invention, $R^1$ and $R^2$ are each independently an optionally substituted $C_{1-6}$ aliphatic group, or $R^1$ and $R^2$ taken together form an optionally substituted azetidinyl ring In certain other embodiments of the compounds of the present invention, $R^1$ and $R^2$ are each independently an optionally substituted $C_{1-6}$ aliphatic group, $R^1$ and $R^2$ taken together form an optionally substituted pyrrolidinyl ring, optionally substituted piperidyl ring, optionally substituted dihydropyrrolidinyl ring, or optionally substituted azetidinyl ring.

In the present invention, when $R^1$ or $R^2$ is a 5-6 membered aryl ring having 0-5 heteroatoms independently selected from nitrogen, oxygen, or sulfur, or a 3-7 membered saturated or partially unsaturated ring having 0-3 heteroatoms independently selected from nitrogen, oxygen, or sulfur, or when $R^1$ and $R^2$, taken together with the nitrogen atom to which they are bound, form an optionally substituted 3-8 membered heterocyclyl or heteroaryl ring having 1-3 heteroatoms independently selected from nitrogen, oxygen, or sulfur, each ring is independently optionally substituted at one or more carbon atoms with 0-4 occurrences of —$R^5$, and at one or more substitutable nitrogen atoms with —$R^6$.

In preferred embodiments of the present invention, z is 0-3. In other preferred embodiments, z is 0 and the ring is unsubstituted.

Preferred $R^5$ groups, when present, are halogen, CN, $NO_2$, or an optionally substituted group selected from $C_{1-6}$alkyl, aryl, aryl($C_{1-6}$)alkyl, —N(R')$_2$, —CH$_2$N(R')$_2$, OR', —CH$_2$OR', SR', —CH$_2$SR', COOR', —NRCOR', —NRC(O)OR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, $R^5$ groups are each independently Cl, Br, F, $CF_3$, $CHF_2$, Me, Et, propyl, CN, $NO_2$, —COOH, $NH_2$, —N($C_{1-4}$ alkyl)$_2$, —O($C_{1-4}$ alkyl)$OCH_3$, —$CONH_2$, —NHC(O)$C_{1-4}$ alkyl, —NHC(O)($C_{5-6}$ heterocyclyl), —NHC(O)O$C_{1-4}$ alkyl, —NHC(O)O($C_{5-6}$ heterocyclyl), —C(O)O$C_{1-4}$ alkyl, —C(O)O($C_{5-6}$ heterocyclyl), OH, —$CH_2OH$, —NHCO $C_{1-4}$ alkyl, —NHC(O)($C_{5-6}$ heterocyclyl), —$SO_2NH_2$, or $SO_2N$($C_{1-4}$ alkyl)$_2$. In certain embodiments, $R^5$ groups are each independently Cl, Br, F, $CF_3$, Me, Et, CN, $NO_2$, —COOH, $NH_2$, —N($CH_3$)$_2$, —N(Et)$_2$, —N(iPr)$_2$, —O($CH_2$)$_2OCH_3$, —$CONH_2$, —$COOCH_3$, —OH, —$CH_2OH$, —$NHCOCH_3$, —NHC(O)O(iPr), —NHC(O)O-tetrahydrofuranyl, —$SO_2NH_2$, $SO_2N(CH_3)_2$piperidinyl, piperizinyl, morpholino, or an optionally substituted group selected from $C_{1-4}$alkoxy, phenyl, phenyloxy, benzyl, or benzyloxy. Most preferred $R^5$ groups include those shown below in Table 2. In preferred embodiments, $R^6$ groups are hydrogen, or an optionally substituted group selected from $C_{1-6}$alkyl, aryl, aryl($C_{1-6}$)alkyl, —N(R')$_2$, —CH$_2$N(R')$_2$, —CH$_2$OR', —CH$_2$SR', —(CH$_2$)$_2$N(R')$_2$, —(CH$_2$)$_2$OR', —(CH$_2$)$_2$SR', —COR', —C(O)OR', CON(R')$_2$, or —S(O)$_2$N(R')$_2$. In more preferred embodiments, $R^6$ groups are each independently H, Me, $CF_3$, ethyl, propyl, butyl, pentyl, CO($C_1$-$C_4$alkyl), —$CONH_2$, —C(O)($C_1$-$C_4$alkyl), —C(O)($C_{5-6}$ heterocyclyl), —C(O)O($C_1$-$C_4$alkyl), —C(O)O($C_{5-6}$heterocyclyl), —$CH_2OH$, —$SO_2NH_2$, $SO_2N(CH_3)_2$, or optionally substituted phenyl. Most preferred $R^6$ groups include those shown below in Table 2.

In certain embodiments of the present invention, $R^1$ and $R^2$ identical.

In certain embodiments of the present invention, $R^Z$ is —C(O)$R^3$. In other embodiments, $R^Z$ is —C(O)O$R^3$. In certain other embodiments, $R^Z$ is —$SO_2R'$, —$SO_2NHR'$, —$NHSO_2R'$, —P(O)(OR')$_2$, or —C(O)N(CN)R'. In yet other embodiments, $R^Z$ is an optionally substituted 5-membered heteroaryl ring having 1-4 heteroatoms selected from O, S, or N, or an optionally substituted pyran-4-one-yl.

In still other embodiments of the present invention, $R^z$ is an optionally substituted oxazolyl ring. In other embodiments, $R^Z$ is —(O)$R^3$, wherein $R^3$ is an optionally substituted $C_1$-$C_6$ alkyl group. In other embodiments, $R^Z$ is —C(O)$R^3$, wherin $R^3$ is an optionally substituted $C_1$-$C_6$ alkyl group or an aryl ring optionally substituted with 0-5 occurances of Q-$R^x$.

In yet other embodiments of the present invention, $R^z$ is an aryl ring optionally substituted with 0-5 occurrences of Q-$R^x$. Or $R^z$ is R'.

In other embodiments of the present invention, $R^z$ is C(O)$R^3$ where $R^3$ is an optionally substituted $C_1$-$C_6$ alkyl group, an aryl ring optionally substituted with 0-5 occurances of Q-$R^x$, an optionally substituted pyran-4-one-yl, or an optionally substituted 5-membered heteroaryl ring having 1-4 heteroatoms selected from O, S, or N.

In other embodiments of the present invention, $R^z$ is R', —C(O)$R^3$ where $R^3$ is an optionally substituted $C_1$-$C_6$ alkyl group, an aryl ring optionally substituted with 0-5 occurances of Q-$R^x$, an optionally substituted pyran-4-one-yl, or an optionally substituted 5-membered heteroaryl ring having 1-4 heteroatoms selected from O, S, or N.

In other embodiments of the present invention, $R^z$ is R', C(O)$R^3$ where $R^3$ is —N(R')$_2$, C(O)$R^3$ where $R^3$ is an optionally substituted $C_1$-$C_6$ alkyl group, an aryl ring optionally substituted with 0-5 occurances of Q-$R^x$, an optionally substituted pyran-4-one-yl, or an optionally substituted 5-membered heteroaryl ring having 1-4 heteroatoms selected from O, S, or N.

In other embodiments, $R^Z$ is —C(O)$R^3$, C(O)O$R^3$, CN, or an optionally substituted $C_1$-$C_6$ alkyl group where 0-5 carbon atoms have been optionally replaced with O, N, S, or carbonyl. Preferred $R^Z$ groups are as shown below in Table 2.

Preferred $R^Z$ groups are as shown below in Table 2.

In still other embodiments of the present invention $R^3$ is bonded to the carbon atom of the carbonyl group through an atom other than oxygen or nitrogen.

In yet other embodiments of the present invention, $R^3$ is further defined as —$CF_2H$, —$CF_3$, —$CHCl_2$, —$CHBr_2$, $CH_2CN$, —$CH_2OR'$, —$CH_2SR'$, —$CH_2N(R')_2$, or as Q-$R^x$; wherein Q is an optionally substituted $C_2$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN, provided that Q is bonded to the carbon atom of the carbonyl group through a carbon atom.

In still other embodiments of the present invention, $R^3$ is further defined as —$CF_2H$, —$CF_3$, —$CHCl_2$, —$CHBr_2$, $CH_2CN$, —$CH_2OR'$, —$CH_2SR'$, —$CH_2N(R')_2$, or as Q-$R^X$; wherein Q is a bond, and $R^X$ is an optionally substituted group selected from $C_{2-8}$ aliphatic, $C_{6-10}$ aryl, a heteroaryl ring having 5-10 ring atoms, or a heterocyclyl ring having 3-10 ring atoms.

In other embodiments, $R^3$ is hydrogen, or an optionally substituted group selected from $C_{1-6}$alkyl, aryl, aryl($C_{1-6}$) alkyl, —N(R')$_2$, —CH$_2$N(R')$_2$, —CH$_2$OR', —CH$_2$SR', —(CH$_2$)$_2$N(R')$_2$, —(CH$_2$)$_2$OR', —(CH$_2$)$_2$SR', —COR', —CON(R')$_2$, or —S(O)$_2$N(R')$_2$.

In still other preferred embodiments, $R^3$ is H, Me, $CF_3$, ethyl, propyl, butyl, pentyl, CO($C_1$-$C_4$alkyl), —$CONH_2$, —COO($C_1$-$C_4$alkyl), —$CH_2OH$, —$SO_2NH_2$, $SO_2N(CH_3)_2$, or optionally substituted phenyl. Most preferred $R^3$ groups include those shown below in Table 2.

In some embodiments of the present invention, $R^4$ is hydrogen. In other embodiments $R^4$ is an optionally substituted $C_1$-$C_6$ alkyl group. In yet other embodiments, $R^4$ is an optionally substituted aryl group. In other embodiments, $R^4$ is hydrogen or an optionally substituted $C_1$-$C_6$ alkyl group.

In preferred embodiments, $R^4$ is hydrogen, halogen, CN, $NO_2$, or an optionally substituted group selected from $C_{1-6}$alkyl, aryl, aryl($C_{1-6}$)alkyl, —N(R')$_2$, —CH$_2$N(R')$_2$, OR', —CH$_2$OR', SR', —CH$_2$SR', COOR', —NRCOR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, $R^4$ is H, Cl, Br, F, $CF_3$, Me, Et, CN, $NO_2$, —COOH, NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, SO$_2$N(CH$_3$)$_2$, piperidinyl, piperizinyl, morpholino, or an optionally substituted group selected from C$_{1-4}$alkoxy, phenyl, phenyloxy, benzyl, or benzyloxy. Most preferred R$^4$ groups include those shown below in Table 2.

As described generally above for the present invention, ring A is a 5-6 membered aryl ring having 0-5 heteroatoms independently selected from nitrogen, oxygen, or sulfur, optionally substituted at one or more carbon atoms with 0-5 occurrences of —R$^7$, and at one or more substitutable nitrogen atoms with —R$^8$.

In other embodiments of the present invention, ring A is a 3-7-membered saturated or partially unsaturated ring having 0-3 heteroatoms independently selected from nitrogen, oxygen, or sulfur, optionally substituted at one or more carbon atoms with 0-5 occurrences of —R$^7$, and at one or more substitutable nitrogen atoms with —R$^8$.

In certain embodiments of the present invention, ring A is a phenyl, pyridinyl, pyrimidinyl, pyridazinyl, pyrazinyl, pyrrolyl, piperidinyl, indolyl, indazolyl, benzotriazolyl, pyrazolyl, benzopyrazolyl, imidazolyl, benzimidazolyl, thiazolyl, benzthizolyl, oxazolyl, benzoxazolyl, isoxazolyl, benzisoxazolyl, isothiazolyl, benzisothiazolyl, triazolyl, benzotriazolyl, thiadiazolyl, thienyl, benzothienyl, furanoyl, benzofuranoyl, or triazinyl ring, each optionally substituted at one or more carbon atoms with 0-5 occurrences of —R$_7$, and at one or more substitutable nitrogen atoms with —R$^8$. It will be appreciated that ring A can be attached to the pyrimidinyl ring through any available carbon or nitrogen atom (e.g., a thiazole ring can be attached in the 2-, 4-, or 5-position). In certain preferred embodiments, ring A is optionally substituted phenyl, 2-pyridyl, 3-pyridyl, or 4-pyridyl:

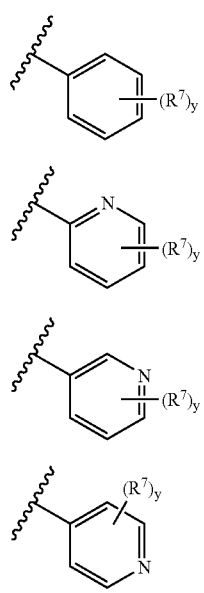

a b c d wherein y is 0-5 and R$^7$ is defined generally above.

In preferred embodiments, y is 0-3. In other preferred embodiments, y is 0 and ring A is unsubstituted.

In another embodiment of the present invention, ring A is:

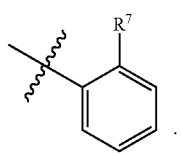

aa

In yet other embodiments of the present invention, ring A is an optionally substituted piperidyl ring or an optionally substituted pyrrolyl ring.

In certain other embodiments of the present invention, ring A is a phenyl ring optionally substituted with one or more halogens, an optionally substituted piperidyl ring, or an optionally substituted pyrrolyl ring.

In other embodiments of the present invention, ring A is a phenyl ring optionally substituted with 1-5 occurrences of Q-R$^x$, wherein Q is selected from a bond, O, N, and R$^x$ is R'.

In yet other embodiments of the present invention, ring A is a phenyl ring optionally substituted with 1-5 occurrences of Q-R$^x$, an optionally substituted imidazolyl ring, an optionally substituted pyrazolyl ring, an optionally substituted piperidyl ring, an optionally substituted pyrrolyl ring, or an optionally substituted indolyl ring.

In yet other embodiments of the present invention, ring A is a phenyl ring optionally substituted with one or more halogens, an optionally substituted piperidyl ring, an optionally substituted pyrrolyl ring. Or, ring A is a phenyl ring optionally substituted with 1-5 occurrences of Q-R$^x$ where Q is selected from a bond, O, N and R$^x$ is R'.

In certain embodiments of the present invention, ring A is a phenyl ring optionally substituted with one or more halogens, an optionally substituted piperidyl ring, an optionally substituted pyrrolyl ring, an optionally substituted thienyl ring, or ring A is a phenyl ring optionally substituted with 1-5 occurances of Q-R$^x$ where Q is selected from a bond, O, N and R$^x$ is selected from R'.

In preferred embodiments, R$^7$ groups are hydrogen, halogen, CN, NO$_2$, or an optionally substituted group selected from C$_{1-6}$alkyl, haloalkyl, aryl, aryl(C$_{1-6}$)alkyl, —N(R')$_2$, —CH$_2$N(R')$_2$, OR', —CH$_2$OR', SR', —CH$_2$SR', COOR', —NRCOR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, R$^7$ groups are each independently H, Cl, Br, F, CF$_3$, Me, Et, CN, NO$_2$, —COOH, NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —CHF$_2$, —NHCOCH$_3$, —SO$_2$NH$_2$, SO$_2$N(CH$_3$)$_2$, piperidinyl, piperizinyl, morpholino, or an optionally substituted group selected from C$_{1-4}$alkoxy, phenyl, phenyloxy, benzyl, or benzyloxy. Most preferred R$^7$ groups include any one of those shown below in Table 2. In preferred embodiments, R$^8$ groups are hydrogen, or an optionally substituted group selected from C$_{1-6}$alkyl, aryl, aryl(C$_{1-6}$)alkyl, —N(R')$_2$, —CH$_2$N(R')$_2$, —CH$_2$OR', —CH$_2$SR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, R$^8$ groups are each independently H, Me, CF$_3$, ethyl, propyl, butyl, pentyl, CO(C$_1$-C$_4$alkyl), —CONH$_2$, —COO(C$_1$-C$_4$alkyl), —CH$_2$OH, —SO$_2$NH$_2$, SO$_2$N(CH$_3$)$_2$, or optionally substituted phenyl. Most preferred R$^8$ groups include those shown below in Table 2.

In one embodiment of the present invention, ring A is phenyl having up to one Q-R$^x$ substituent, wherein Q is a bond or is a C$_1$-C$_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, or CN. Preferably, ring A is a 2-substituted phenyl, wherein said substituent is Q-$R^X$, wherein Q is a bond.

In another embodiment of the present invention, ring A is optionally substituted phenyl, 5 membered heteroaryl, or 6-membered heterocyclyl ring. Preferred ring A includes Preferred ring A includes phenyl or a 5-membered heteroaryl having 1 heteroatom, wherein said ring A has up to two Q-$R^X$ substituents, wherein Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, or CN. Or, and ring A is optionally substituted phenyl, piperidyl, or pyrrolyl. Preferred embodiments are those wherein ring A has up to two substituents selected from halo, OH, OCF₃, or $C_{1-4}$ aliphatic. Or, ring A is phenyl, 1-piperidyl, or 1-pyrrolyl, wherein ring A has up to two substituents selected from halo or OH.

In another embodiment of the present invention, ring A is optionally substituted phenyl, 5-membered heteroaryl, or six-membered heterocyclyl. Preferred ring A include phenyl having up to one Q-$R^X$ substituent, wherein Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, or CN. Or, ring A is phenyl optionally substituted with halo, or OH.

In another embodiment of the present invention, ring A is optionally substituted phenyl, 5-6 membered heterocyclic or heteroaryl ring. Preferred ring A includes phenyl or a 5-membered heteroaryl having 1 heteroatom, wherein said ring A has up to two Q-$R^X$ substituents, wherein Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, or CN. Or, ring A is phenyl, 1-pyrrolidyl, or 1-pyrrolyl, having up to two substituents selected from halo, OH, OCF₃, or $C_{1-4}$ aliphatic.

In another embodiment, ring A is phenyl having up to two Q-$R^X$ substituents, wherein Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, or CN. Preferably, ring A is phenyl having up to two substituents selected from halo, OH, OMe, OCF₃, or $C_{1-4}$ aliphatic.

In another embodiment, ring A is aryl or 5-10 membered heteroaromatic or heterocyclyl, having up to four Q-$R^X$ substituents, wherein Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, or CN. Preferably, ring A is phenyl, indolyl, or pyrrolyl having up to two substituents selected from halo, OH, OMe, OCF₃, or $C_{1-4}$ aliphatic. Or, ring A is phenyl or pyrrolyl having up to two substituents selected from halo, OH, OMe, OCF₃, or $C_{1-4}$ aliphatic. Or, ring A is phenyl or pyrrolyl having up to two substituents selected from halo, OH, OMe, OCF₃, or $C_{1-4}$ aliphatic.

In another embodiment$_{[KG}$26], ring A ring A is phenyl, 1-piperidinyl, 1-pyrrolyl, thienyl, 2-methyl-indol-1-yl, 3,4,-methyldioxyphenyl, having up to two $R^7$ substituents selected from H, Cl, Br, F, CF₃, CN, Me, —SMe, Et, —OH, —OCH₃, —OCF₃, —C(O)CH₃, or phenyloxy. Preferably, ring A is phenyl, 1-piperidinyl, 1-pyrrolyl, thienyl, 2-methyl-indol-1-yl, 3,4,-methyldioxyphenyl, having up to two $R^7$ substituents selected from H, Cl, Br, F, CF₃, CN, Me, —SMe, Et, —OH, —OCH₃, —OCF₃, —C(O)CH₃, or phenyloxy. Or, ring A is phenyl, 1-piperidinyl, 1-pyrrolyl, thienyl, 2-methyl-indol-1-yl, 3,4,-methyldioxyphenyl, having up to two $R^7$ substituents selected from H, Cl, Br, F, CF₃, Me, Et, —OH, —OCH₃, —OCF₃, or phenyloxy. Or, ring A is phenyl, 1-piperidyl or 1-pyrrolyl, having up to two $R^7$ substituents selected from H, Cl, Br, F, CF₃, Me, —OH, —OCF₃, phenyloxy, In another embodiment, the present invention provides compounds of formula IA, formula IB, or formula IC:

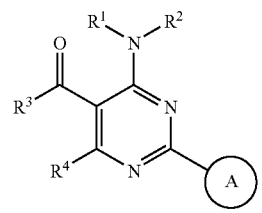

IA

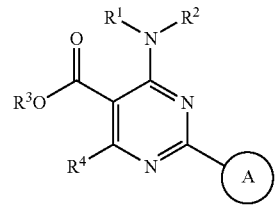

IB

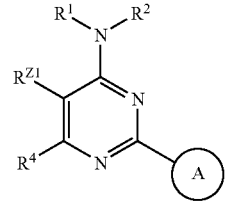

IC wherein $R^{Z1}$ is —SO₂R', —SO₂NHR', —NHSO₂R', —P(O)(OR')₂, —C(O)N(CN)R', an optionally substituted 5-membered heteroaryl ring having 1-4 heteroatoms selected from O, S, or N, or an optionally substituted pyran-4-one-yl.

In one embodiment of compounds of formula IA, $R^1$ and $R^2$ both are optionally substituted $C_{1-4}$ aliphatic, $R^3$ is $C_{1-4}$ aliphatic, $R^4$ is hydrogen, and ring A is optionally substituted phenyl. Preferred $R^1$ and $R^2$ include methyl, ethyl, or propyl. Preferred $R^3$ include ethyl, propyl or butyl. Preferred ring A includes phenyl having up to one Q-$R^X$ substituent, wherein Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, $NRSO_2NR$, O, S, or NR; and each occurrence of $R^X$ is independently selected from R', halogen, $NO_2$, or CN.

In one embodiment of compounds of formula IB, $R^1$ and $R^2$ both are optionally substituted $C_{1-4}$ aliphatic, $R^3$ is $C_{1-4}$ aliphatic, $R^4$ is hydrogen, and ring A is optionally substituted 5-6 membered aryl, heteroaryl, or heterocyclic ring. Preferred $R^1$ and $R^2$ include methyl, ethyl, or propyl. Preferred $R^3$ include ethy, propyl or butyl. Preferred ring A includes phenyl or a 5-6 membered heteroaryl or heterocyclyl ring having one nitrogen ring atom, wherein ring A has up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment of compounds of formula IC, $R^1$ and $R^2$ both are optionally substituted $C_{1-4}$ aliphatic, $R^{Z1}$ is an optionally substituted 5-membered heteroaryl ring having up to 2 heteroatoms selected from O and N, $R^4$ is hydrogen, and ring A is an optionally substituted phenyl. Preferred $R^1$ and $R^2$ include methyl, ethyl, or propyl. Preferred ring A includes phenyl having up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment of compounds of formula IA, $R^1$ and $R^2$ are both $C_{1-4}$ aliphatic or $R^1$ and $R^2$ taken together form a 5-6 membered heterocyclic ring, $R^3$ is optionally substituted $C_{1-4}$ aliphatic or aryl, $R^4$ is hydrogen, and ring A is optionally substituted phenyl. Preferred $R^1$ and $R^2$ include methyl, ethyl, or propyl; or $R^1$ and $R^2$, taken together form an optionally substiuted 1-pyrrolidinyl or 1-piperidinyl. Preferred $R^3$ includes optionally substituted ethyl, propyl, butyl, or phenyl. Preferred ring A include phenyl having up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In another embodiment, $R^1$ and $R^2$ both are methyl or ethyl, $R^3$ is ethyl or propyl, $R^4$ is hydrogen, and ring A is a 2-substituted phenyl, wherein said substituent is Q-$R^X$, wherein Q is a bond.

In one embodiment of formula IB, $R^1$ and $R^2$ are both $C_{1-4}$ alphatic or $R^1$ and $R^2$ taken together form a 3-6 membered heterocyclic ring having up to 2 heteroatoms, $R^3$ is optionally $C_{1-4}$ aliphatic, $R^4$ is hydrogen, and ring A is optionally substituted phenyl, 5 membered heteroaryl, or 6-membered heterocyclyl. Preferred $R^1$ and $R^2$ include methyl, ethyl, propyl; or $R^1$ and $R^2$, taken together form an optionally substituted 1-azetidinyl, 1-pyrrolidinyl, 1-piperidinyl, or 1-piperazinyl. Preferred $R^3$ includes optionally substituted ethyl, propyl, or butyl. Preferred ring A includes phenyl or a 5-membered heteroaryl having 1 heteroatom, wherein said ring A has up to two Q-$R^X$ substituents, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment, $R^1$ and $R^2$ both are methyl or ethyl, or $R^1$ and $R^2$, taken together form a 1-pyrrolidinyl ring, $R^3$ is ethyl or propyl, $R^4$ is hydrogen, and ring A is optionally substituted phenyl, piperidyl, or pyrrolyl. Preferred embodiments are those wherein ring A has up to two substituents selected from halo, OH, $OCF_3$, or $C_{1-4}$ aliphatic.

In one embodiment, $R^1$ and $R^2$ both are methyl or ethyl, $R^3$ is ethyl, $R^4$ is hydrogen, and ring A is phenyl, 1-piperidyl, or 1-pyrrolyl, wherein ring A has up to two substituents selected from halo or OH.

In one embodiment of formula IC, $R^1$ and $R^2$ are both $C_{1-4}$ alphatic, $R^{Z1}$ is a 5-membered heteraryl having up to two heteroatoms, $R^4$ is hydrogen, and ring A is an optionally substituted phenyl. Preferred $R^1$ and $R^2$ include methyl, ethyl, or propyl. Preferred $R^{Z1}$ includes optionally substituted oxazolyl. Preferred ring A includes phenyl having up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment of compounds of formula IA, $R^1$ and $R^2$ are both $C_{1-4}$ aliphatic, $R^3$ is optionally substituted $C_{1-4}$ aliphatic, $R^4$ is hydrogen, and ring A is optionally substituted phenyl. Preferred $R^1$ and $R^2$ include methyl or ethyl. Preferred $R^3$ includes optionally substituted ethyl, or propyl. Preferred ring A include phenyl having up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment of compounds of formula IA, $R^1$ and $R^2$ are both methyl or ethyl, $R^3$ is ethyl or propyl, $R^4$ is hydrogen, and ring A is phenyl optionally substituted with halo, or OH.

In one embodiment of formula IB, $R^1$ and $R^2$ are both $C_{1-4}$ alphatic or $R^1$ and $R^2$ taken together form a 4-6 membered heterocyclic ring having up to 2 nitrogen heteroatoms, $R^3$ is optionally substituted $C_{1-4}$ aliphatic, $R^4$ is hydrogen, and ring A is optionally substituted phenyl or 5-membered heteroaryl. Preferred $R^1$ and $R^2$ include methyl, ethyl, propyl; or $R^1$ and $R^2$, taken together form an optionally substituted 1-pyrrolidinyl or 1-piperazinyl. Preferred $R^3$ includes optionally substituted ethyl, propyl, or butyl. Preferred ring A includes phenyl or a 5-membered heteroaryl having 1 heteroatom, wherein said ring A has up to two Q-$R^X$ substituents, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment, $R^1$ and $R^2$ both are methyl or ethyl, or $R^1$ and $R^2$, taken together form a 1-pyrrolidinyl ring, $R^3$ is ethyl or propyl, $R^4$ is hydrogen, and ring A is optionally substituted phenyl, piperidyl, or pyrrolyl. Preferred embodiments are those wherein ring A has up to two substituents selected from halo, OH, $OCF_3$, or $C_{1-4}$ aliphatic.

In one embodiment, $R^1$ and $R^2$ both are methyl or ethyl, $R^3$ is ethyl, $R^4$ is hydrogen, and ring A is phenyl, 1-piperidyl, or 1-pyrrolyl, wherein ring A has up to two substituents selected from halo or OH.

In one embodiment of compounds of formula IA, $R^1$ and $R^2$ are both $C_{1-4}$ alphatic or $R^1$ and $R^2$ taken together form a 4-6 membered heterocyclic ring, $R^3$ is optionally substituted $C_{1-4}$ aliphatic or aryl, $R^4$ is hydrogen, and ring A is optionally substituted phenyl, 5-membered heteroaryl, or six-membered heterocyclyl. Preferred $R^1$ and $R^2$ include methyl, ethyl, or propyl; or $R^1$ and $R^2$, taken together form a 4-6 membered heterocyclic ring having up to 2 nitrogen heteroatoms, including 1-azetidinyl, 1-pyrrolidinyl, or 2,5-dihydropyrrolyl. Preferred $R^3$ includes optionally substituted ethyl, propyl, butyl, or phenyl. Preferred ring A include phenyl having up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment of compounds of formula IA, $R^1$ and $R^2$ are both methyl or ethyl, $R^3$ is ethyl or propyl, $R^4$ is hydrogen, and ring A is phenyl optionally substituted with halo, or OH.

In one embodiment of formula IB, $R^1$ and $R^2$ are both $C_{1-4}$ alphatic or $R^1$ and $R^2$ taken together form a 4-6 membered heterocyclic ring having up to 2 nitrogen heteroatoms, $R^3$ is optionally substituted $C_{1-4}$ aliphatic, $R^4$ is hydrogen, and ring A is optionally substituted phenyl, 5-6 membered heterocyclic or heteroaryl ring. Preferred $R^1$ and $R^2$ include methyl, ethyl, propyl; or $R^1$ and $R^2$, taken together form an optionally substituted 1-azetidinyl, 1-pyrrolidinyl, 2,5-dihydro-1H-pyrrolyl, 1-piperidinyl, or 1-piperazinyl. Preferred $R^3$ includes optionally substituted ethyl, propyl, or butyl. Preferred ring A includes phenyl or a 5-membered heteroaryl having 1 heteroatom, wherein said ring A has up to two Q-$R^X$ substituents, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment of formula IB, $R^1$ and $R^2$ are both $C_{1-4}$ alphatic, $R^3$ is ethyl, propyl, or butyl, $R^4$ is hydrogen, ring A is phenyl, 1-pyrrolidyl, or 1-pyrrolyl, having up to two substituents selected from halo, OH, $OCF_3$, or $C_{1-4}$ aliphatic.

In one embodiment of formula IB, $R^1$ and $R^2$ are both methyl or ethyl, $R^3$ is ethyl, $R^4$ is hydrogen, ring A is phenyl, 1-pyrrolidyl, or 1-pyrrolyl, having up to two substituents selected from halo, OH, $OCF_3$, or $C_{1-4}$ aliphatic. Preferred ring A in this embodiment includes optionally substituted 1-piperidyl or 1-pyrrolyl.

In one embodiment of formula IC, $R^1$ and $R^2$ are both $C_{1-4}$ alphatic, $R^{Z1}$ is a 5-membered heteraryl having up to two heteroatoms, $R^4$ is hydrogen, and ring A is an optionally substituted phenyl. Preferred $R^1$ and $R^2$ include methyl, ethyl, or propyl. Preferred $R^{Z1}$ includes optionally substituted oxazolyl, cyano, or aliphatic-oxymethyl. Preferred ring A includes phenyl having up to one Q-$R^X$ substituent, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment, $R^1$ and $R^2$ are both $C_{1-4}$ aliphatic, $R^3$ is $R^3$ is $C_{1-4}$ aliphatic, $R^4$ is hydrogen, and ring A is phenyl having up to two Q-$R^X$ substituents, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment, $R^1$ and $R^2$ are both methyl or ethyl, $R^3$ is propyl, n-butyl, or isobutyl, $R^4$ is hydrogen, and ring A is phenyl having up to two substituents selected from halo, OH, OMe, $OCF_3$, or $C_{1-4}$ aliphatic.

In one embodiment, $R^1$ and $R^2$ are both $C_{1-4}$ aliphatic, or $R^1$ and $R^2$ together form an optionally substituted 5-6 membered heterocyclic ring having up to 2 heteroatoms, $R^3$ is $C_{1-4}$ aliphatic, $R^4$ is hydrogen, and ring A is aryl or 5-10 membered heteroaromatic or heterocyclyl, having up to four Q-$R^X$ substituents, wherein Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN.

In one embodiment, $R^1$ and $R^2$ are both $C_{1-4}$ aliphatic, or $R^1$ and $R^2$ together form an optionally substituted 5-6 membered heterocyclic ring having up to 2 heteroatoms, $R^3$ is $C_{1-4}$ aliphatic, $R^4$ is hydrogen, and ring A is phenyl, indolyl, or pyrrolyl having up to two substituents selected from halo, OH, OMe, $OCF_3$, or $C_{1-4}$ aliphatic.

In one embodiment, $R^1$ and $R^2$ are both methyl or ethyl, or $R^1$ and $R^2$ together form an optionally substituted pyrrolidinyl or piperidinyl ring, $R^3$ is methyl or ethyl, $R^4$ is hydrogen, and ring A is phenyl or pyrrolyl having up to two substituents selected from halo, OH, OMe, $OCF_3$, or $C_{1-4}$ aliphatic.

In one embodiment, $R^1$ and $R^2$ are both methyl or ethyl, or $R^1$ and $R^2$ together form a pyrrolidinyl or 3-hydroxy-piperidinyl ring, $R^3$ is methyl or ethyl, $R^4$ is hydrogen, and ring A is phenyl or pyrrolyl having up to two substituents selected from halo, OH, OMe, $OCF_3$, or $C_{1-4}$ aliphatic.

In one embodiment of formula IC, $R^1$ and $R^2$ are both $C_{1-4}$ aliphatic, $R^{Z1}$ is optionally substituted phenyl or 5-membered heteroaromatic having up to 3 heteroatoms, $R^4$ is hydrogen, and ring A is phenyl having up to two substituents selected from halo, OH, OMe, $OCF_3$, or $C_{1-4}$ aliphatic. Or, $R^{Z1}$ in this embodiment is —C(O)NH($C_{1-4}$ aliphatic).

In one embodiment of formula I, $R^1$ and $R^2$ are both methyl or ethyl, $R^{Z1}$ is optionally substituted phenyl or oxadiazolyl, $R^4$ is hydrogen, and ring A is phenyl having up to two substituents selected from halo, OH, OMe, $OCF_3$, or $C_{1-4}$ aliphatic.

In another embodiment, ring A is optionally substituted phenyl, and compounds of formula IIA or formula IIB are provided:

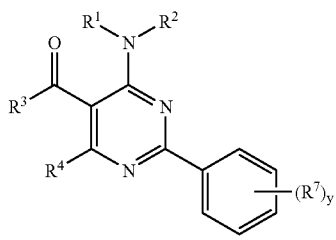

IIA

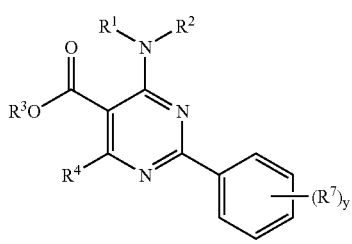

IIB wherein R¹, R², R³, R⁷, and y are defined generally above and in subsets herein.

In certain preferred embodiments, neither R¹ nor R² is hydrogen. In certain other embodiments, neither R¹ nor R² is hydrogen, and R¹ and R² are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$ aliphatic group, wherein one or more methylene units in the $C_{1-4}$ aliphatic group are optionally replaced with NR, O, (CO)O, O(CO), NR(CO), (CO)NR, SO₂(NR), or (NR)SO₂. In more preferred embodiments, both R¹ and R² are an optionally substituted $C_{1-4}$ aliphatic group, wherein one or more methylene units in the $C_{1-4}$ aliphatic group are optionally replaced with NR, O, (CO)O, O(CO), NR(CO), (CO)NR, SO₂(NR), or (NR)SO₂. In yet other preferred embodiments, when R¹ and R² are an optionally substituted $C_{1-4}$ aliphatic group, wherein one or more methylene units in the $C_{1-4}$ aliphatic group are optionally replaced with NR, O, (CO)O, O(CO), NR(CO), (CO)NR, SO₂(NR), or (NR)SO₂, preferred R¹ and R² groups are optionally substituted methyl, ethyl, cyclopropyl, n-propyl, propenyl, cyclobutyl, (CO)OCH₂CH₃, (CH₂)₂OCH₃, CH₂(CO)OCH₂CH₃, CH₂(CO)OCH₃, CH(CH₃)CH₂CH₃, or t-butyl, or n-butyl. Most preferred R¹ and R² groups include those shown below in Table 2.

In other preferred embodiments, one of R¹ or R² is hydrogen and the other of R¹ or R² is a 5-6 membered aryl ring having 0-5 heteroatoms independently selected from nitrogen, oxygen, or sulfur, or a 3-7-membered saturated or partially unsaturated ring having 0-3 heteroatoms independently selected from nitrogen, oxygen, or sulfur. In other embodiments, one of R¹ or R² is hydrogen, and the other of R¹ or R² is an optionally substituted $C_{1-4}$ aliphatic group, wherein one or more methylene units in the $C_{1-4}$ aliphatic group are optionally replaced with NR, O, (CO)O, O(CO), NR(CO), (CO)NR, SO₂(NR), or (NR)SO₂.

For those embodiments described above and herein where R¹ or R² is a 5- or 6-membered aryl ring having 0-5 heteroatoms independently selected from N, O, or S, or a 3-7-membered saturated or partially unsaturated ring having 0-3 heteroatoms independently selected from N, O, or S, preferred R¹ and R² groups are selected from:

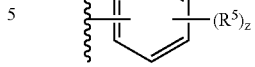 a

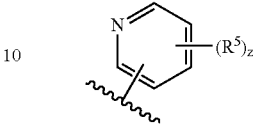 b

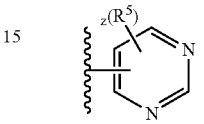 c

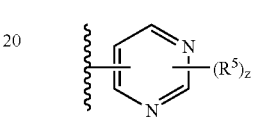 d

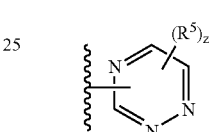 e

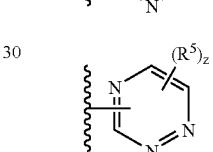 f

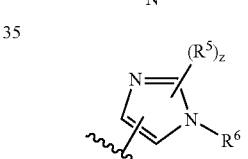 g

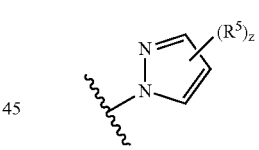 h

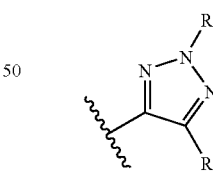 i

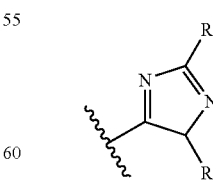 j

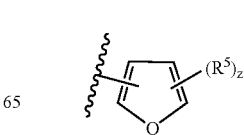 k

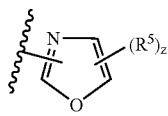

l

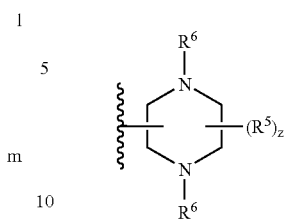

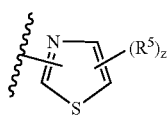

m

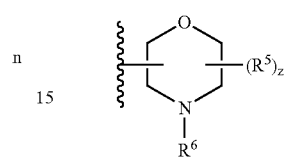

n

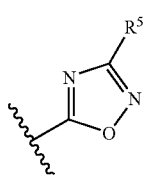

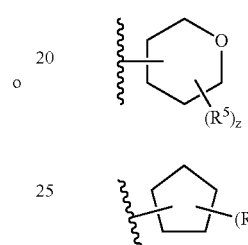

o

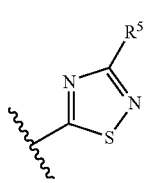

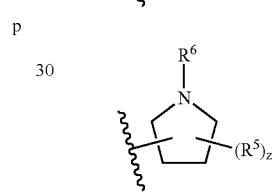

p

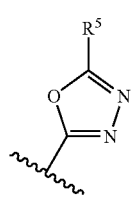

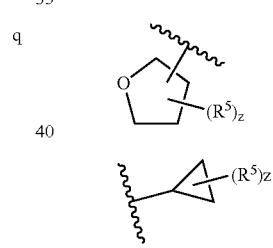

q

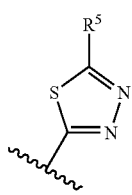

r

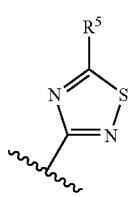

wherein $R^5$ and $R^6$ are as previously defined and z is 0-4. Most preferred rings include those shown below in Table 2.

In still other embodiments, for compounds of formula IIA or formula IIB, $R^1$ and $R^2$, taken together with the nitrogen atom to which they are bound, form an optionally substituted 3-8 membered heterocyclyl ring having 1-3 heteroatoms independently selected from nitrogen, sulfur, or oxygen. In certain preferred embodiments, $R^1$ and $R^2$ are taken together with the nitrogen atom to which they are bound and form a 3-8 membered heterocyclyl group selected from:

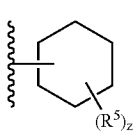

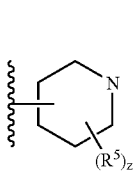

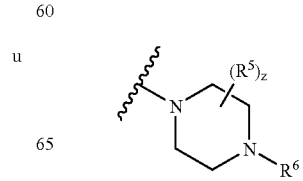

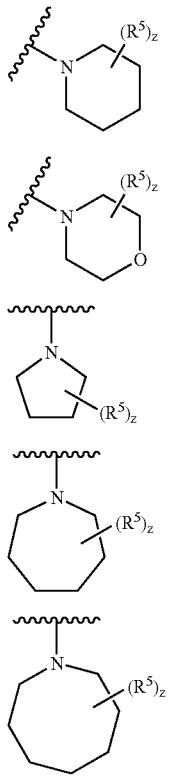

wherein $R^5$ and $R^6$ are as previously defined and z is 0-4.

In other preferred embodiments, for compounds of formula IIA or formula IIB, $R^1$ and $R^2$ taken together are optionally substituted pyrrolidin-1-yl (ff), piperidin-1-yl (dd), piperazin-1-yl (cc), or morpholin-4-yl (ee).

As described generally above, when $R^1$ or $R^2$ is a 5-6 membered aryl ring having 0-5 heteroatoms independently selected from nitrogen, oxygen, or sulfur, or a 3-7 membered saturated or partially unsaturated ring having 0-3 heteroatoms independently selected from nitrogen, oxygen, or sulfur, or when $R^1$ and $R^2$, taken together with the nitrogen atom to which they are bound, form an optionally substituted 3-8 membered heterocyclyl or heteroaryl ring having 1-3 heteroatoms independently selected from nitrogen, oxygen, or sulfur, the ring can be substituted with up to four independent occurrences of $R^5$. In preferred embodiments, z is 0-2. In other preferred embodiments, z is 0 and the ring is unsubstituted. Preferred $R^5$ groups, when present, are halogen, CN, NO$_2$, or an optionally substituted group selected from C$_{1-6}$alkyl, aryl, aryl(C$_{1-6}$)alkyl, —N(R')$_2$, —CH$_2$N(R')$_2$, OR', —CH$_2$OR', SR', —CH$_2$SR', COOR', —NRCOR', NRC(O)OR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, $R^5$ groups are each independently Cl, Br, F, CF$_3$, Me, Et, CN, NO$_2$, —COOH, NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, SO$_2$N(CH$_3$)$_2$, piperidinyl, piperizinyl, morpholino, or an optionally substituted group selected from C$_{1-4}$alkoxy, phenyl, phenyloxy, benzyl, or benzyloxy. Most preferred $R^5$ groups include those shown below in Table 2. In preferred embodiments, $R^6$ groups are hydrogen, or an optionally substituted group selected from C$_{1-6}$alkyl, aryl, aryl(C$_{1-6}$)alkyl, —N(R')$_2$, —CH$_2$N(R')$_2$, —CH$_2$OR', —CH$_2$SR', —(CH$_2$)$_2$N(R')$_2$, —(CH$_2$)$_2$OR', —(CH$_2$)$_2$SR', —COR', —C(O)OR', —CON (R')$_2$, or —S(O)$_2$N(R')$_2$. In more preferred embodiments, $R^6$ groups are each independently H, Me, CF$_3$, ethyl, propyl, butyl, pentyl, CO(C$_1$-C$_4$alkyl), —CONH$_2$, —COO(C$_1$-C$_4$alkyl), —CH$_2$OH, —SO$_2$NH$_2$, SO$_2$N(CH$_3$)$_2$, or optionally substituted phenyl. Most preferred $R^6$ groups include those shown below in Table 2.

In still other embodiments, for compounds of formula IIA as described generally above and in subsets herein $R^3$ is bonded to the carbon atom of the carbonyl group through an atom other than oxygen or nitrogen.

In yet other embodiments, for compounds of general formula IIA or formula IIB, $R^3$ is further defined as —CF$_2$H, —CF$_3$, —CHCl$_2$, —CHBr$_2$, CH$_2$CN, —CH$_2$OR', —CH$_2$SR', —CH$_2$N(R')$_2$, or as Q-R$^X$; wherein Q is an optionally substituted C$_2$-C$_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^X$ is independently selected from R', halogen, NO$_2$, or CN, provided that Q is bonded to the carbon atom of the carbonyl group through a carbon atom.

In still other preferred embodiments, for compounds of general formula IIA or formula IIB, $R^3$ is further defined as Q-R$^X$; wherein Q is a bond, and R$^X$ is an optionally substituted group selected from C$_{2-8}$ aliphatic, C$_{6-10}$ aryl, a heteroaryl ring having 5-10 ring atoms, or a heterocyclyl ring having 3-10 ring atoms.

In other preferred embodiments, $R^3$ is an optionally substituted group selected from C$_{1-6}$alkyl, aryl, aryl(C$_{1-6}$)alkyl, —CH$_2$N(R')$_2$, —CH$_2$OR', —CH$_2$SR', —(CH$_2$)$_2$N(R')$_2$, —(CH$_2$)$_2$OR', or —(CH$_2$)$_2$SR'.

In still other preferred embodiments, for compounds of general formula IIA or formula IIB, $R^3$ is further defined as —CF$_2$H, —CF$_3$, —CHCl$_2$, —CHBr$_2$, CH$_2$CN, —CH$_2$OR', —CH$_2$SR', —CH$_2$N(R')$_2$, or as Q-R$^X$; wherein Q is a bond, and R$^X$ is an optionally substituted group selected from C$_{2-8}$ aliphatic, C$_{6-10}$ aryl, a heteroaryl ring having 5-10 ring atoms, or a heterocyclyl ring having 3-10 ring atoms.

In other preferred embodiments, $R^3$ is hydrogen, or an optionally substituted group selected from C$_{1-6}$alkyl, aryl, aryl(C$_{1-6}$)alkyl, —N(R')$_2$, —CH$_2$N(R')$_2$, —CH$_2$OR', —CH$_2$SR', —(CH$_2$)$_2$N(R')$_2$, —(CH$_2$)$_2$OR', —(CH$_2$)$_2$SR', —COR', —CON(R')$_2$, or —S(O)$_2$N(R')$_2$.

In still other embodiments, $R^3$ is H, Me, CF$_3$, ethyl, propyl, butyl, pentyl, CO(C$_1$-C$_4$alkyl), —CONH$_2$, —COO(C$_1$-C$_4$alkyl), —CH$_2$OH, —SO$_2$NH$_2$, SO$_2$N(CH$_3$)$_2$, or optionally substituted phenyl. Most preferred $R^3$ groups include those shown below in Table 2.

In preferred embodiments, $R^4$ is hydrogen, halogen, CN, NO$_2$, or an optionally substituted group selected from C$_{1-6}$alkyl, aryl, aryl(C$_{1-6}$)alkyl, —N(R')$_2$, —CH$_2$N(R')$_2$, OR', —CH$_2$OR', SR', —CH$_2$SR', COOR', —NRCOR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, $R^4$ is H, Cl, Br, F, CF$_3$, Me, Et, CN, NO$_2$, —COOH, NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, SO$_2$N(CH$_3$)$_2$, piperidinyl, piperizinyl, morpholino, or an optionally substituted group selected from C$_{1-4}$alkoxy, phenyl, phenyloxy, benzyl, or benzyloxy. Most preferred $R^4$ groups include those shown below in Table 2.

In preferred embodiments, y is 0-2. In other preferred embodiments, y is 0 and ring A is unsubstituted. In preferred embodiments, $R^7$ groups are hydrogen, halogen, CN, NO$_2$, or an optionally substituted group selected from $C_{1-6}$alkyl, haloalkyl, aryl, aryl($C_{1-6}$)alkyl, —N(R')$_2$, —CH$_2$N(R')$_2$, OR', —CH$_2$OR', SR', —CH$_2$SR', COOR', —NRCOR', —(CH$_2$)$_2$N(R')$_2$, —(CH$_2$)$_2$OR', —(CH$_2$)$_2$SR', —COR', —CON(R')$_2$, or —S(O)$_2$N(R')$_2$. In more preferred embodiments, R$^7$ groups are each independently H, Cl, Br, F, CF$_3$, —CHF$_2$, Me, Et, CN, NO$_2$, —COOH, NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCF$_3$, —CH$_2$OH, —NHCOCH$_3$, —SO$_2$NH$_2$, SO$_2$N(CH$_3$)$_2$, piperidinyl, piperizinyl, morpholino, or an optionally substituted group selected from $C_{1-4}$alkoxy, phenyl, phenyloxy, benzyl, or benzyloxy. Most preferred R$^7$ groups include those shown below in Table 2.

In another embodiment, compounds of formula IIB have at least one, and preferably all, of the following features:
a. R$^1$ is hydrogen or $C_{1-6}$ aliphatic and R$^2$ is optionally substituted $C_{1-6}$ aliphatic, or R$^1$ and R$^2$ taken together form an optionally substituted 4-7 membered saturated ring, wherein said ring optionally contains a second heteroatom selected from O or N;
b. R$^3$ is methyl, ethyl,-propyl, isopropyl, butyl, —CH$_2$CCH, —CH$_2$C(O)CH$_3$, pyran-2-ylmethyl, optionally substituted phenyl, cyclopentyl, cyclohexyl, 3-chlorophenyl, or 3-tolyl;
c. ring A is phenyl, 1-piperidinyl, 1-pyrrolyl, thienyl, 2-methyl-indol-1-yl, 3,4,-methyldioxyphenyl, having up to two R$^7$ substituents selected from H, Cl, Br, F, CF$_3$, CN, Me, —SMe, Et, —OH, —OCH$_3$, —OCF$_3$, —C(O)CH$_3$, or phenyloxy.

In another embodiment, compounds of formula IIB have at least one, and preferably all, of the following features:
a. R$^1$ is hydrogen or $C_{1-6}$ aliphatic and R$^2$ is optionally substituted $C_{1-6}$ aliphatic, furanylmethyl, allyl, or benzyl, or R$^1$ and R$^2$ taken together is 4-carboethoxy-1-piperidinyl, 2-methylpiperidinyl, 2-hydroxymethylpiperidinyl, 3-hydroxypiperidinyl, 4-isobutylcarbamate-1-piperidinyl, 3-diethylaminocarbonyl-1-piperidinyl, 1-piperidyl, 1-pyrrolidinyl, 2-carboethoxypyrrolidinyl, N-morpholino, 3,5-dimethyl-N-morpholino, 4-methylpiperazinyl, 4-hydroxyethyl piperazinyl, 1-pyrrolyl, 2,4-dihydro-1-pyrrolyl, 1-azetidinyl, or 1-azepanyl;
b. R$^3$ is methyl, ethyl, propyl, isopropyl, butyl, —CH$_2$CCH, —CH$_2$C(O)CH$_3$, pyran-2-ylmethyl, optionally substituted phenyl, cyclopentyl, cyclohexyl, 3-chlorophenyl, or 3-tolyl;
c. ring A is phenyl, 1-piperidinyl, 1-pyrrolyl, thienyl, 2-methyl-indol-1-yl, 3,4,-methyldioxyphenyl, having up to two R$^7$ substituents selected from H, Cl, Br, F, CF$_3$, —CHF$_2$, CN, Me, —SMe, Et, —OH, —OCH$_3$, —OCF$_3$, —C(O)CH$_3$, or phenyloxy.

In another embodiment, compounds of formula IIB have at least one, and preferably all, of the following features:
a. R$^1$ is hydrogen or $C_{1-4}$ aliphatic and R$^2$ is $C_{1-4}$ aliphatic, furanylmethyl, allyl, or benzyl, or R$^1$ and R$^2$ taken together is 4-carboethoxy-1-piperidinyl, 2-methylpiperidinyl, 4-isobutylcarbamate-1-piperidinyl, 3-diethylaminocarbonyl-1-piperidinyl, 1-piperidyl, 1-pyrrolidinyl, 2-carboethoxypyrrolidinyl, 4-methylpiperazyl, 2,4-dihydro-1-pyrrolyl, 1-azetidinyl, or 1-azepanyl;
b. R$^3$ is methyl, ethyl, propyl, butyl, optionally substituted phenyl, cyclopentyl, or 3-tolylmethyl;
c. R$^4$ is hydrogen;
d. ring A is phenyl, 1-piperidinyl, 1-pyrrolyl, thienyl, 2-methyl-indol-1-yl, 3,4,-methyldioxyphenyl, having up to two R$^7$ substituents selected from H, Cl, Br, F, CF$_3$, —CHF$_2$, Me, Et, —OH, —OCH$_3$, —OCF$_3$, or phenyloxy.

In another embodiment, compounds of formula IIB have at least one, and preferably all, of the following features:
a. R$^1$ is hydrogen or $C_{1-4}$ aliphatic and R$^2$ $C_{1-4}$ aliphatic, furanylmethyl, allyl, or benzyl, or R$^1$ and R$^2$ taken together is 4-carboethoxy-1-piperidinyl, 2-methylpiperidinyl, 1-piperidinyl, 1-pyrrolidinyl, 4-methylpiperazyl, 2,4-dihydro-1-pyrrolyl, or 1-azetidinyl;
b. R$^3$ is methyl, ethyl, or propyl;
c. R$^4$ is hydrogen;
d. ring A is phenyl, 1-piperidyl or 1-pyrrolyl, having up to two R$^7$ substituents selected from H, Cl, Br, F, CF$_3$, —CHF$_2$, Me, —OH, —OCF$_3$, phenyloxy, In yet other preferred embodiments y is 1 and compounds have the general formula IIIA:

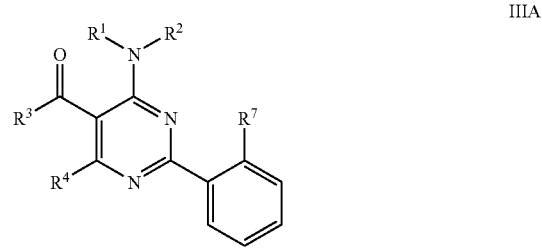

IIIA wherein R$^1$, R$^2$, R$^3$ and R$^4$ are described generally above and herein, and R$^7$ is halogen, CN, NO$_2$, or an optionally substituted group selected from $C_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$.

In another embodiment, compounds have the general formula IIIA, wherein R$^7$ is hydrogen.

In still other preferred embodiments compounds of the invention are defined according to formula IIIA and one or more of, or all of, R$^1$, R$^2$, R$^3$ or R$^4$ are further defined according to one or more of, or all of, the following groups:
a. R$^1$ and R$^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$aliphatic group, wherein one or more methylene units in the $C_{1-4}$aliphatic group are optionally replaced with NR, O, (CO)O, O(CO), NR(CO), (CO)NR, SO$_2$(NR), or (NR)SO$_2$;
b. R$^3$ is bonded to the carbon atom of the carbonyl group through an atom other than oxygen or nitrogen; or
c. R$^4$ is hydrogen, halogen, CN, NO$_2$, or an optionally substituted group selected from $C_{1-6}$alkyl, aryl, aryl($C_{1-6}$)alkyl, —N(R')$_2$, —CH$_2$N(R')$_2$, OR', —CH$_2$OR', SR', —CH$_2$SR', COOR', —NRCOR', —(CH$_2$)$_2$N(R')$_2$, —(CH$_2$)$_2$OR', —(CH$_2$)$_2$SR', —COR', —CON(R')$_2$, or —S(O)$_2$N(R')$_2$.

In still other preferred embodiments compounds of the invention are defined according to formula IIIA and one or more of, or all of, R$^1$, R$^2$, R$^3$ or R$^4$ are further defined according to one or more of, or all of, the following groups:
a. R$^1$ and R$^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2(NR)$, or $(NR)SO_2$;

b. $R^3$ is —$CF_2H$, —$CF_3$, —$CHCl_2$, —$CHBr_2$, $CH_2CN$, —$CH_2OR'$, —$CH_2SR'$, —$CH_2N(R')_2$, or as Q-$R^X$; wherein Q is an optionally substituted $C_2$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN, provided that Q is bonded to the carbon atom of the carbonyl group through a carbon atom; or c. $R^4$ is hydrogen, halogen, CN, $NO_2$, or an optionally substituted group selected from $C_{1-6}$alkyl, aryl, aryl($C_{1-6}$)alkyl, —$N(R')_2$, —$CH_2N(R')_2$, OR', —$CH_2OR'$, SR', —$CH_2SR'$, COOR', —NRCOR', —$(CH_2)_2N(R')_2$, —$(CH_2)_2OR'$, —$(CH_2)_2SR'$, —COR', —$CON(R')_2$, or —$S(O)_2N(R')_2$.

In still other preferred embodiments compounds of the invention are defined according to formula IIIA and one or more of, or all of, $R^1$, $R^2$, $R^3$ or $R^4$ are further defined according to one or more of, or all of, the following groups:

a. $R^1$ and $R^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2(NR)$, or $(NR)SO_2$;

b. $R^3$ is —$CF_2H$, —$CF_3$, —$CHCl_2$, —$CHBr_2$, $CH_2CN$, —$CH_2OR'$, —$CH_2SR'$, —$CH_2N(R')_2$, or as Q-$R^X$; wherein Q is a bond, and $R^X$ is an optionally substituted group selected from $C_{2-8}$ aliphatic, $C_{6-10}$ aryl, a heteroaryl ring having 5-10 ring atoms, or a heterocyclyl ring having 3-10 ring atoms; or c. $R^4$ is hydrogen, halogen, CN, $NO_2$, or an optionally substituted group selected from $C_{1-6}$alkyl, aryl, aryl($C_{1-6}$)alkyl, —$N(R')_2$, —$CH_2N(R')_2$, OR', —$CH_2OR'$, SR', —$CH_2SR'$, COOR', —NRCOR', —$(CH_2)_2N(R')_2$, —$(CH_2)_2OR'$, —$(CH_2)_2SR'$, —COR', —$CON(R')_2$, or —$S(O)_2N(R')_2$.

In still other preferred embodiments compounds of the invention are defined according to formula IIIA and one or more of, or all of, $R^1$, $R^2$, $R^3$ or $R^4$ are further defined according to one or more of, or all of, the following groups:

a. $R^1$ and $R^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2(NR)$, or $(NR)SO_2$;

b. $R^3$ is hydrogen, or an optionally substituted group selected from $C_{1-6}$alkyl, aryl, aryl($C_{1-6}$)alkyl, —$N(R')_2$, —$CH_2N(R')_2$, —$CH_2OR'$, —$CH_2SR'$, —$(C_2)_2N(R')_2$, —$(CH_2)_2OR'$, —$(CH_2)_2SR'$, —COR', —$CON(R')_2$, or —$S(O)_2N(R')_2$; or c. $R^4$ is hydrogen, halogen, CN, $NO_2$, or an optionally substituted group selected from $C_{1-6}$alkyl, aryl, aryl($C_{1-6}$)alkyl, —$N(R')_2$, —$CH_2N(R')_2$, OR', —$CH_2OR'$, SR', —$CH_2SR'$, COOR', —NRCOR', —$(CH_2)_2N(R')_2$, —$(CH_2)_2OR'$, —$(CH_2)_2SR'$, —COR', —$CON(R')_2$, or —$S(O)_2N(R')_2$.

In still other preferred embodiments compounds of the invention are defined according to formula IIIA and one or more of, or all of, $R^1$, $R^2$, $R^3$, $R^4$, or $R^7$ are further defined according to one or more of, or all of, the following groups:

a. $R^1$ and $R^2$ are each independently optionally substituted methyl, ethyl, cyclopropyl, n-propyl, propenyl, cyclobutyl, (CO)$OCH_2CH_3$, $(CH_2)_2OCH_3$, $CH_2$(CO)$OCH_2CH_3$, $CH_2$(CO)$OCH_3$, $CH(CH_3)CH_2CH_3$, or t-butyl, or n-butyl;

b. $R^3$ is H, Me, $CF_3$, ethyl, propyl, butyl, pentyl, CO($C_1$-$C_4$alkyl), —$CONH_2$, —COO($C_1$-$C_4$alkyl), —$CH_2OH$, —$SO_2NH_2$, $SO_2N(CH_3)_2$, or optionally substituted phenyl;

c. $R^4$ is H, Cl, Br, F, $CF_3$, Me, Et, CN, $NO_2$, —COOH, $NH_2$, —$N(CH_3)_2$, —N(Et)$_2$, —N(iPr)$_2$, —O$(CH_2)_2OCH_3$, —$CONH_2$, —$COOCH_3$, —OH, —$CH_2OH$, —NH$COCH_3$, —$SO_2NH_2$, $SO_2N(CH_3)_2$, piperidinyl, piperizinyl, morpholino, or an optionally substituted group selected from $C_{1-4}$alkoxy, phenyl, phenyloxy, benzyl, or benzyloxy; or d. $R^7$ is Cl, Br, F, $CF_3$, —$CHF_2$, Me, Et, CN, $NO_2$, —COOH, $NH_2$, —$N(CH_3)_2$, —N(Et)$_2$, —N(iPr)$_2$, —O$(CH_2)_2OCH_3$, —$CONH_2$, —$COOCH_3$, —OH, —$CH_2OH$, —NH$COCH_3$, —$SO_2NH_2$, $SO_2N(CH_3)_2$, piperidinyl, piperizinyl, morpholino, or an optionally substituted group selected from $C_{1-4}$alkoxy, phenyl, phenyloxy, benzyl, or benzyloxy.

In still other preferred embodiments compounds of the invention are defined according to formula IIIA and one or more of, or all of, $R^1$, $R^2$, $R^3$, $R^4$, or $R^7$ are further defined according to one or more of, or all of, the following groups:

a. $R^1$ and $R^2$ are each independently optionally substituted methyl, ethyl, cyclopropyl, n-propyl, propenyl, cyclobutyl, (CO)$OCH_2CH_3$, $(CH_2)_2OCH_3$, $CH_2$(CO)$OCH_2CH_3$, $CH_2$(CO)$OCH_3$, $CH(CH_3)CH_2CH_3$, or t-butyl, or n-butyl;

b. $R^3$ is H, Me, $CF_3$, ethyl, propyl, butyl, pentyl, CO($C_1$-$C_4$alkyl), —$CONH_2$, —COO($C_1$-$C_4$alkyl), —$CH_2OH$, —$SO_2NH_2$, $SO_2N(CH_3)_2$, or optionally substituted phenyl;

c. $R^4$ is H, Cl, Br, F, $CF_3$, Me, Et, CN, $NO_2$, —COOH, $NH_2$, —$N(CH_3)_2$, —N(Et)$_2$, —N(iPr)$_2$, —O$(CH_2)_2OCH_3$, —$CONH_2$, —$COOCH_3$, —OH, —$CH_2OH$, —NH$COCH_3$, —$SO_2NH_2$, $SO_2N(CH_3)_2$, piperidinyl, piperizinyl, morpholino, or an optionally substituted group selected from $C_{1-4}$alkoxy, phenyl, phenyloxy, benzyl, or benzyloxy; or d. $R^7$ is hydrogen.

In another embodiment, compounds of formula IIIA have at least one, and preferably all, of the following features:

a. $R^1$ and $R^2$ are both methyl, or $R^1$ and $R^2$ taken together form 1-pyrrolidinyl, N-morpholinyl, 1-piperidyl, or 4-methyl piperidyl;

b. $R^7$ is hydroxy, methoxy, or hydrogen;

c. $R^4$ is hydrogen; and d. $R^3$ is ethyl, propyl, isopropyl, butyl, isobutyl, pentyl, but-1-en-4-yl, cyclopentylethyl, or phenyl.

In another embodiment, compounds of formula IIIA have at least one, and preferably all, of the following features:

a. $R^1$ and $R^2$ are both methyl, or $R^1$ and $R^2$ taken together form 1-pyrrolidinyl, N-morpholinyl, 1-piperidyl, or 4-methyl piperidyl;

b. $R^7$ is hydroxy or hydrogen;

c. $R^4$ is hydrogen; and d. $R^3$ is ethyl, propyl, isopropyl, butyl, isobutyl, pentyl, but-1-en-4-yl, cyclopentylethyl, or phenyl.

In another embodiment, compounds of formula IIIA have at least one, and preferably all, of the following features:
a. $R^1$ and $R^2$ are both methyl;
b. $R^7$ is hydroxy;
c. $R^4$ is hydrogen; and
d. $R^3$ is ethyl, propyl, isopropyl, butyl, isobutyl, pentyl, or but-1-en4-yl.

In another embodiment, compounds of formula IIIA have at least one, and preferably all, of the following features:
a. $R^1$ and $R^2$ are both methyl;
b. $R^7$ is hydroxy;
c. $R^4$ is hydrogen; and
d. $R^3$ is optionally substituted phenyl, preferably, unsubstituted phenyl.

In another embodiment, compounds of formula IIIA have at least one, and preferably all, of the following features:
a. $R^1$ and $R^2$ taken together form 1-pyrrolidinyl, N-morpholinyl, 1-piperidyl, or 4-methyl piperidyl;
b. $R^7$ is hydroxy;
c. $R^4$ is hydrogen; and
d. $R^3$ is ethyl or propyl.

In another embodiment, compounds of formula IIIA have at least one, and preferably all, of the following features:
a. $R^1$ and $R^2$ are both methyl, or $R^1$ and $R^2$ taken together form 4-methyl piperidinyl;
b. $R^7$ is hydroxy;
c. $R^4$ is hydrogen; and
d. $R^3$ is ethyl, propyl, butyl, isobutyl, or but-1-en-4-yl.

In another embodiment, compounds of formula IIIA have at least one, and preferably all, of the following features:
a. one of $R^1$ and $R^2$ is hydrogen, $C_{1-4}$ aliphatic, and the other of $R^1$ and $R^2$ is $C_{1-4}$ aliphatic, or benzyl, or $R^1$ and $R^2$ taken together form 1-pyrrolidinyl, 1-piperidinyl, or N-morpholinyl ring;
b. $R^3$ is $C_{1-4}$ aliphatic;
c. $R^7$ is hydrogen; and
d. $R^4$ is $C_{1-4}$ aliphatic, phenyl, pyridyl, or thienyl.

In another embodiment, compounds of formula IIIA have at least one, and preferably all, of the following features:
a. one of $R^1$ and $R^2$ is hydrogen, methyl, or ethyl, and the other of $R^1$ and $R^2$ is methyl, ethyl, or benzyl;
b. $R^3$ is ethyl or propyl;
c. $R^7$ is hydrogen; and
d. $R^4$ is methyl, phenyl, pyridyl, or thienyl.

In yet other preferred embodiments y is 1 and compounds have the general formula IIIB:

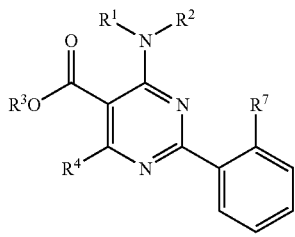

IIIB wherein $R^1$, $R^2$, $R^3$ and $R^4$ are described generally above and herein, and $R^7$ is halogen, CN, $NO_2$, or an optionally substituted group selected from $C_{1-4}$alkyl, aryl, aralkyl, —$N(R')_2$, —$CH_2N(R')_2$, —OR', —$CH_2OR'$, —SR', —$CH_2SR'$, —COOR', —NRCOR', —$CON(R')_2$, $SO_2R'$, or —$SO_2N(R')_2$.

In still other preferred embodiments compounds of the invention are defined according to formula IIIB, and one or more of, or all of, $R^1$, $R^2$, $R^3$ or $R^4$ are further defined according to one or more of, or all of, the following groups:
a. $R^1$ and $R^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$aliphatic group, wherein one or more methylene units in the $C_{1-4}$aliphatic group are optionally replaced with NR, O, (CO)O, O(CO), NR(CO), (CO)NR, $SO_2$(NR), or (NR)$SO_2$;
b. each occurrence of $R^3$ is independently an optionally substituted group selected from $C_{1-6}$alkyl, aryl, aryl($C_{1-6}$)alkyl, $CH_2OR'$, —$CH_2SR'$, —$(CH_2)_2N(R')_2$, —$(CH_2)_2OR'$, —$(CH_2)_2SR'$, —COR', or —$CON(R')_2$; and
c. each occurrence of $R^4$ is independently hydrogen, halogen, CN, $NO_2$, or an optionally substituted group selected from $C_{1-6}$alkyl, aryl, aryl($C_{1-6}$)alkyl, —$N(R')_2$, —$CH_2N(R')_2$, OR', —$CH_2OR'$, SR', —$CH_2SR'$, COOR', —NRCOR', —$(CH_2)_2N(R')_2$, —$(CH_2)_2OR'$, —$(CH_2)_2SR'$, —COR', —$CON(R')_2$, $SO_2R'$, or —$SO_2N(R')_2$.

In still other preferred embodiments compounds of the invention are defined according to formula IIIB, and one or more of, or all of, $R^1$, $R^2$, $R^3$ or $R^4$ are further defined according to one or more of, or all of, the following groups:
a. $R^1$ and $R^2$ are each independently optionally substituted methyl, ethyl, cyclopropyl, n-propyl, propenyl, cyclobutyl, $(CO)OCH_2CH_3$, $(CH_2)_2OCH_3$, $CH_2(CO)OCH_2CH_3$, $CH_2(CO)OCH_3$, $CH(CH_3)CH_2CH_3$, or t-butyl, or n-butyl;
b. each occurrence of $R^3$ is Me, $CF_3$, ethyl, propyl, butyl, pentyl, $CO(C_1-C_4$alkyl), —$CONH_2$, —$COO(C_1-C_4$alkyl), —$CH_2OH$, or optionally substituted phenyl or benzyl; and
c. each occurrence of $R^4$ is H, Cl, Br, F, $CF_3$, Me, Et, CN, $NO_2$, —COOH, $NH_2$, —$N(CH_3)_2$, —$N(Et)_2$, —$N(iPr)_2$, —$O(CH_2)_2OCH_3$, —$CO(C_1-C_4$alkyl), —$CONH_2$, —$COOCH_3$, —OH, —$CH_2OH$, —$NHCOCH_3$, —$SO_2(C_1-C_4$alkyl), —$SO_2NH_2$, —$SO_2N(CH_3)_2$, piperidinyl, piperizinyl, morpholino, or an optionally substituted group selected from $C_{1-4}$alkoxy, phenyl, phenyloxy, benzyl, or benzyloxy.

In still other preferred embodiments compounds of the invention are defined according to formula IIIB, and one or more of, or all of, $R^1$, $R^2$, $R^3$, $R^4$ or $R^7$ are further defined according to one or more of, or all of, the following groups:
a. $R^1$ and $R^2$ are each independently optionally substituted methyl, ethyl, cyclopropyl, n-propyl, propenyl, cyclobutyl, $(CO)OCH_2CH_3$, $(CH_2)_2OCH_3$, $CH_2(CO)OCH_2CH_3$, $CH_2(CO)OCH_3$, $CH(CH_3)CH_2CH_3$, or t-butyl, or n-butyl;
b. each occurrence of $R^3$ is Me, $CF_3$, ethyl, propyl, butyl, pentyl, $CO(C_1-C_4$alkyl), —$CONH_2$, —$COO(C_1-C_4$alkyl), —$CH_2OH$, or optionally substituted phenyl or benzyl;
c. each occurrence of $R^4$ is H, Cl, Br, F, $CF_3$, Me, Et, CN, $NO_2$, —COOH, $NH_2$, —$N(CH_3)_2$, —$N(Et)_2$, —$N(iPr)_2$, —$O(CH_2)_2OCH_3$, —$CO(C_1-C_4$alkyl), —$CONH_2$, —$COOCH_3$, —OH, —$CH_2OH$, —$NHCOCH_3$, —$SO_2(C_1-C_4$alkyl), —$SO_2NH_2$, —$SO_2N(CH_3)_2$, piperidinyl, piperizinyl, morpholino, or an optionally substituted group selected from $C_{1-4}$alkoxy, phenyl, phenyloxy, benzyl, or benzyloxy; and d. $R^7$ is Cl, Br, F, $CF_3$, $OCF_3$, Me, Et, propyl, n-butyl, t-butyl, CN, $NO_2$, —COOH, $NH_2$, —$N(CH_3)_2$, —$N(Et)_2$, —$N(iPr)_2$, —$O(CH_2)_2OCH_3$, —$CO(C_1$-$C_4$alkyl), —$CONH_2$, $CON(CH_3)_2$, —$COOCH_3$, —OH, —$SCH_3$, —$CH_2OH$, —$NHCOCH_3$, —$SO_2(C_1$-$C_4$alkyl), —$SO_2NH_2$, —$SO_2N(CH_3)_2$, piperidinyl, piperizinyl, morpholino, or an optionally substituted group selected from $C_{1-4}$alkoxy, phenyl, phenyloxy, benzyl, or benzyloxy.

In another embodiment, compounds of formula IIIB have at least one, and preferably all, of the following features:
a. one of $R^1$ and $R^2$ is hydrogen, $C_{1-4}$ aliphatic, and the other of $R^1$ and $R^2$ is $C_{1-4}$ aliphatic, or benzyl, or $R^1$ and $R^2$ taken together form 1-pyrrolidinyl, 1-piperidinyl, or N-morpholinyl ring;
b. $R^3$ is $C_{1-4}$ aliphatic;
c. $R^7$ is hydrogen; and
d. $R^4$ is $C_{1-4}$ aliphatic, phenyl, pyridyl, or thienyl.

In another embodiment, compounds of formula IIIB have at least one, and preferably all, of the following features:
a. one of $R^1$ and $R^2$ is hydrogen, methyl, or ethyl, and the other of $R^1$ and $R^2$ is methyl, ethyl, or benzyl;
b. $R^3$ is ethyl or propyl;
c. $R^7$ is hydrogen; and
d. $R^4$ is methyl, phenyl, pyridyl, or thienyl.

In another embodiment, ring A is optionally substituted phenyl, and compounds of formula IIC are provided:

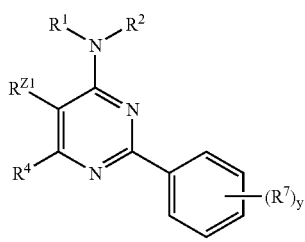

IIC wherein $R^1$, $R^3$, $R^4$, $R^7$, and y are defined generally above and in subsets herein; and wherein $R^{Z1}$ is —$SO_2R'$, —$SO_2NHR'$, —$NHSO_2R'$, —$P(O)(OR')_2$, —$C(O)N(CN)R'$, or an optionally substituted ring selected from:

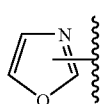

z-a

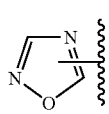

z-b

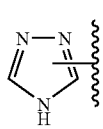

z-c

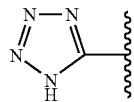

z-d

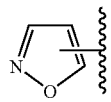

z-e

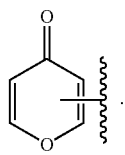

z-f

In certain embodiments, $R^{Z1}$ is —$SO_2R'$, —$SO_2NHR'$, —$NHSO_2R'$, —$P(O)(OR')_2$, —$C(O)N(CN)R'$. Preferred $R^{Z1}$ include —$SO_2NHR'$, —$NHSO_2R'$, or —$C(O)N(CN)R'$. In certain preferred embodiments, $R^{Z1}$ is —$SO_2R'$, —$NHSO_2R'$, or —$C(O)N(CN)R'$.

In certain other embodiments, $R^{Z1}$ is a ring selected from:

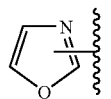

z-a

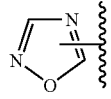

z-b

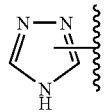

z-c

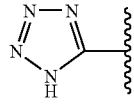

z-d

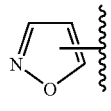

z-e

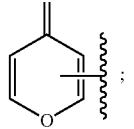

z-f wherein said ring is optionally substituted with R' or OR'.

In still other preferred embodiments compounds of the invention are defined according to formula IIC, and one or more of, or all of, $R^1$, $R^2$, or $R^4$ are further defined according to one or more of, or all of, the following groups:

a. $R^1$ and $R^2$ are each independently selected from a 5- or 6-membered aryl ring having 0-5 heteroatoms independently selected from N, O, or S; a 3-7-membered saturated or partially unsaturated ring having 0-3 heteroatoms independently selected from N, O, or S; or an optionally substituted $C_{1-4}$ aliphatic group, wherein one or more methylene units in the $C_{1-4}$ aliphatic group are optionally replaced with NR, O, (CO)O, O(CO), NR(CO), (CO)NR, $SO_2$(NR), or (NR)$SO_2$; and b. each occurrence of $R^4$ is independently hydrogen, halogen, CN, $NO_2$, or an optionally substituted group selected from $C_{1-6}$alkyl, aryl, aryl($C_{1-6}$)alkyl, —N(R')$_2$, —$CH_2$N(R')$_2$, OR', —$CH_2$OR', SR', —$CH_2$SR', COOR', —NRCOR', —($CH_2$)$_2$N(R')$_2$, —($CH_2$)$_2$OR', —($CH_2$)$_2$SR', —COR', —CON(R')$_2$, $SO_2$R', or —$SO_2$N(R')$_2$.

In still other preferred embodiments compounds of the invention are defined according to formula IIC, and one or more of, or all of, $R^1$, $R^2$, or $R^4$ are further defined according to one or more of, or all of, the following groups:

a. $R^1$ and $R^2$ are each independently optionally substituted methyl, ethyl, cyclopropyl, n-propyl, propenyl, cyclobutyl, (CO)OCH$_2$CH$_3$, (CH$_2$)$_2$OCH$_3$, CH$_2$(CO) OCH$_2$CH$_3$, CH$_2$(CO)OCH$_3$, CH(CH$_3$)CH$_2$CH$_3$, or t-butyl, or n-butyl; and b. each occurrence of $R^4$ is H, Cl, Br, F, CF$_3$, Me, Et, CN, NO$_2$, —COOH, NH$_2$, —N(CH$_3$)$_2$, —N(Et)$_2$, —N(iPr)$_2$, —O(CH$_2$)$_2$OCH$_3$, —CO(C$_1$-C$_4$alkyl), —CONH$_2$, —COOCH$_3$, —OH, —CH$_2$OH, —NHCOCH$_3$, —SO$_2$ (C$_1$-C$_4$alkyl), —SO$_2$NH$_2$, —SO$_2$N(CH$_3$)$_2$, piperidinyl, piperizinyl, morpholino, or an optionally substituted group selected from $C_{1-4}$alkoxy, phenyl, phenyloxy, benzyl, or benzyloxy.

In still other preferred embodiments compounds of the invention are defined according to formula IIC, and one or more of, or all of, $R^1$, $R^2$, $R^4$ or $R^7$ are further defined according to one or more of, or all of, the following groups:

a. $R^1$ and $R^2$ are each independently optionally substituted methyl, ethyl, cyclopropyl, n-propyl, propenyl, cyclobutyl, (CO)OCH$_2$CH$_3$, (CH$_2$)$_2$OCH$_3$, CH$_2$(CO) OCH$_2$CH$_3$, CH$_2$(CO)OCH$_3$, CH(CH$_3$)CH$_2$CH$_3$, or t-butyl, or n-butyl;

b. each occurrence of $R^4$ is H, Cl, Br, F, CF$_3$, Me, Et, CN, NO$_2$, —COOH, NH$_2$, —N(CH$_3$)$_2$, —N(Et)$_2$, —N(iPr)$_2$, —O(CH$_2$)$_2$OCH$_3$, —CO(C$_1$-C$_4$alkyl), —CONH$_2$, —COOCH$_3$, —OH, —CH$_2$OH, —NHCOCH$_3$, —SO$_2$ (C$_1$-C$_4$alkyl), —SO$_2$NH$_2$, —SO$_2$N(CH$_3$)$_2$, piperidinyl, piperizinyl, morpholino, or an optionally substituted group selected from $C_{1-4}$alkoxy, phenyl, phenyloxy, benzyl, or benzyloxy; and c. $R^7$ is Cl, Br, F, CF$_3$, OCF$_3$, Me, Et, propyl, n-butyl, t-butyl, CN, NO$_2$, —COOH, NH$_2$, —N(CH$_3$)$_2$, —N(Et)$_2$, —N(iPr)$_2$, —O(CH$_2$)$_2$OCH$_3$, —CO(C$_1$-C$_4$alkyl), —CONH$_2$, CON(CH$_3$)$_2$, —COOCH$_3$, —OH, —SCH$_3$, —CH$_2$OH, —NHCOCH$_3$, —SO$_2$(C$_1$-C$_4$alkyl), —SO$_2$NH$_2$, —SO$_2$N(CH$_3$)$_2$, piperidinyl, piperizinyl, morpholino, or an optionally substituted group selected from $C_{1-4}$alkoxy, phenyl, phenyloxy, benzyl, or benzyloxy.

In another embodiment, ring A is optionally substituted phenyl, and compounds of formula IIIC are provided:

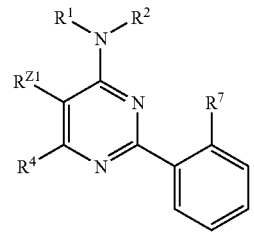

IIIC wherein $R^1$, $R^2$, $R^3$, and $R^7$ are defined generally above and in subsets herein; and wherein $R^{Z1}$ is —SO$_2$R', —NHSO$_2$R', —C(O)N(CN)R', or an optionally substituted ring selected from:

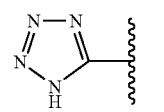

z-dd

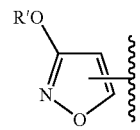

z-ee

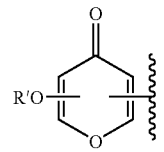

z-ff

In certain embodiments of formula IIIC, $R^1$ and $R^2$ are identical, and they both are methyl or ethyl. Or, $R^1$ and $R^2$ are taken together to form a 1-piperidyl, 1-piperazyl, or 1-pyrrolidinyl.

In certain embodiments, ring A is optionally substituted phenyl, and compounds of IVC are provided:

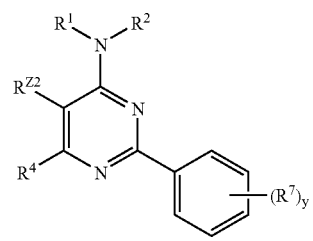

IVC $R^{Z2}$ is cyano or halo, $R^7$, y, $R^1$, $R^2$, and $R^4$ are as defined above.

In certain embodiments of compounds of formula IVC, when $R^1$ and $R^2$ both are simultaneously hydrogen, then ring A is not

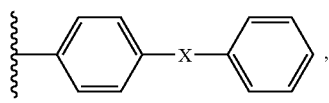

wherein X is O, NH, S, or CH$_2$, and each of the two phenyl ring is optionally substituted.

In certain embodiments of formula IVC, the following compounds are excluded:

| R$^1$ | R$^2$ | R$^{Z1}$ | R$^4$ | Ring A |
|---|---|---|---|---|
| H | 4-pyridyl | F | H | 2-F-4-Cl-phenyl |
| H | 3-methyl-pyridin-4-yl | I | H | 2-F-4-Cl-phenyl |
| H | quinolin-6-yl | F | H | 3-formylphenyl |
| H | Quinolin-6-yl | Br | H | 3-cyanophenyl |
| H | 1H-indazol-3-yl | Cl | H | 2-CF$_3$-phenyl |
| H | —CH2-CCH | Br | H | phenyl |
| H | H | Br | H | phenyl |
| H | H | F | H | phenyl |
| H | phenyl | CN | H | Phenyl |
| H | phenyl | CN | H | 4-Cl-phenyl |
| H | 4-tolyl | CN | H | 4-Cl-phenyl |
| H | Ph | CN | H | 4-OMe-phenyl |
| H | 4-tolyl | CN | H | phenyl |
| H | 3-tolyl | CN | H | phenyl |
| H | 3-Cl-phenyl | CN | H | phenyl |
| H | H | CN | H | phenyl |
| H | methoxyethyl | CN | H | phenyl |
| H | allyl | CN | H | phenyl |
| H | cyclopropyl | CN | H | phenyl |
| H | 1-naphthyl | CN | H | phenyl |
| H | —CH2-C(O)NH2 | CN | H | phenyl |
| H | —CH2C(O)OEt | CN | H | phenyl |
| Me | cyanomethyl | CN | H | phenyl |
| H | 3-CF3-phenyl | CN | H | phenyl |
| H | isobutyl | Cl | H | phenyl |
| H | H | Cl | H | phenyl |
| H | Ph | Cl | H | phenyl |
| H | acyl | Br | H | phenyl |
| H | acyl | CN | H | phenyl |
| H | 6-quinolinyl | Br | H | 4-OMe-phenyl |
| H | 6-quinolinyl | Br | H | 3-Cl-phenyl |
| H | 6-quinolinyl | Br | H | 3-Br-phenyl |
| H | 6-quinolinyl | Br | H | 3-OMe-phenyl |
| H | 6-quinolinyl | Br | H | 3-CF$_3$-4-Cl-phenyl |
| H | 6-quinolinyl | Br | H | 3-CF3-4-CN-phenyl |
| H | 6-quinolinyl | Br | H | 4-cyanophenyl |
| H | 6-quinolinyl | F | H | 4-NO$_2$-phenyl |
| H | 6-quinolinyl | F | H | 3-NO$_2$-phenyl |
| H | 6-quinolinyl | F | H | 4-N(Me$_2$)-phenyl |
| H | 6-quinolinyl | F | H | 4-(N-morpholino)-phenyl |

In certain other embodiments of formula IVC, the following compounds are excluded:

| R$^1$ and R$^2$ taken together form: | R$^{Z1}$ | R$^4$ | Ring A |
|---|---|---|---|
| N-morpholino | F | H | phenyl |
| 2H-pyridazin-3-one-1-yl | Cl | H | phenyl |
| N-piperidyl | Cl | H | phenyl |
| N-morpholino | Cl | H | phenyl |
| N-piperidyl | Cl | H | 4-NO$_2$-phenyl |
| N-morpholino | CN | H | 2-OH-phenyl |

Representative examples of compounds as described above and herein are set forth below in Table 2.

The compounds described in this invention are useful as inhibitors of ion channels, preferably, voltage gated sodium channels and N-type calcium channels. In certain exemplary embodiments, compounds of the invention are useful as inhibitors of NaV1.2. In certain exemplary embodiments, compounds of the invention are useful as inhibitors of NaV1.5. In certain exemplary embodiments, compounds of the invention are useful as inhibitors of NaV1.8. In other embodiments, compounds of the invention are useful as inhibitors of NaV 1.8 and CaV2.2. In yet other embodiments, compounds of this invention are useful as inhibitors of CaV2.2. In yet other embodiments, comopunds of this invention are useful as dual inhibitors of NaV1.8 and a TTX-sensitive ion channel such as NaV1.3 or NaV1.7.

TABLE 2

| Cmpd No. | Compound |
|---|---|
| 1 | |
| 2 | |
| 3 | |
| 4 | |

TABLE 2-continued

| Cmpd No. | Compound |
|---|---|
| 5 | *(structure)* |
| 6 | *(structure)* |
| 7 | *(structure)* |
| 8 | *(structure)* |
| 9 | *(structure)* |
| 10 | *(structure)* |
| 11 | *(structure)* |
| 12 | *(structure)* |
| 13 | *(structure)* |

TABLE 2-continued
| Cmpd No. | Compound |
|---|---|
| 14 | 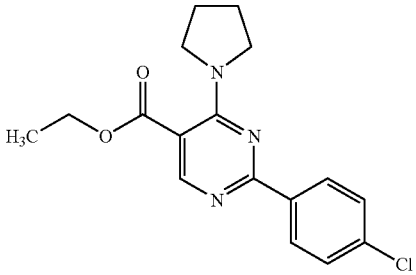 |
| 15 | 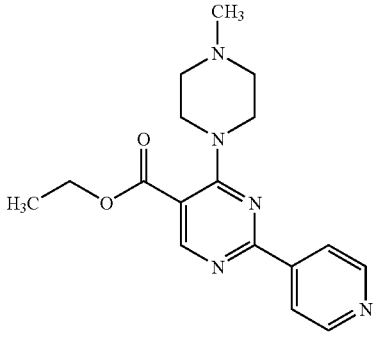 |
| 16 | 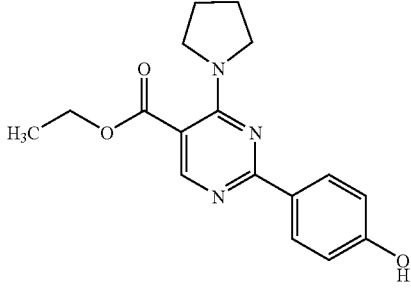 |
| 17 | 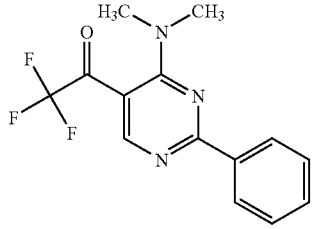 |
| 18 | 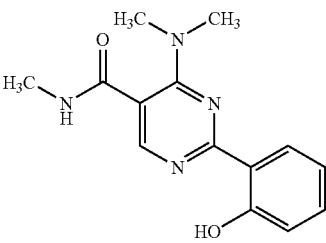 |
| 19 | 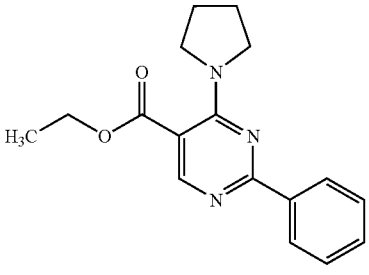 |
| 20 | 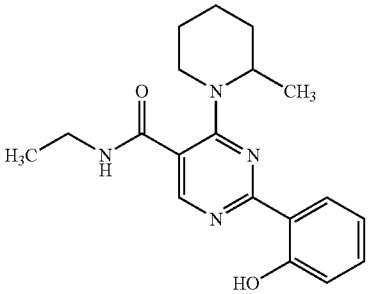 |
| 21 | 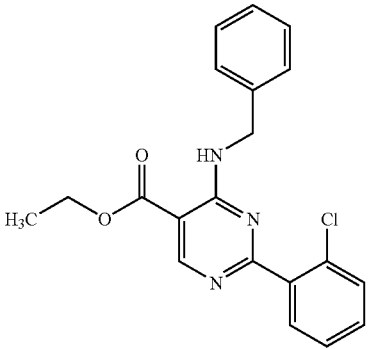 |
| 22 | |
| 23 | |

TABLE 2-continued

| Cmpd No. | Compound |
|---|---|
| 24 | ethyl 4-(dimethylamino)-2-(2-fluoro-3-methoxyphenyl)pyrimidine-5-carboxylate |
| 25 | ethyl 4-(2-methylpiperidin-1-yl)-2-(2-methoxyphenyl)pyrimidine-5-carboxylate |
| 26 | ethyl 2-(3-aminophenyl)-4-(dimethylamino)pyrimidine-5-carboxylate |
| 27 | ethyl 4-(dimethylamino)-2-morpholinopyrimidine-5-carboxylate |
| 28 | ethyl 4-(dimethylamino)-2-phenyl-6-(thiophen-2-yl)pyrimidine-5-carboxylate |
| 29 | ethyl 4-(dimethylamino)-2-(2-hydroxyphenyl)pyrimidine-5-carboxylate |
| 30 | 2-methylene-5,5,5-trifluoropent-3-enyl 4-(dimethylamino)-2-phenylpyrimidine-5-carboxylate |
| 31 | ethyl 6-methyl-4-(methylamino)-2-phenylpyrimidine-5-carboxylate |
| 32 | ethyl 4-(dimethylamino)-2-(5-fluoro-2-methoxyphenyl)pyrimidine-5-carboxylate |
| 33 | ethyl 4-(dimethylamino)-2-(3-(trifluoromethyl)phenyl)pyrimidine-5-carboxylate |

TABLE 2-continued

| Cmpd No. | Compound |
|---|---|
| 34 | |
| 35 | |
| 36 | |
| 37 | |
| 38 | |
| 39 | |
| 40 | |
| 41 | |
| 42 | |
| 43 | |

TABLE 2-continued

| Cmpd No. | Compound |
|---|---|
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |

TABLE 2-continued

| Cmpd No. | Compound |
|---|---|
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |

TABLE 2-continued
| Cmpd No. | Compound |
|---|---|
| 64 | 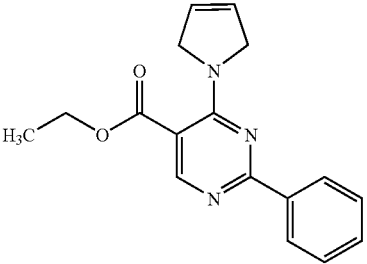 |
| 65 | 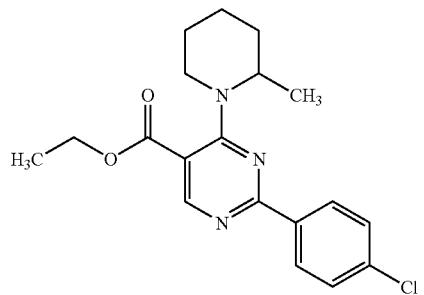 |
| 66 | 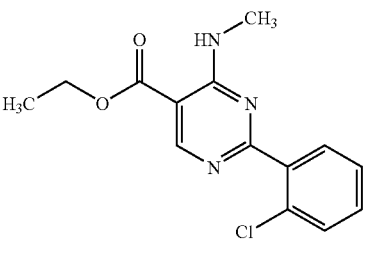 |
| 67 | 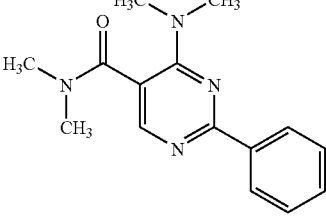 |
| 68 | 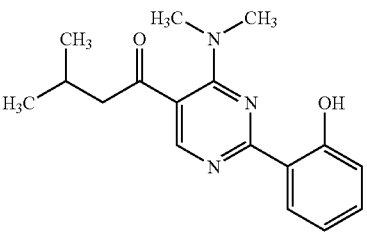 |
| 69 | 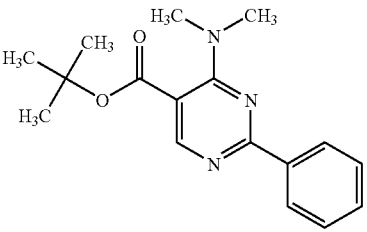 |
TABLE 2-continued
| Cmpd No. | Compound |
|---|---|
| 70 | 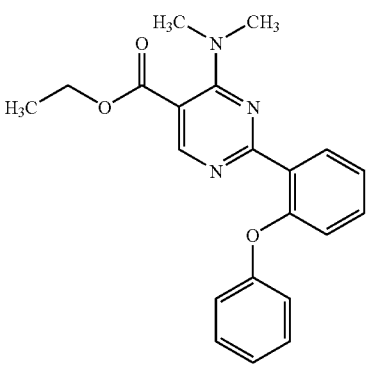 |
| 71 | 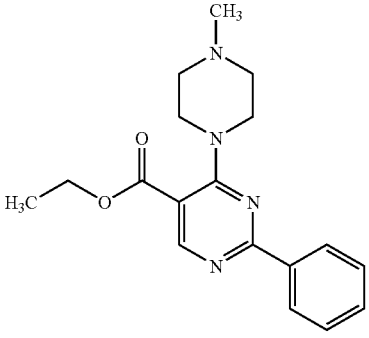 |
| 72 | 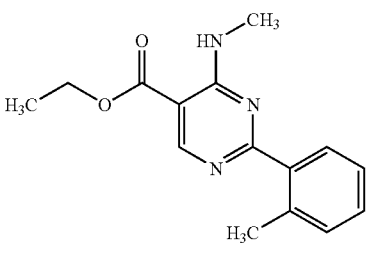 |
| 73 | 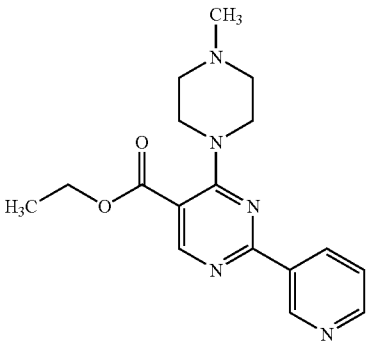 |

TABLE 2-continued
| Cmpd No. | Compound |
|---|---|
| 74 | 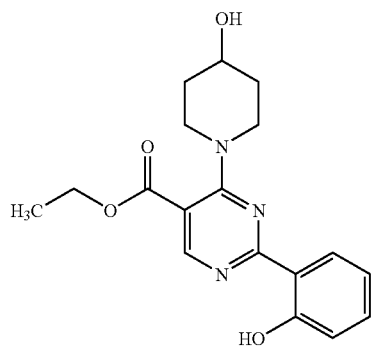 |
| 75 | 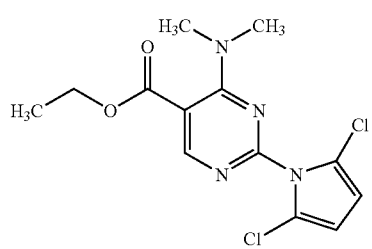 |
| 76 | 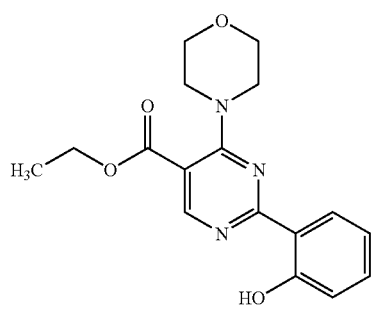 |
| 77 | 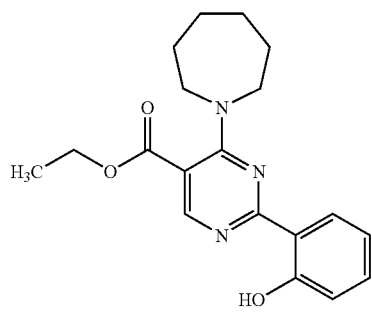 |
| 78 | 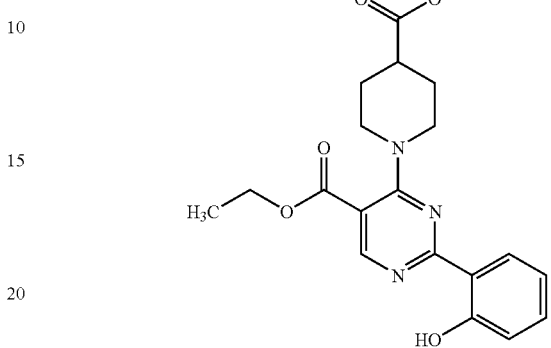 |
| 79 | 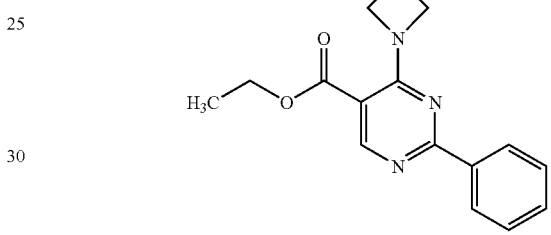 |
| 80 | 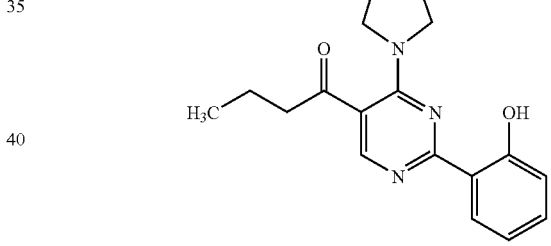 |
| 81 | 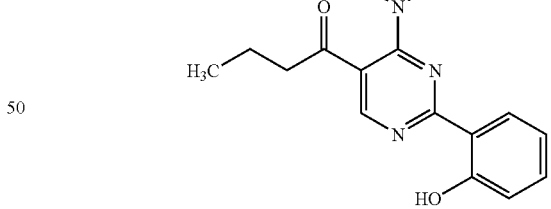 |
| 82 | 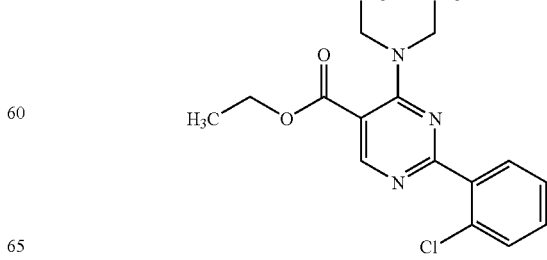 |

TABLE 2-continued

| Cmpd No. | Compound |
|---|---|
| 83 | |
| 84 | |
| 85 | |
| 86 | |
| 87 | |
| 88 | |
| 89 | |
| 90 | |
| 91 | |
| 92 | |

TABLE 2-continued

| Cmpd No. | Compound |
|---|---|
| 93 | ethyl 4-(4-methylpiperazin-1-yl)-2-(thiophen-2-yl)pyrimidine-5-carboxylate |
| 94 | ethyl 2-(2,3-difluorophenyl)-4-(dimethylamino)pyrimidine-5-carboxylate |
| 95 | ethyl 4-(2-methylpiperidin-1-yl)-2-(2-methylphenyl)pyrimidine-5-carboxylate |
| 96 | ethyl 2-(2-hydroxyphenyl)-4-[methyl(pentyl)amino]pyrimidine-5-carboxylate |
| 97 | ethyl 4-(piperidin-1-yl)-2-(pyridin-2-yl)pyrimidine-5-carboxylate |
| 98 | ethyl 2-(2-hydroxyphenyl)-4-(pyrrolidin-1-yl)pyrimidine-5-carboxylate |
| 99 | 4-(dimethylamino)-5-isobutyryl-2-(2-hydroxyphenyl)pyrimidine |
| 100 | ethyl 4-(dimethylamino)-2-(pyridin-4-yl)pyrimidine-5-carboxylate |
| 101 | ethyl 4-(dimethylamino)-2-(4-methoxyphenyl)pyrimidine-5-carboxylate |

TABLE 2-continued
| Cmpd No. | Compound |
|---|---|
| 102 | 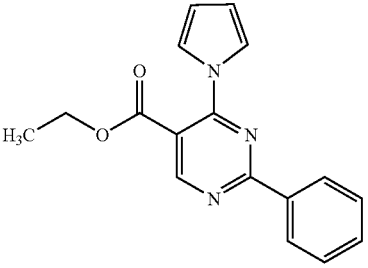 |
| 103 | 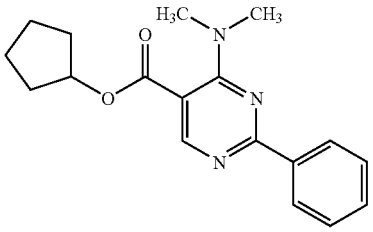 |
| 104 | 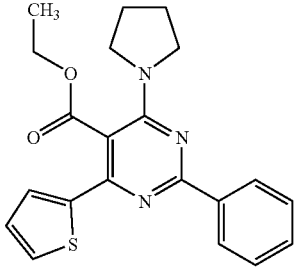 |
| 105 | 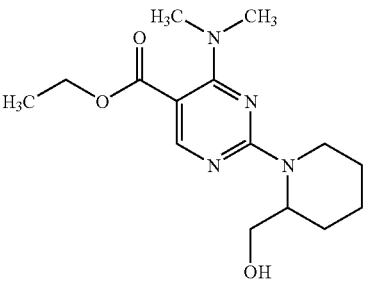 |
| 106 | 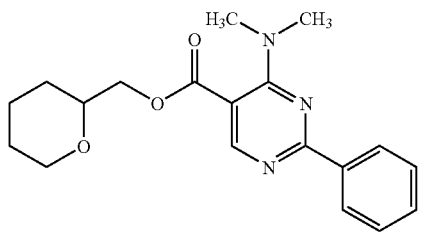 |
TABLE 2-continued
| Cmpd No. | Compound |
|---|---|
| 107 | 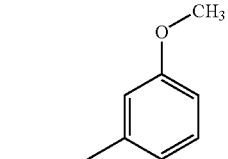 |
| 108 | 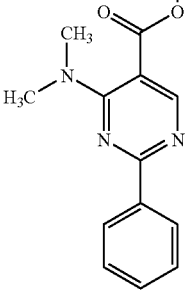 |
| 109 | 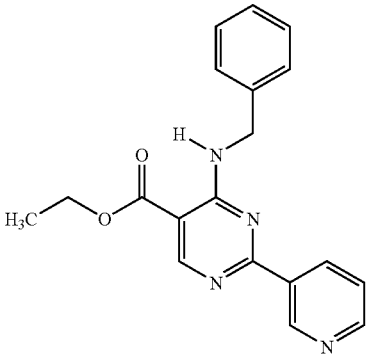 |
| 110 | 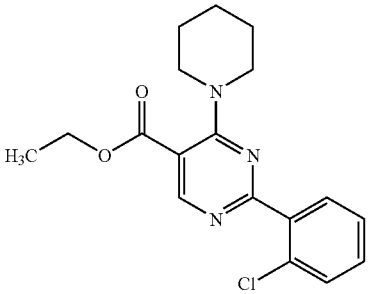 |

TABLE 2-continued

| Cmpd No. | Compound |
|---|---|
| 111 | ethyl 4-(dimethylamino)-2-(thiophen-2-yl)pyrimidine-5-carboxylate |
| 112 | ethyl 2-(3,5-bis(trifluoromethyl)phenyl)-4-(dimethylamino)pyrimidine-5-carboxylate |
| 113 | ethyl 2-(furan-2-yl)-4-(4-methylpiperazin-1-yl)pyrimidine-5-carboxylate |
| 114 | ethyl 4-(methylamino)-2-phenyl-6-(pyridin-4-yl)pyrimidine-5-carboxylate |
| 115 | ethyl 4-(dimethylamino)-2-(2-(trifluoromethyl)phenyl)pyrimidine-5-carboxylate |
| 116 | ethyl 2-(2-methoxyphenyl)-4-(2,5-dihydro-1H-pyrrol-1-yl)pyrimidine-5-carboxylate |
| 117 | ethyl 4-(dimethylamino)-2-(3-(ethoxycarbonyl)piperidin-1-yl)pyrimidine-5-carboxylate |
| 118 | ethyl 4-(dimethylamino)-2-(4-methylpiperazin-1-yl)pyrimidine-5-carboxylate |
| 119 | ethyl 2-(furan-2-yl)-4-(pyrrolidin-1-yl)pyrimidine-5-carboxylate |
| 120 | ethyl 2-(4-bromophenyl)-4-(methylamino)pyrimidine-5-carboxylate |

TABLE 2-continued

| Cmpd No. | Compound |
|---|---|
| 121 | |
| 122 | |
| 123 | |
| 124 | |
| 125 | |
| 126 | |
| 127 | |
| 128 | |
| 129 | |
| 130 | |
| 131 | |

TABLE 2-continued

| Cmpd No. | Compound |
|---|---|
| 132 | |
| 133 | |
| 134 | |
| 135 | |
| 136 | |

TABLE 2-continued

| Cmpd No. | Compound |
|---|---|
| 137 | |
| 138 | |
| 139 | |
| 140 | |
| 141 | |

TABLE 2-continued

| Cmpd No. | Compound |
|---|---|
| 142 | ethyl 4-(dimethylamino)-2-(3-cyanophenyl)pyrimidine-5-carboxylate |
| 143 | isopropyl 4-(dimethylamino)-2-phenylpyrimidine-5-carboxylate |
| 144 | 1-[4-(dimethylamino)-2-(2-hydroxyphenyl)pyrimidin-5-yl]pentan-1-one |
| 145 | ethyl 2-(2-chlorophenyl)-4-(2-methylpiperidin-1-yl)pyrimidine-5-carboxylate |
| 146 | 1-[4-(dimethylamino)-2-(2-methoxyphenyl)pyrimidin-5-yl]butan-1-one |
| 147 | ethyl 2-(4-tert-butylphenyl)-4-(dimethylamino)pyrimidine-5-carboxylate |
| 148 | butyl 4-(dimethylamino)-2-phenylpyrimidine-5-carboxylate |
| 149 | ethyl 4-(diethylamino)-2-(4-methylphenyl)pyrimidine-5-carboxylate |
| 150 | ethyl 2-(2-hydroxyphenyl)-4-(3-methylpiperidin-1-yl)pyrimidine-5-carboxylate |
| 151 | ethyl 2-(4-chlorophenyl)-4-(dimethylamino)pyrimidine-5-carboxylate |

TABLE 2-continued

| Cmpd No. | Compound |
|---|---|
| 152 | (structure) |
| 153 | (structure) |
| 154 | (structure) |
| 155 | (structure) |
| 156 | (structure) |
| 157 | (structure) |
| 158 | (structure) |
| 159 | (structure) |
| 160 | (structure) |
| 161 | (structure) |

TABLE 2-continued

| Cmpd No. | Compound |
|---|---|
| 162 | |
| 163 | |
| 164 | |
| 165 | |
| 166 | |

TABLE 2-continued

| Cmpd No. | Compound |
|---|---|
| 167 | |
| 168 | |
| 169 | |
| 170 | |
| 171 | |

TABLE 2-continued

| Cmpd No. | Compound |
|---|---|
| 172 | ethyl 4-(benzylamino)-6-methyl-2-phenylpyrimidine-5-carboxylate |
| 173 | ethyl 2-(2-chlorophenyl)-4-(pyrrolidin-1-yl)pyrimidine-5-carboxylate |
| 174 | ethyl 2-(3,5-dimethylphenyl)-4-(dimethylamino)pyrimidine-5-carboxylate |
| 175 | ethyl 4-(pyrrolidin-1-yl)-2-(pyridin-2-yl)pyrimidine-5-carboxylate |
| 176 | ethyl 2-(2-chlorophenyl)-4-(4-methylpiperazin-1-yl)pyrimidine-5-carboxylate |
| 177 | ethyl 4-(diethylamino)-2-(furan-2-yl)pyrimidine-5-carboxylate |
| 178 | ethyl 4-(diethylamino)-2-phenylpyrimidine-5-carboxylate |
| 179 | ethyl 4-(dimethylamino)-2-(3-(hydroxymethyl)piperidin-1-yl)pyrimidine-5-carboxylate |
| 180 | ethyl 2-(4-acetylphenyl)-4-(dimethylamino)pyrimidine-5-carboxylate |
| 181 | ethyl 4-((1-hydroxypropan-2-yl)amino)-2-phenylpyrimidine-5-carboxylate |

TABLE 2-continued

| Cmpd No. | Compound |
|---|---|
| 182 | ethyl 4-(dimethylamino)-2-(5-bromo-2-methoxyphenyl)pyrimidine-5-carboxylate |
| 183 | ethyl 4-(methylamino)-2-(pyridin-4-yl)pyrimidine-5-carboxylate |
| 184 | ethyl 4-(dimethylamino)-2-(pyridin-2-yl)pyrimidine-5-carboxylate |
| 185 | ethyl 4-(methylamino)-2-(thiophen-2-yl)pyrimidine-5-carboxylate |
| 186 | ethyl 4-(benzylamino)-2-(o-tolyl)pyrimidine-5-carboxylate |
| 187 | ethyl 4-(pyrazol-1-yl)-2-(2-hydroxyphenyl)pyrimidine-5-carboxylate |
| 188 | ethyl 4-(piperidin-1-yl)-2-(furan-2-yl)pyrimidine-5-carboxylate |
| 189 | ethyl 4-amino-2-(4-chlorophenyl)pyrimidine-5-carboxylate |
| 190 | ethyl 4-(pyrrolidin-1-yl)-6-(pyridin-4-yl)-2-phenylpyrimidine-5-carboxylate |
| 191 | ethyl 4-(dimethylamino)-2-(pyrrolidin-1-yl)pyrimidine-5-carboxylate |

TABLE 2-continued
| Cmpd No. | Compound |
|---|---|
| 192 | 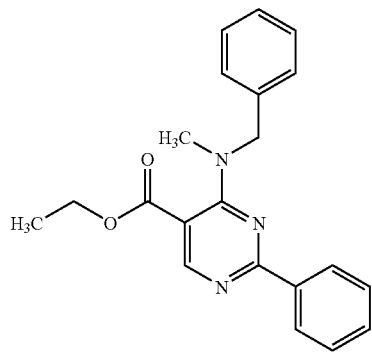 |
| 193 | 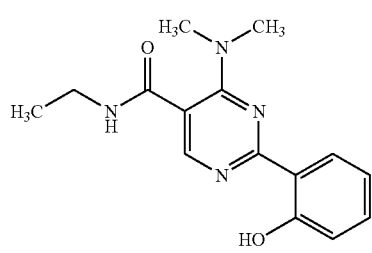 |
| 194 | 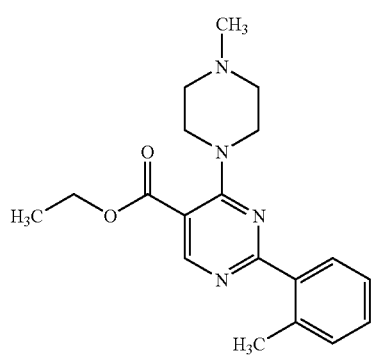 |
| 195 | 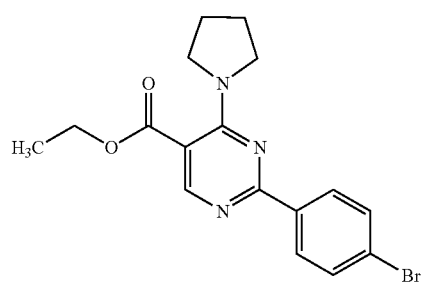 |
TABLE 2-continued
| Cmpd No. | Compound |
|---|---|
| 196 | 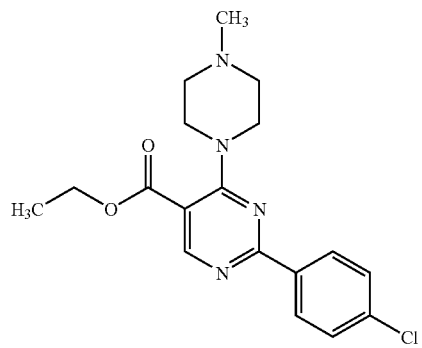 |
| 197 | 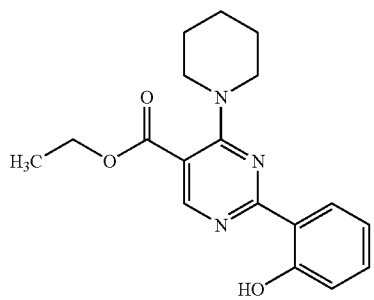 |
| 198 | 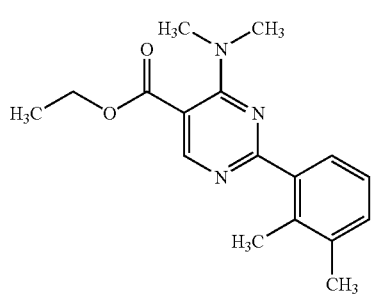 |
| 199 | 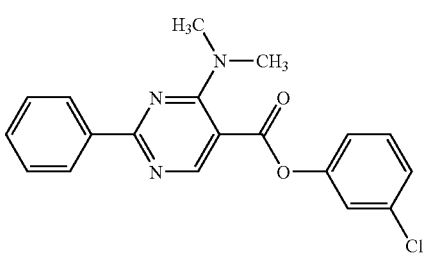 |
| 200 | 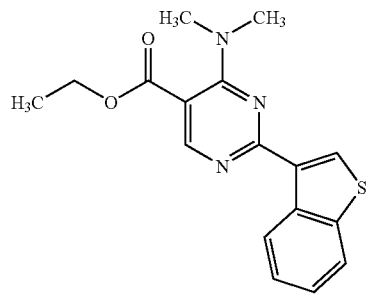 |

TABLE 2-continued

| Cmpd No. | Compound |
|---|---|
| 201 | ethyl 4-(dimethylamino)-6-(pyridin-4-yl)-2-phenylpyrimidine-5-carboxylate |
| 202 | ethyl 2-(4-bromophenyl)-4-(dimethylamino)pyrimidine-5-carboxylate |
| 203 | ethyl 2-(4-aminophenyl)-4-(dimethylamino)pyrimidine-5-carboxylate |
| 204 | ethyl 4-((2-(dimethylamino)ethyl)(methyl)amino)-2-(2-hydroxyphenyl)pyrimidine-5-carboxylate |
| 205 | ethyl 4-(3-hydroxypiperidin-1-yl)-2-phenylpyrimidine-5-carboxylate |
| 206 | ethyl 1-(4-(dimethylamino)-5-(ethoxycarbonyl)pyrimidin-2-yl)piperidine-4-carboxylate |
| 207 | methyl (S)-1-(5-(ethoxycarbonyl)-2-(2-methoxyphenyl)pyrimidin-4-yl)pyrrolidine-2-carboxylate |
| 208 | ethyl 2-(2-chlorophenyl)-4-(dimethylamino)pyrimidine-5-carboxylate |
| 209 | ethyl 4-(4-methylpiperazin-1-yl)-2-(pyridin-2-yl)pyrimidine-5-carboxylate |
| 210 | ethyl 4-(dimethylamino)-2-(1H-imidazol-1-yl)pyrimidine-5-carboxylate |

TABLE 2-continued
| Cmpd No. | Compound |
|---|---|
| 211 | 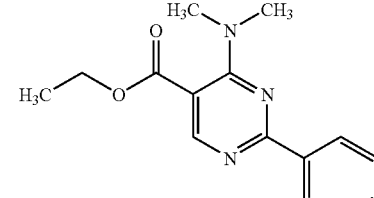 |
| 212 | |
| 213 | |
| 214 | |
| 215 | |
| 216 | 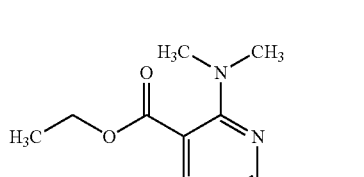 |
| 217 | |
| 218 | 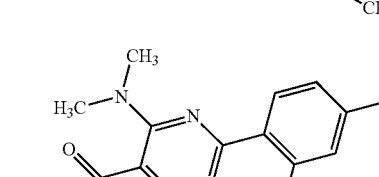 |
| 219 | 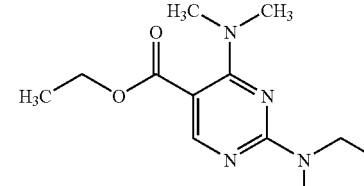 |
| 220 | 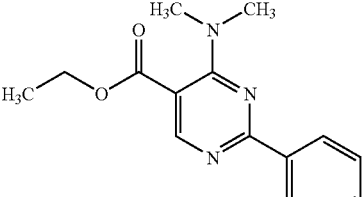 |

TABLE 2-continued

| Cmpd No. | Compound |
|---|---|
| 221 | |
| 222 | |
| 223 | |
| 224 | |
| 225 | |
| 226 | |
| 227 | |
| 228 | |
| 229 | |

TABLE 2-continued
| Cmpd No. | Compound |
|---|---|
| 230 | 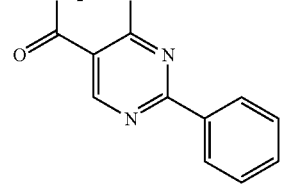 |
| 231 | |
| 232 | |
| 233 | |
| 234 | |
TABLE 2-continued
| Cmpd No. | Compound |
|---|---|
| 235 | 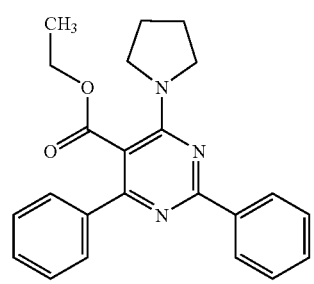 |
| 236 | |
| 237 | |
| 238 | |
| 239 | |

TABLE 2-continued

| Cmpd No. | Compound |
|---|---|
| 240 | |
| 241 | |
| 242 | |
| 243 | |
| 244 | |ыве

TABLE 2-continued

| Cmpd No. | Compound |
|---|---|
| 244 | |
| 246 | |
| 247 | |
| 248 | |
| 249 | |
| 250 | |

TABLE 2-continued

| Cmpd No. | Compound |
|---|---|
| 251 | |
| 252 | |
| 253 | |
| 254 | |
| 255 | |
| 256 | |
| 257 | |
| 258 | |
| 259 | |
| 260 | |
| 261 | |

TABLE 2-continued

| Cmpd No. | Compound |
|---|---|
| 262 | (structure) |
| 263 | (structure) |
| 264 | (structure) |
| 265 | (structure) |
| 266 | (structure) |
| 267 | (structure) |
| 268 | (structure) |
| 269 | (structure) |
| 270 | (structure) |
| 271 | (structure) |
| 272 | (structure) |
| 273 | (structure) |

TABLE 2-continued
| Cmpd No. | Compound |
|---|---|
| 274 | 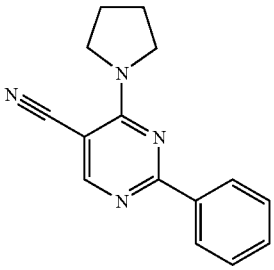 |
| 275 | 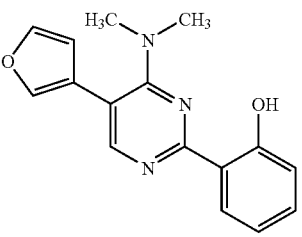 |
| 276 | 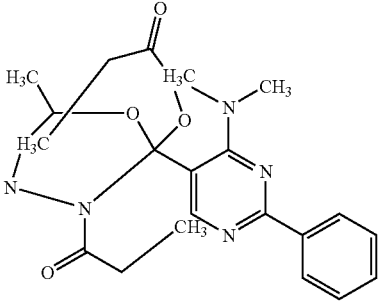 |
| 277 | 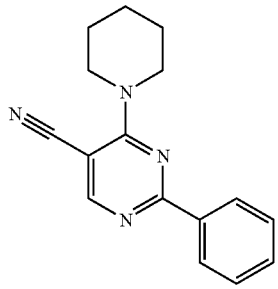 |
| 278 | 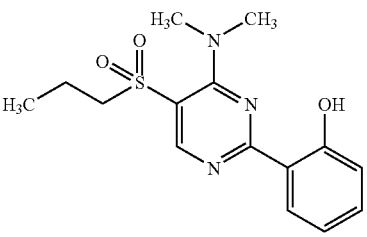 |
TABLE 2-continued
| Cmpd No. | Compound |
|---|---|
| 279 | 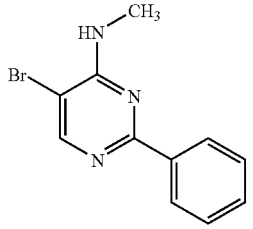 |
| 280 | 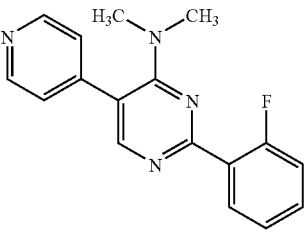 |
| 281 | 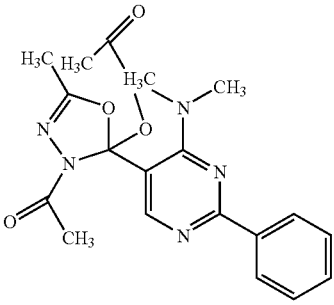 |
| 282 | 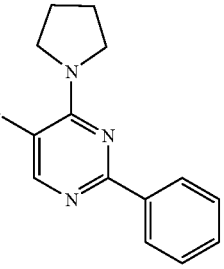 |
| 283 | 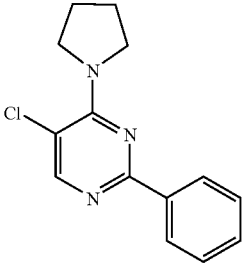 |

TABLE 2-continued

| Cmpd No. | Compound |
|---|---|
| 284 | |
| 285 | |
| 286 | |
| 287 | |
| 288 | |
| 289 | |
| 290 | |
| 291 | |
| 292 | |
| 293 | |
| 294 | |
| 295 | |

TABLE 2-continued

| Cmpd No. | Compound |
|---|---|
| 296 | 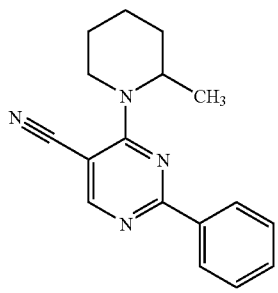 |
| 297 | 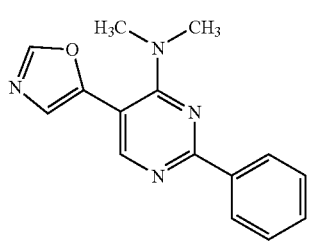 |
| 298 | 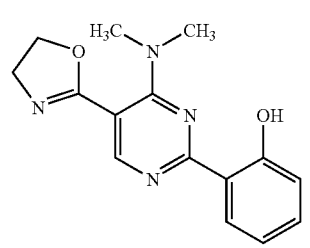 |
| 299 | 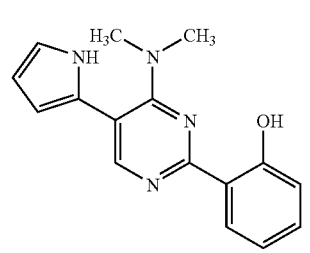 |
| 299 | 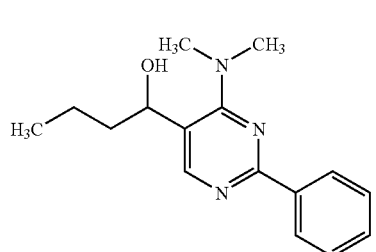 |
| 300 | 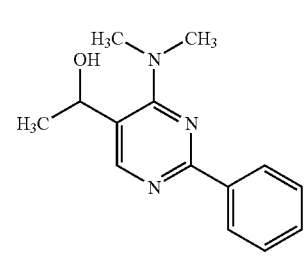 |

TABLE 2-continued

| Cmpd No. | Compound |
|---|---|
| 301 | 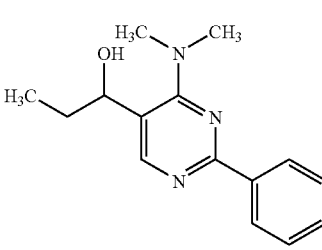 |
| 302 | 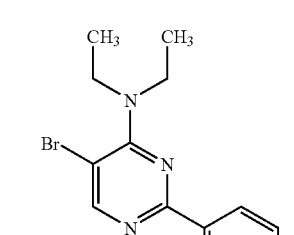 |
| 303 | 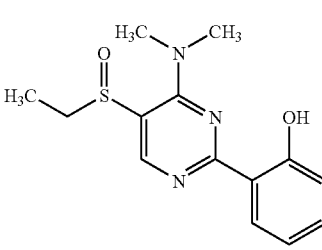 |
| 304 | |

4. General Synthetic Methodology:

The compounds of this invention may be prepared in general by methods known to those skilled in the art for analogous compounds, as illustrated by the general scheme below, and the preparative examples that follow.

Scheme I below depicts general conditions for the synthesis of compounds of formulas IB, IIB, IIIB via amidines and alkoxyalkylidine malonates.

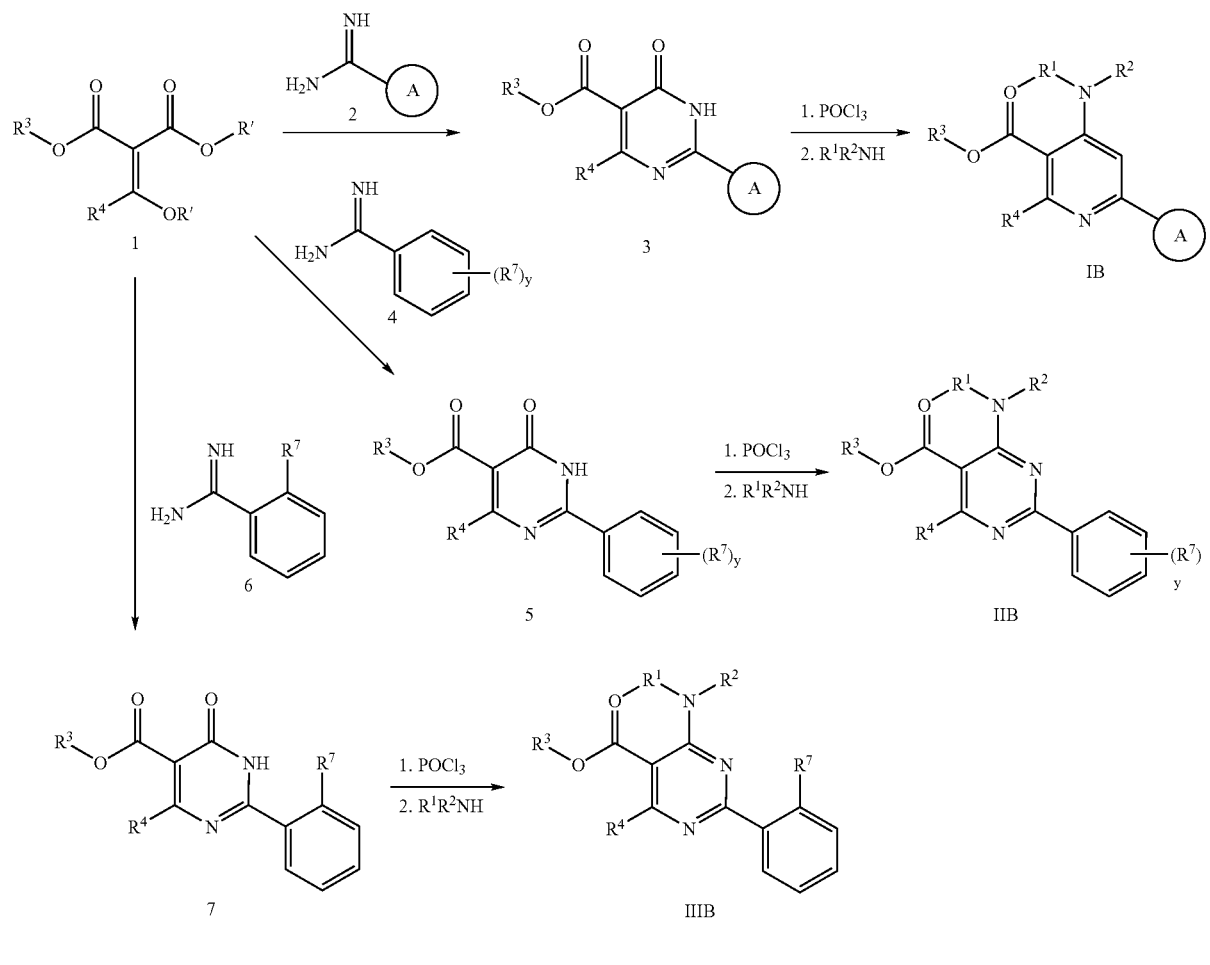

Scheme I:

Treatment of the appropriate alkoxyalkylidine malonate 1 (vide infra, Scheme III) with an amidine 2, 4, 6 (vide infra, Scheme II) generates the corresponding pyrimidinones 3, 5, 7. Subsequent chlorination and nucleophilic displacement with the amine R¹R²NH gives the pyrimidines IB, IIB, IIIB.

Scheme II below depicts synthesis of the requisite amidines 2, 4, 6 required for the preparation of IB, IIB, IIIB in the above Scheme I.

-continued

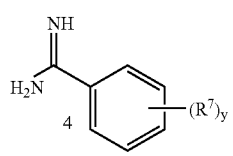

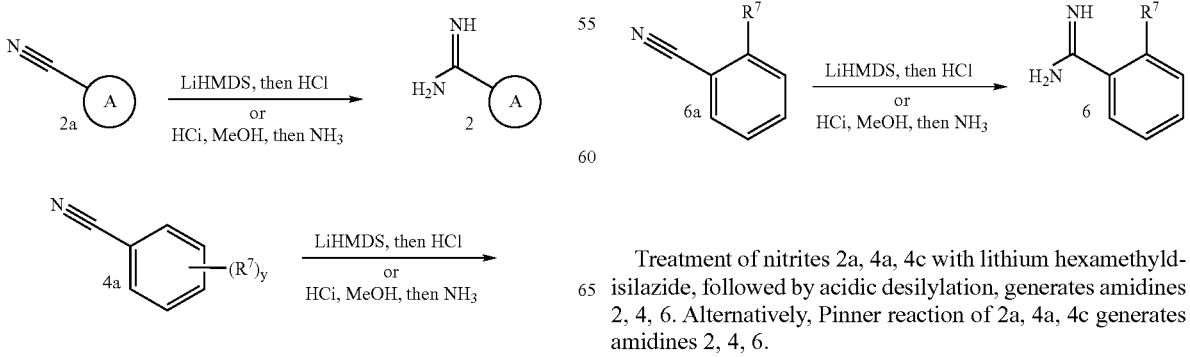

Scheme II:

Treatment of nitriles 2a, 4a, 4c with lithium hexamethyldisilazide, followed by acidic desilylation, generates amidines 2, 4, 6. Alternatively, Pinner reaction of 2a, 4a, 4c generates amidines 2, 4, 6.

Scheme III below depicts synthesis of the requisite alkoxyalkylidine malonates 1 required for the preparation of IB, IIB, IIIB in the above Scheme I.
Scheme III:
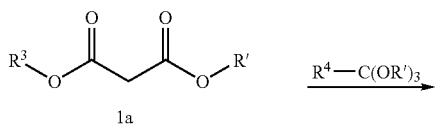
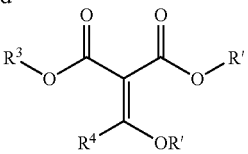
Treatment of malonates 1a with the appropriate orthoformate gives alkoxyalkylidine malonate 1.
Scheme IV below depicts synthesis of IB, IIB, IIIB via cross coupling reactions using C2 halopyrimidines.
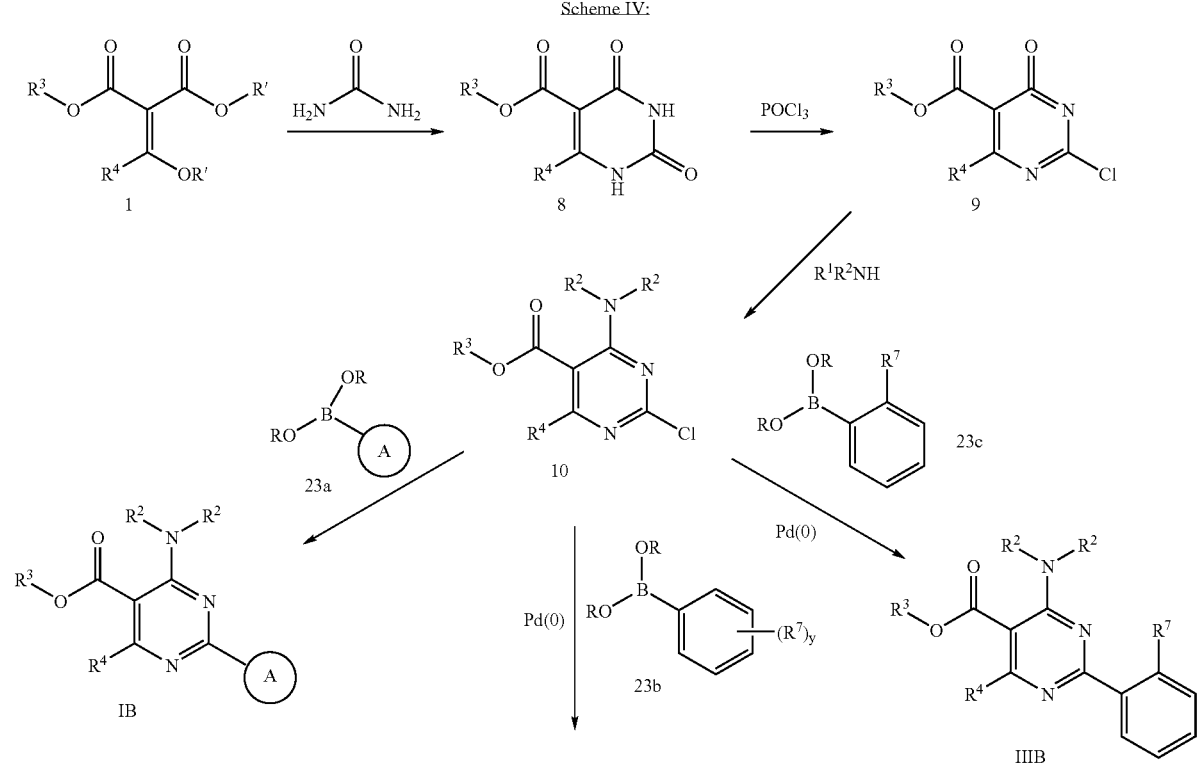
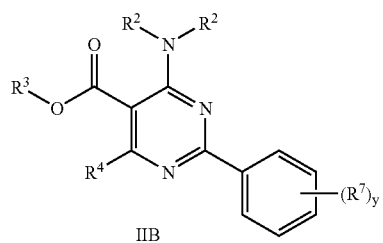

Treatment of alkoxyalkylidine malonate 1 with urea generates carboxyuracil 8, which is subsequently converted to dichloropyrimidine 9 with phosphorous oxychloride. Amination proceeds at position 4 to yield 2-chloropyrimidine 10, with Suzuki coupling at C2 giving the desired pyrimidines IB, IIB, IIIB.

Scheme V below depicts synthesis of C2 aza substituted pyrimidines using C2 halopyrimidines, via displacement at C2 of the pyrimidine with an incoming heteroatom nucleophile.

Scheme V:

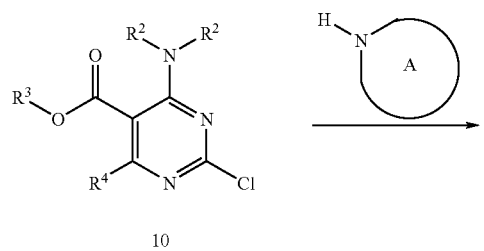

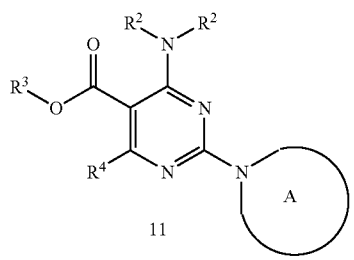

Treatment of chloropyrimidine 10 with the appropriate nucleophilic amine in the presence of a proton scavenger generates 11; in cases where the incoming amine is not sufficiently nucleophilic, generation of the amine anion with strong base such as sodium hydride followed by arylation with electrophile 10 gives 11.

Scheme VI below depicts synthesis of compounds IA using C5 halopyrimidines.

Scheme VI:

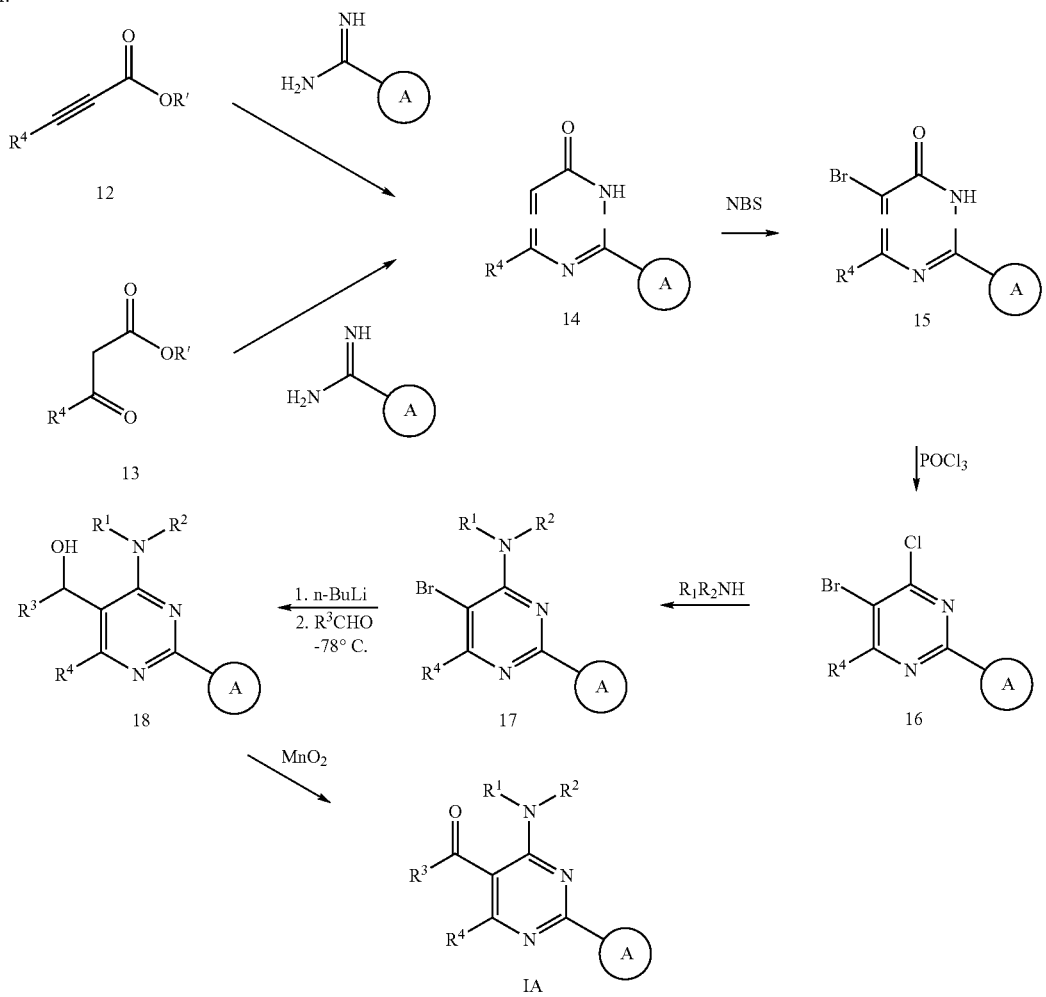

Treatment the appropriate alkynoate 12 or ketoester 13 with an amidine generates pyrimidinone 14, which undergoes electrophilic bromination at C5 to yield bromopyrimidinone 15. Chlorination with phosphorus oxychloride followed by displacement with a suitable amine gives 17. C5 metallation followed by reaction with an aldehyde yields hydroxypyrimidine 18, which can be readily oxidized by Mn(IV) to give IA.

Scheme VII below depicts synthesis of compounds IC, IIC, IIIC via a tandem Suzuki strategy.

Chlorination of bromouracil 19 affords dichlorobromopyrimidine 20, which undergoes amination at C4 by treatment with the appropriate amine $R^1R^2NH$. Suzuki cross coupling occurs at C5 to yield 2-chloropyrimidine 22, which is subsequently cross coupled with boronates 23a, 23b, 23c to give IC, IIC, IIIC.

Scheme VIII below depicts synthesis of C5 nitrile analogs of 26, 28, 30 using malononitriles 24.

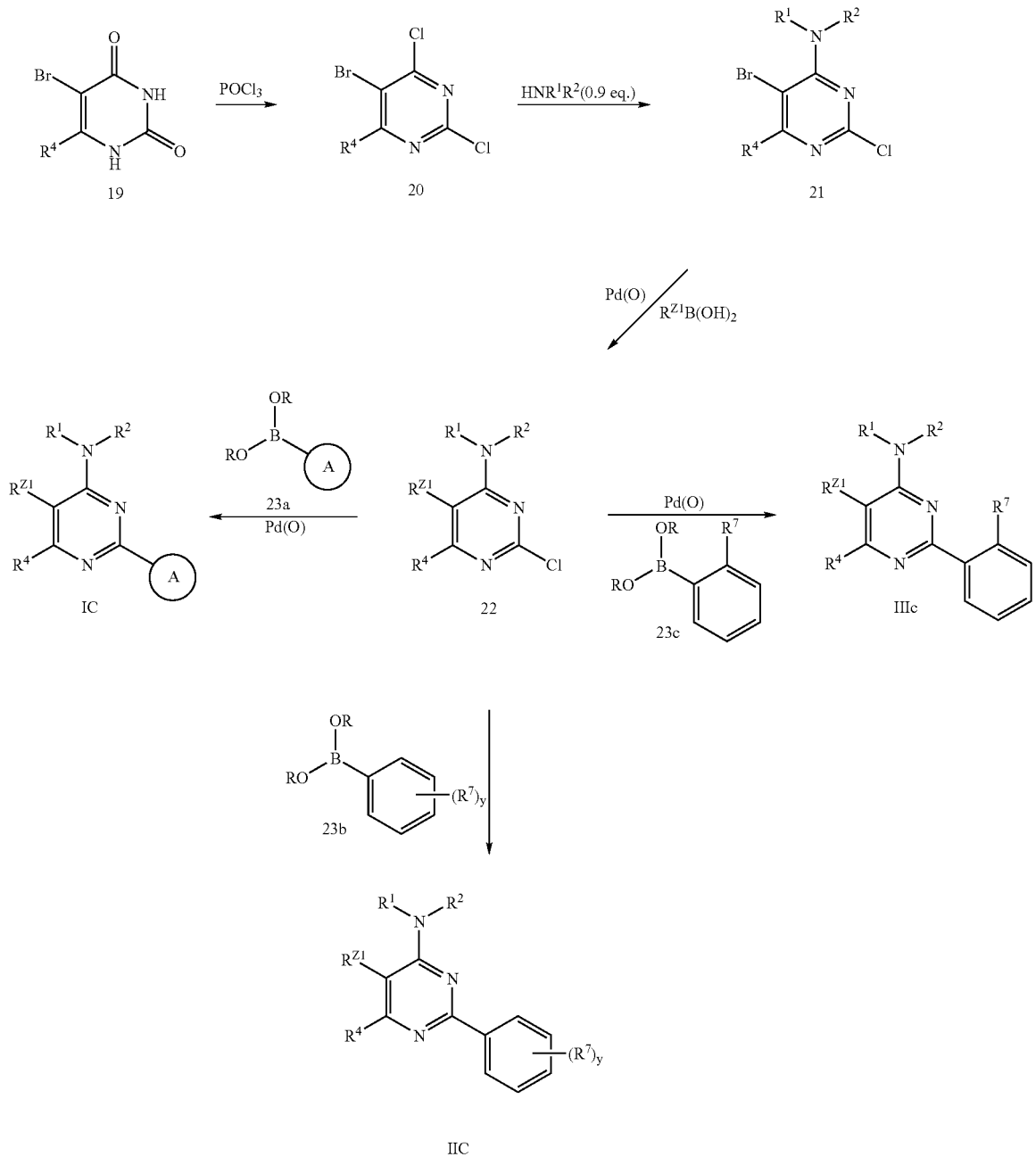

Scheme VII:

Scheme VIII:
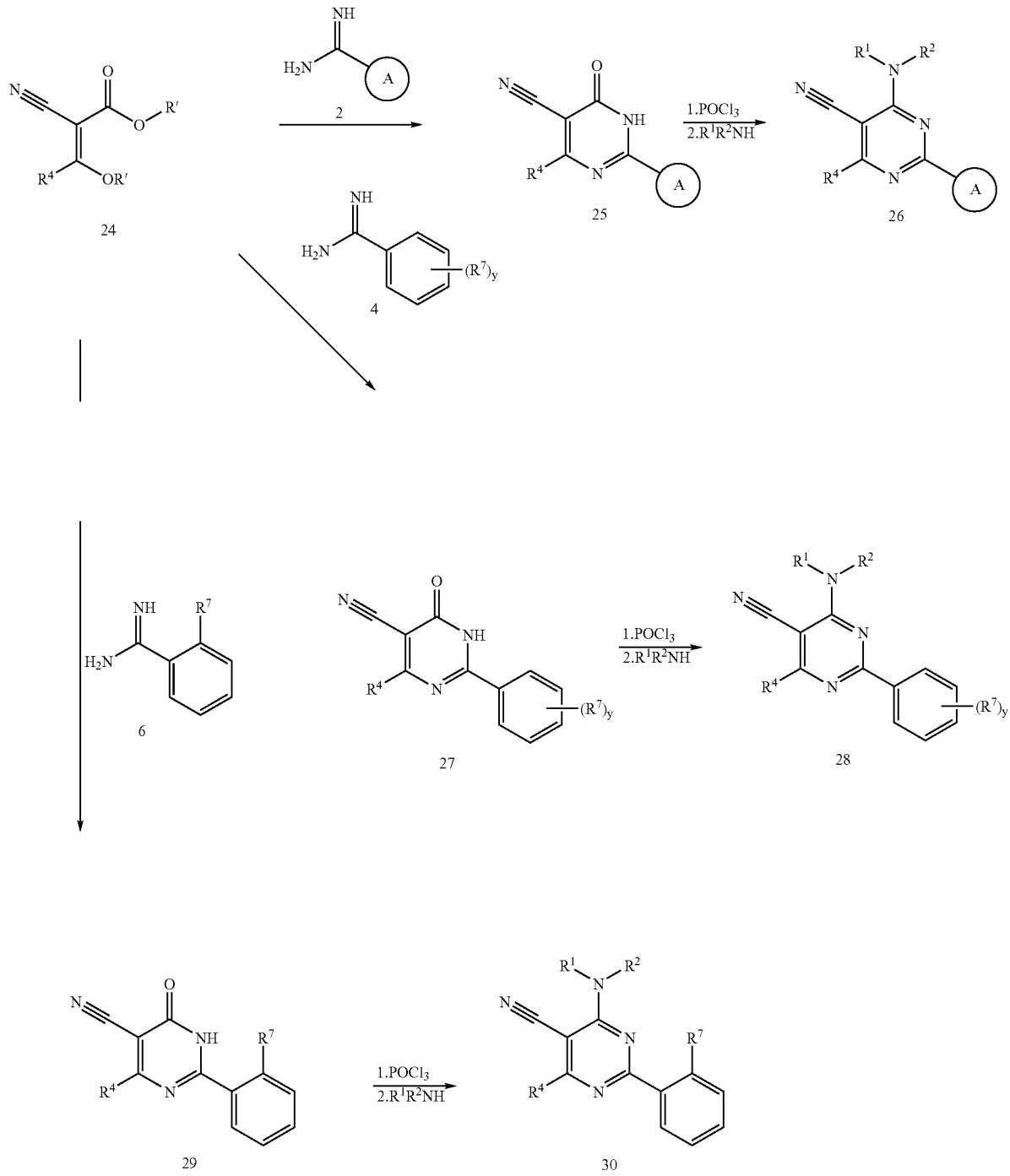

Treatment of alkoxyalkylidine malononitrile 24 with amidines 2, 4, 6 affords the 5-cyanopyrimidinones 25, 27, 29. Chlorination and amination at C4 by treatment with amine $R^1R^2NH$ gives the C5 cyano derivatives 26, 28, 30, which are themselves useful precursors to IC, IIC, IIIC.

Scheme IX depicts the preparation of IB derivatives 31, 32, 33, 34, which also facilitate synthesis of compounds IA.

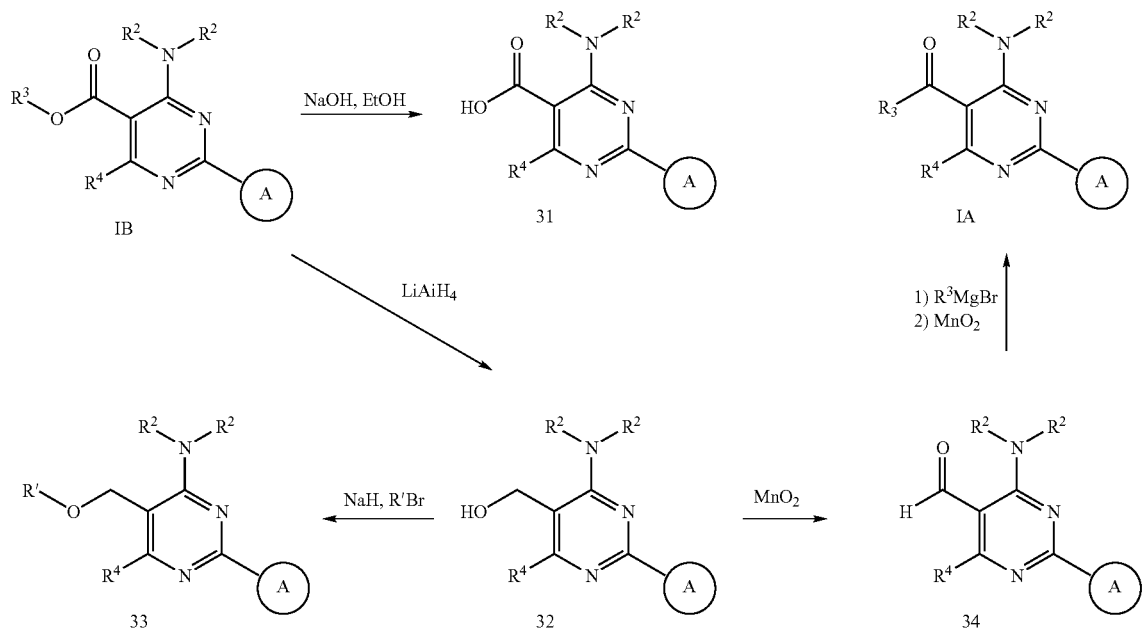

Scheme IX:

Saponification of IB affords C5 carboxylate 31 (vide infra, Scheme X); alternatively reduction using lithium aluminum hydride gives alcohol 32, which can either be derivatized using a Williamson ether synthesis or oxidized using Mn(IV) to give aldehyde 34. In addition to the formation of IA via Grignard addition and reoxidation, aldehyde 34 has utility as shown in Scheme X (vide infra).

Scheme X depicts the utility of carboxylate 31 in the preparation of C5 derivatives IC and IB, for example C5 derivatives 34 and C5 heteroaryl systems 33, 36, 37.

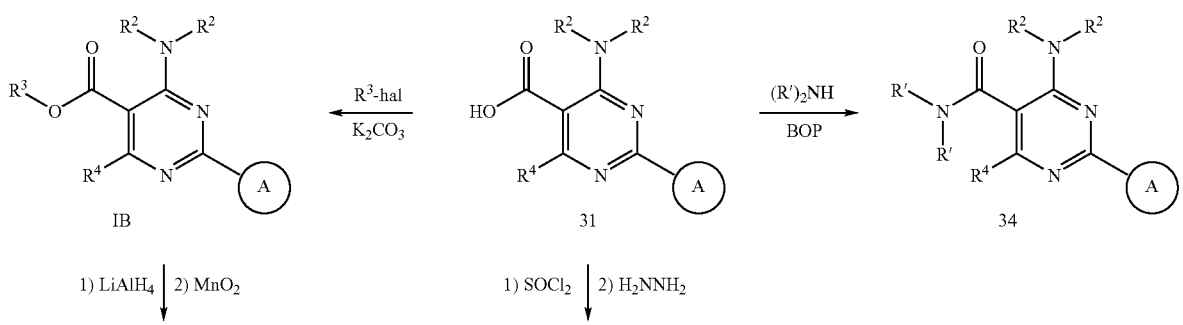

Scheme X:

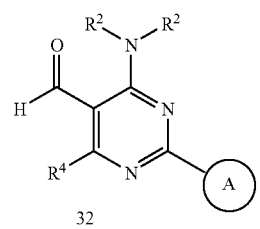

32

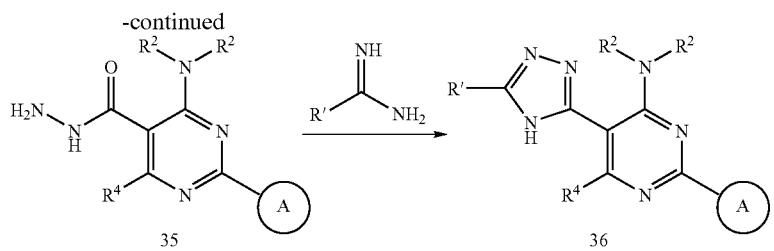

35  36

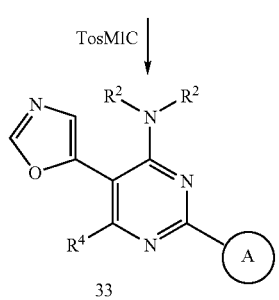

33

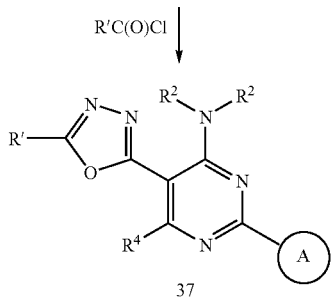

37

Alkylation of carboxylate 31 (vide supra, Scheme IX) yields IB, with subsequent conversion to aldehyde 32 and reaction with tosylmethylisocyanide yielding oxazoles 33. Alternatively, activation of the C5 carboxylate of 31 and reaction with a suitable nucleophile gives C5 amido derivatives 34, while reaction of the activated carboxylate with hydrazine affords hydrazide 35. Hydrazide 35 can be converted to a variety of heterocycles, for example triazoles 36 and oxadiazoles 37.

Sheme XI depicts further utility of nitrile 26 in the preparation of oxadiazoles.

Scheme XI:

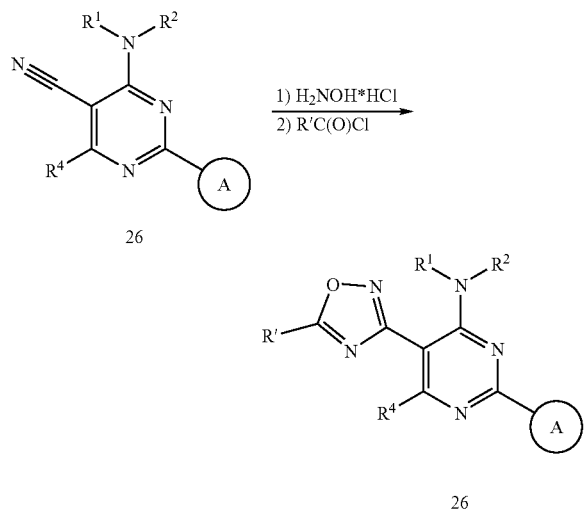

Treatment of nitrile 26 with hydroxylamine hydrochloride and subsequent acylation and cyclodehydration with an acyl chloride give 1,3,4-oxadiazoles.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, or incontinence is provided comprising administering an effective amount of a compound, or a pharmaceutically acceptable composition comprising a compound to a subject in need thereof. In certain preferred embodiments, a method for the treatment or lessening the severity of acute, chronic, neuropathic, or inflammatory pain is provided comprising administering an effective amount of a compound or a pharmaceutically acceptable composition to a subject in need thereof. In certain embodiments of the present invention an "effective amount" of the compound or pharmaceutically acceptable composition is that amount effective for treating or lessening the severity of one or more of acute, chronic, neuropathic, or inflammatory pain, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, or incontinence.

The compounds and compositions, according to the method of the present invention, may be administered using any amount and any route of administration effective for treating or lessening the severity of one or more of acute, chronic, neuropathic, or inflammatory pain, epilepsy or. epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, or incontinence. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the Examples herein, or according to methods available to one of ordinary skill in the art.

In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting NaV1.1, NaV1.2, NaV1.3, NaV1.4, NaV1.5, NaV1.6, NaV1.7, NaV1.8, NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLES

Example 1

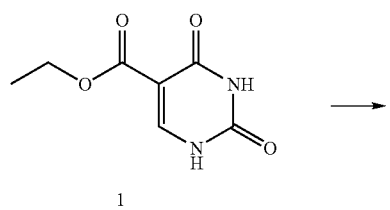

1

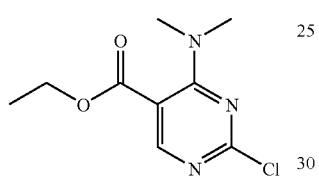

2

To a stirring suspension of 5-carbethoxyuracil 1 (3.00 g, 16.3 mmol) and phosphorus oxychloride (20 mL) in a 250 mL three-necked round-bottomed flask equipped with a magnetic stirrer and reflux condenser, was added N,N-dimethylaniline (2.10 mL, 16.3 mmol) in a single portion. The suspension was heated at reflux for 30 minutes and slowly formed a clear solution. The solution was concentrated under reduced pressure and the residue was poured onto ice (100 g). The solution was basified to pH=9.0 using concentrated aqueous sodium bicarbonate solution. The mixture was partitioned between $CH_2Cl_2$ and $H_2O$. The organic portion was dried ($MgSO_4$) and evaporated to dryness under reduced pressure. The residue was dissolved in anhydrous THF (30 mL) and cooled to 0° C. Dimethylaniline (16.3 mL, 32.6 mmol, 2.0 M in THF) was added dropwise, with stirring, over a period of 10 minutes. The solution was then stirred at 0° C. for 1 hour. The solution was concentrated under reduced pressure and the residue was purified by silica gel chromatography using (90% hexanes, 10% ethyl acetate) to obtain 2 (1.70 g, 7.34 mmol, 45% yield) as a yellow oil. M+1 (obs)=230.1; $R_t$=3.49.

2

-continued

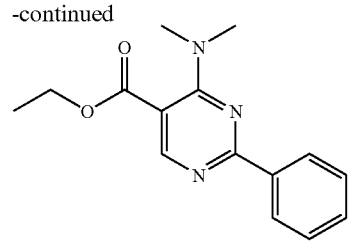

3

A 5 mL microwave reaction vessel was charged with a mixture of 2 (50 mg, 0.22 mmol), phenylboronic acid (39 mg, 0.32 mmol), tetrakis(triphenylphosphine)-palladium(0) (25 mg, 0.02 mmol), sodium carbonate (0.55 mL, 0.22 mmol, 0.40 M aqueous solution), and acetonitrile (0.55 mL). The vessel was sealed and heated, with stirring, at 150° C. for 10 minutes via microwave irradiation. The organic portion was concentrated under reduced pressure and the residue was purified by silica gel chromatography using (90% hexanes, 10% ethyl acetate) to obtain 3 (54 mg, 0.20 mmol, 92% yield) as a white solid. $^1$H NMR(CDCl$_3$) δ1.41 (t, 3H), 3.18 (s, 6H), 4.39 (q, 2H), 7.48-7.52 (m, 3H), 8.39-8.43 (m, 2H), 8.79 (s, 1H); M+1 (obs)=272.3; $R_t$=2.97.

4    5

To a stirring solution of 2-methoxybenzonitrile 4 (3.00 g, 22.5 mmol) and anhydrous $Et_2O$ (50 mL) in a 500 mL three-necked round-bottomed flask equipped with a magnetic stirrer was added lithium hexamethyldisilazane (45.0 mL, 45.0 mmol, 1.0 M in hexane) dropwise over 10 minutes, at 0° C. The solution was stirred at ambient temperature for 24 hours. 2.0 N aqueous HCl solution was carefully added dropwise over a 30 minute period at 0° C. The solution was stirred at ambient temperature for 2 hours. The aqueous portion was made strongly basic by the addition of saturated aqueous KOH solution (50 mL). The mixture was extracted with $CH_2Cl_2$ (5×40 mL). The organic portions were combined, dried ($MgSO_4$), and evaporated to dryness under reduced pressure to obtain 5 (1.20 g, 7.99 mmol, 36% yield) as a light tan solid. M+1 (obs)=151.2; $R_t$=0.85.

5

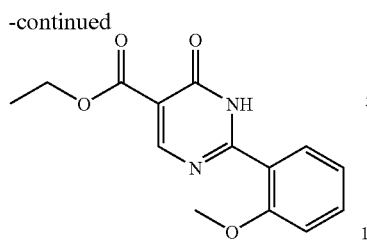

6

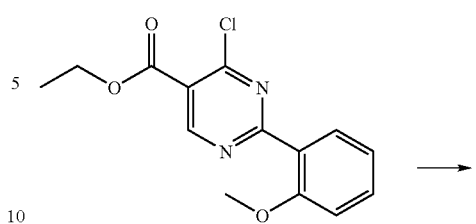

7

To a stirring solution of 2-methoxybenzamidine 5 (3.00 g, 20.0 mmol), diethyl ethoxymethylenemalonate (4.00 mL, 4.30 g, 20.0 mmol) and anhydrous EtOH (25 mL) in a 250 mL three-necked round-bottomed flask equipped with a magnetic stirrer was added sodium ethoxide (7.50 mL, 20.0 mmol, 21% in EtOH) dropwise over 10 minutes, at 0° C. The solution was stirred at ambient temperature for 1 hour. The mixture was poured into H$_2$O (50 mL) and the solution was acidified to pH=4 with conc. HCl. The mixture was partitioned between CH$_2$Cl$_2$ and H$_2$O. The organic portion was dried (MgSO$_4$) and evaporated to dryness under reduced pressure to obtain 6 (4.82 g, 17.6 mmol, 88% yield) as a white solid. M+1 (obs)=275.4; R$_t$=2.90.

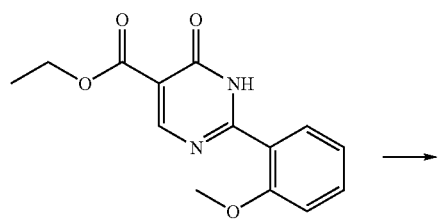

6

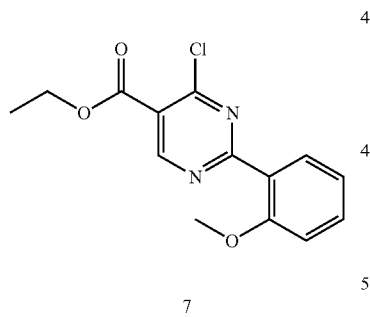

7

To a stirring suspension of 6 (4.50 g, 16.3 mmol) and phosphorus oxychloride (25 mL) in a 250 mL three-necked round-bottomed flask equipped with a magnetic stirrer and reflux condenser, was added N,N-dimethylaniline (2.10 mL, 16.3 mmol) in a single portion. The suspension was heated at reflux for 1 hour and slowly formed a clear solution. The solution was concentrated under reduced pressure and the residue was poured onto ice (100 g). The solution was basified to pH=9.0 using concentrated aqueous sodium bicarbonate solution. The mixture was partitioned between CH$_2$Cl$_2$ and H$_2$O. The organic portion was dried (MgSO$_4$) and evaporated to dryness under reduced pressure to obtain 7 (3.10 g, 10.6 mmol, 65% yield) as a white solid. M+1 (obs)=293.2; R$_t$=3.79.

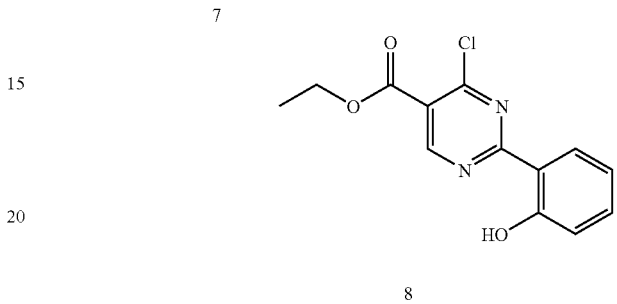

8

To a stirring solution of 7 (100 mg, 0.34 mmol) and CH$_2$Cl$_2$ (10 mL) in a 50 mL three-necked round-bottomed flask equipped with a magnetic stirrer was added boron tribromide (3.4 mL, 3.4 mmol, 1.0 M in CH$_2$Cl$_2$) dropwise over 10 minutes, at −78° C. The solution was stirred at −78° C. for 1 hour and then poured into a saturated aqueous solution of NaHCO$_3$ (20 mL). The organic portion was dried (MgSO$_4$) and evaporated to dryness under reduced pressure to obtain 8 (94 mg, 0.34 mmol, 100% yield) as a white solid. M+1 (obs)=279.1; R$_t$=4.50.

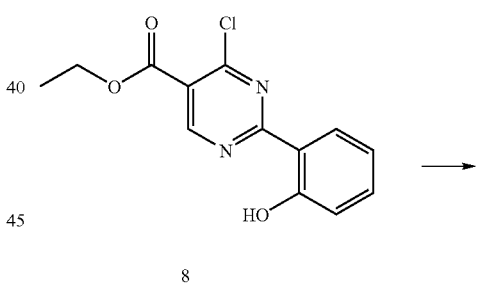

8

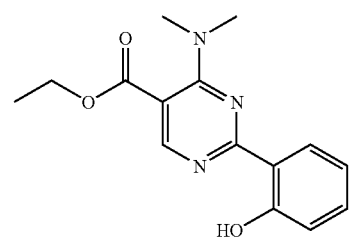

9

To a stirring solution of 9 (95 mg, 0.34 mmol), Et$_3$N (0.15 mL, 1.10 mmol), and THF (2.0 mL) in a 50 mL three-necked round-bottomed flask equipped with a magnetic stirrer was added dimethylaniline (0.55 mL, 1.10 mmol, 2.0 M in THF) dropwise, with stirring, over a period of 2 minutes. The solution was then stirred at ambient temperature for 1 hour. The solution was concentrated and purified by HPLC (10% to 99% CH₃CN) to obtain 9 as a trifluoroacetic acid salt (112 mg, 0.28 mmol, 82% yield) as a white solid. M+1 (obs)=288.0; R_t=3.47.

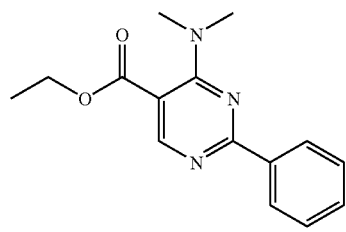

3

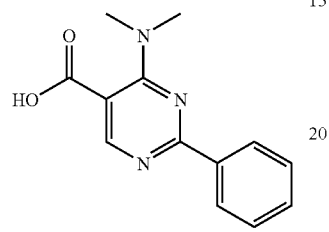

10

To a stirring solution of 3 (1.00 g, 3.70 mmol) and EtOH (50 mL) in a 250 mL three-necked round-bottomed flask equipped with a magnetic stirrer was added 1.0 N aqueuos NaOH solution (26.0 mL, 26.0 mmol). The solution was stirred at 70° C. for 2 hour. The solution was acidified to pH=4.0 using conc. HCl followed by basification with Et₃N. The mixture was concentrated under reduced pressure and the residue was purified by silica gel chromatography using (90% CH₂Cl₂, 10% MeOH) to obtain 10 (0.71 g, 2.90 mmol, 79% yield) as a white solid. M+1 (obs)=244.4; R_t=1.98.

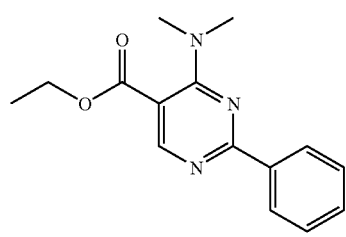

3

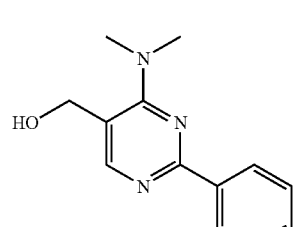

11

To a stirring solution of 3 (1.00 g, 3.70 mmol) and anhydrous THF (30 mL) in a 250 mL three-necked round-bottomed flask equipped with a magnetic stirrer was added lithium aluminum hydride (5.60 mL, 5.60 mmol, 1.0 M in THF) dropwise over a 10 minute period. The solution was stirred at room temperature for 20 minutes. To this solution was added H₂O (10 mL), at 0° C., over a 5 minute period. The mixture was partitioned between CH₂Cl₂ and H₂O. The organic portion was dried (MgSO₄) and evaporated to dryness under reduced pressure to obtain 11 (0.72 g, 3.15 mmol, 85% yield) as a white solid. M+1 (obs)=230.3; R_t=2.16.

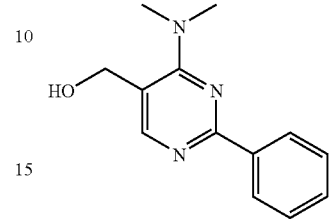

11

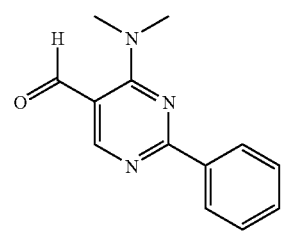

12

To a stirring solution of 11 (750 mg, 3.27 mmol) and CH₂Cl₂ (10 mL) in a 100 mL three-necked round-bottomed flask equipped with a magnetic stirrer was added manganese (IV) oxide (2.87 g, 33.0 mmol) in a single portion. The mixture was stirred at room temperature for 3 hours. The mixture was filtered through a bed of Celite® and the filtrate was evaporated to dryness under reduced pressure to obtain 12 (710 mg, 3.12 mmol, 96% yield) as a white solid. M+1 (obs)=228.2; R_t=3.42.

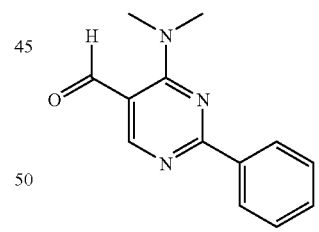

12

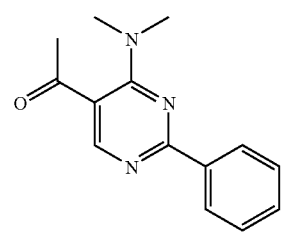

13

To a stirring solution of 12 (200 mg, 0.88 mmol) and Et₂O (15 mL) in a 100 mL three-necked round-bottomed flask equipped with a magnetic stirrer was added methylmagnesium bromide (0.60 mL, 1.76 mmol, 3.0 M in Et₂O) dropwise, at 0° C., over a 5 minute period. The mixture was stirred at room temperature for 30 minutes. The mixture was partitioned between EtOAc and H₂O. The organic portion was dried (MgSO₄) and evaporated to dryness under reduced pressure. The obtained residue was dissolved in CH₂Cl₂ (10 mL). Manganese(IV) oxide (2.87 g, 33.0 mmol) was added in a single portion and the mixture was stirred at room temperature for 3 hours. The mixture was filtered through a bed of Celite® and the filtrate evaporated to dryness under reduced pressure. The residue was purified by HPLC (10% CH₃CN) to obtain 13 as a trifluoroacetic acid salt (196 mg, 0.55 mmol, 63% yield) as a white solid. M+1 (obs)=242.1; R$_t$=2.95.

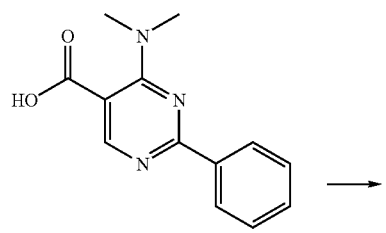

10

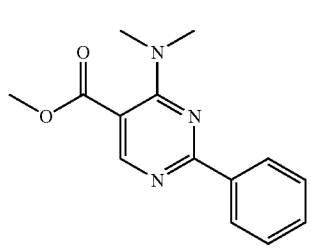

14

To a stirring solution of 10 (100 mg, 0.41 mmol), potassium carbonate (170 mg, 1.23 mmol) and anhydrous DMF (0.50 mL) in a 1 mL single-necked reaction vessel equipped with a stirrer was added iodomethane (0.05 mL, 0.82 mmol) in a single portion. The mixture was stirred at room temperature for 2 hours. The mixture was filtered and the filtrate purified by HPLC (10% to 99% CH₃CN) to obtain 14 as a trifluoroacetic acid salt (111 mg, 0.30 mmol, 72% yield) as a white solid. M+1 (obs)=258.2; R$_t$=2.44.

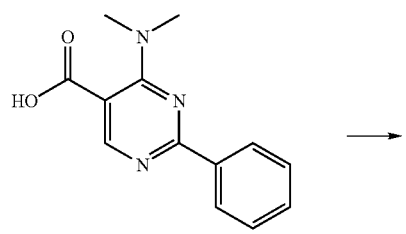

10

-continued

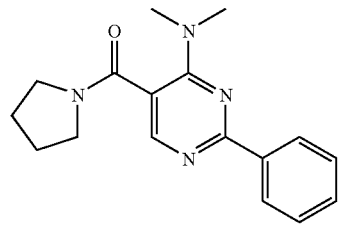

15

To a stirring solution of 10 (100 mg, 0.41 mmol), pyrrolidine (29 mg, 0.41 mmol), Et₃N (83 mg, 0.82 mmol), and anhydrous DMF (1.0 mL) in a 1 mL single-necked reaction vessel equipped with a magnetic stirrer was added benzotriazol-1-yloxy-tris(dimethylamino)phosphonium hexafluorophosphate (181 mg, 0.41 mmol) in a single portion. The mixture was stirred at room temperature for 20 minutes. The mixture was filtered and the filtrate purified by HPLC (10% to 99% CH₃CN) to obtain 15 as a trifluoroacetic acid salt (135 mg, 0.33 mmol, 81% yield) as a white solid. M+1 (obs)=297.4; R$_t$=2.23.

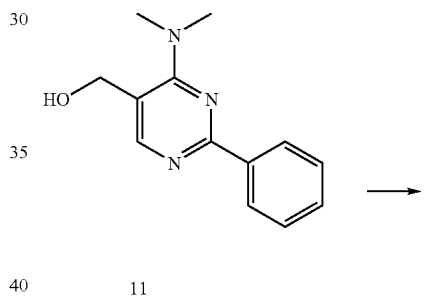

11

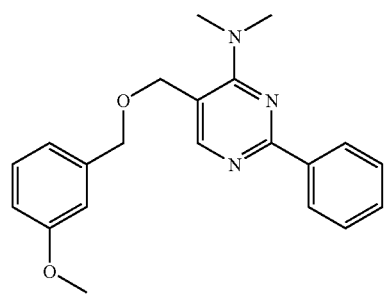

16

To a stirring solution of 11 (50 mg, 0.22 mmol) and anhydrous DMF (0.50 mL) in a 1 mL single-necked reaction vessel equipped with a magnetic stirrer was added sodium hydride (9.0 mg, 0.22 mmol, 60% in mineral oil) in a single portion. The mixture was stirred at room temperature for 15 minutes. To this solution was added 3-methoxybenzyl bromide (66 mg, 0.33 mmol) in a single portion. The mixture was filtered and the filtrate purified by HPLC (10% to 99% CH₃CN) to obtain 16 as a trifluoroacetic acid salt (65 mg, 0.14 mmol, 63% yield) as a white solid. M+1 (obs)=350.4; R$_t$=3.06.

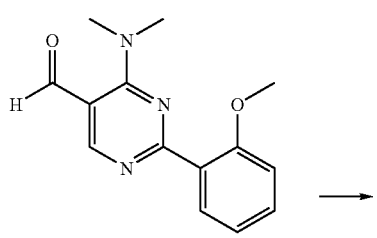

17

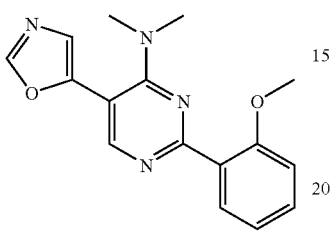

18

To a stirring solution of 17 (100 mg, 0.39 mmol) and anhydrous MeOH (0.50 mL) in a 1 mL single-necked reaction vessel equipped with a magnetic stirrer was added potassium carbonate (180 mg, 1.30 mmol) in a single portion. The mixture was stirred at room temperature for 5 minutes. Tosylmethyl isocyanide (91 mg, 0.47 mmol) was added in a single portion and the mixture was heated at 60° C. for 17 hours. The solution was concentrated under reduced pressure and the residue was purified by silica gel chromatography using (97% CH$_2$Cl$_2$, 3% MeOH) to obtain 18 (105 mg, 0.35 mmol, 90% yield) as a white solid. M+1 (obs)=297.2; R$_f$=2.83.

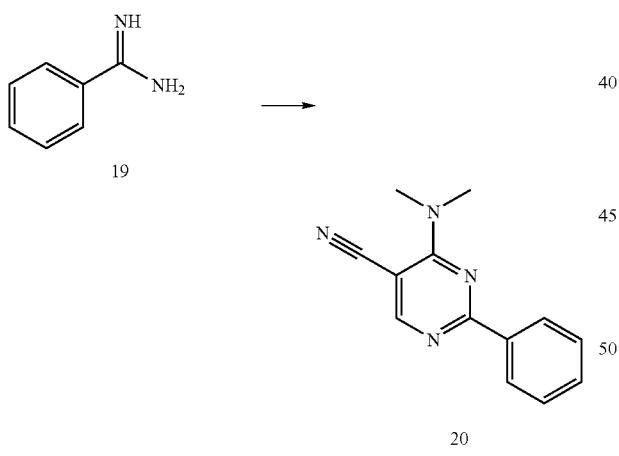

To a stirring solution of benzamidine hydrochloride 19 (735 mg, 4.70 mmol), diethyl ethoxymethylenemalonate (794 mg, 4.70 mmol) and anhydrous EtOH (10 mL) in a 100 mL three-necked round-bottomed flask equipped with a magnetic stirrer was added sodium ethoxide (3.50 mL, 9.41 mmol, 21% in EtOH) dropwise over 10 minutes, at 0° C. The solution was heated at reflux for 1 hour. The mixture was poured into H$_2$O (25 ml) and the solution was acidified to pH=3 with conc. HCl. The precipitate was filtered and the residual solid was vacuum dried to obtain the intermediate pyrimidinone as a white solid (500 mg, 2.54 mmol). The obtained pyrimidinone was suspended in phosphorus oxychloride (3 mL) in a 50 mL three-necked round-bottomed flask equipped with a magnetic stirrer and reflux condenser. To this suspension was added dimethylaniline (0.32 mL, 2.54 mmol) in a single portion. The suspension was heated at reflux for 1 hour and slowly formed a clear solution. The solution was concentrated under reduced pressure and the residue was poured onto ice (100 g). The solution was basified to pH=9.0 using concentrated aqueous sodium bicarbonate solution. The mixture was partitioned between CH$_2$Cl$_2$ and H$_2$O. The organic portion was dried (MgSO$_4$) and evaporated to dryness under reduced pressure. To the obtained residue was added Et$_3$N (0.35 mL, 2.54 mmol), and THF (2.0 mL) in a 50 mL three-necked round-bottomed flask equipped with a magnetic stirrer. To this solution was added dimethylaniline (3.81 mL, 7.62 mmol, 2.0 M in THF) dropwise, with stirring, over a period of 2 minutes. The solution was then stirred at ambient temperature for 1 hour. The solution was concentrated under reduced pressure and the residue was purified by silica gel chromatography using (80% hexanes, 20% ethyl acetate) to obtain 20 (256 mg, 1.14 mmol, 24% yield) as a clear oil. M+1 (obs)=225.1; R$_f$=3.83.

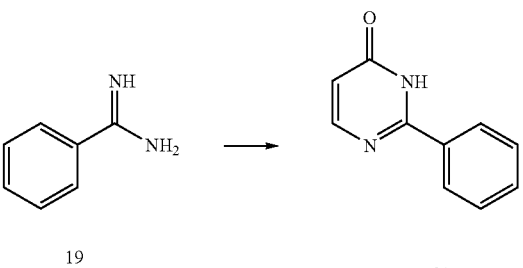

19                          21

To a stirring solution of benzamidine hydrochloride 19 (5.00 g, 31.9 mmol), ethyl propiolate (3.50 mL, 34.3 mol) and anhydrous EtOH (50 mL) in a 250 mL three-necked round-bottomed flask equipped with a magnetic stirrer was added sodium ethoxide (6.51 mL, 63.8 mmol, 21% in EtOH) dropwise over 10 minutes, at 0° C. The solution was heated at reflux for 2.5 hour. The mixture was poured into H$_2$O (25 mL) and the solution was acidified to pH=3 with conc. HCl. The precipitate was filtered and the residual solid was vacuum dried to obtain 21 (2.9 g, 16.8 mmol, 53% yield) as a white solid. M+1 (obs)=173.20; R$_f$=1.74.

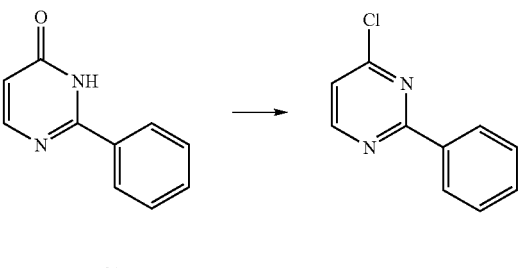

21                          22

A stirring suspension of 21 (2.50 g, 14.5 mmol) and phosphorus oxychloride (17 mL) in a 100 mL three-necked round-bottomed flask equipped with a magnetic stirrer and reflux condenser, was heated at reflux for 3 hours and slowly formed a clear solution. The solution was concentrated under reduced pressure and the residue was poured onto ice (40 g). The obtain precipitate was filtered, washed with water, and vacuum dried to give 22 (2.10 g, 11.0 mmol, 76% yield) as a white solid. M+1 (obs)=191.0; $R_t$=4.22.

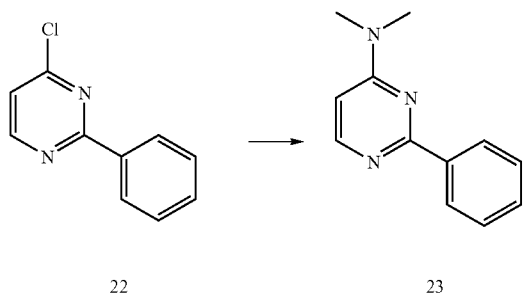

22    23

To a stirring solution of 22 (150 mg, 0.80 mmol) and $H_2O$ (1.5 mL) in a 5 mL microwave vessel was added dimethylaniline (1.50 mL, 3.00 mmol, 2.0 M in MeOH). The solution was then heated via microwave irradiation to 150° C. for 5 minutes. The solution was purified by HPLC (10% to 99% $CH_3CN$) to obtain 23 as a trifluoroacetic acid salt (130 mg, 0.28 mmol, 52% yield) as a white solid. M+1 (obs)=200.2; $R_t$=2.32.

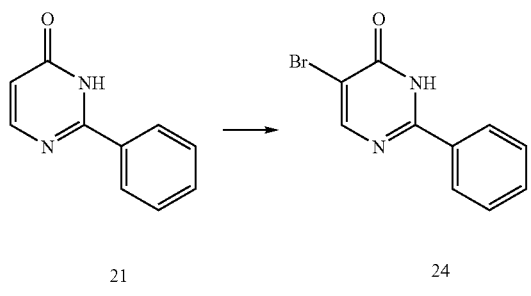

21    24

To a stirring solution of 21 (100 mg, 0.58 mmol) and acetic acid (2.0 ml) in a 50 mL three-necked round-bottomed flask equipped with a magnetic stirrer and reflux condenser, was added N-bromosuccinimide (103 mg, 0.58 mmol). The mixture was heated at 60° C. for 1 hour. The solution was concentrated under reduced pressure and the residue was purified by silica gel chromatography using (97% $CH_2Cl_2$, 3% MeOH) to obtain 24 (110 mg, 0.44 mmol, 76% yield) as a white solid. $^1$H NMR(DMSO-$D_6$) δ 7.44-7.61 (m, 3H), 8.04-8.16 (m, 2H), 8.44 (s, 1H) 13.23 (s, 1H); M+1 (obs)=251.1; $R_t$=2.98.

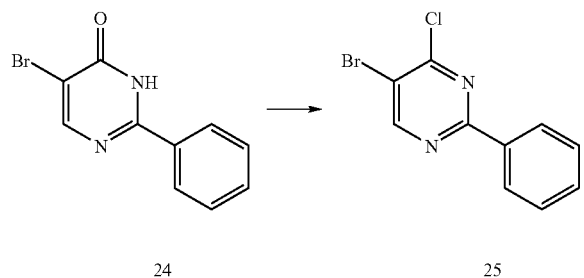

24    25

A stirring suspension of 24 (100 mg, 0.40 mmol) and phosphorus oxychloride (2.0 mL) in a 50 mL three-necked round-bottomed flask equipped with a magnetic stirrer and reflux condenser, was heated at reflux for 1 hour and slowly formed a clear solution. The solution was concentrated under reduced pressure and the residue was poured onto ice (10 g). The solution was basified to pH=9.0 using concentrated aqueous sodium bicarbonate solution. The mixture was partitioned between $CH_2Cl_2$ and $H_2O$. The organic portion was dried ($MgSO_4$) and evaporated to dryness under reduced pressure to obtain 25 (95 mg, 0.035 mmol, 88% yield) as a white solid. M+1 (obs)=271.0; $R_t$=4.67.

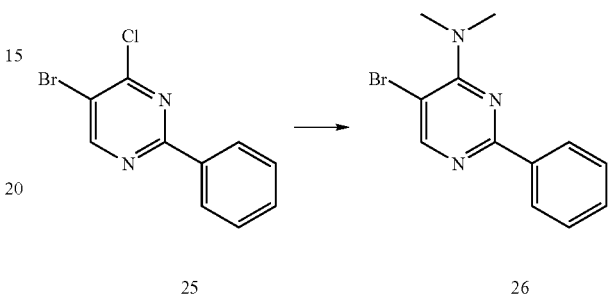

25    26

To a stirring solution of 25 (80 mg, 0.30 mmol) $Et_3N$ (0.10 mL, 0.70 mL) and THF (2.0 mL) in a 1 mL reaction vessel was added dimethylaniline (1.0 mL, 2.0 mmol, 2.0 M in THF). The solution was stirred at room temperature for 15 minutes. The solution was purified by HPLC (10% to 99% $CH_3CN$) to obtain 26 as a trifluoroacetic acid salt (94 mg, 0.24 mmol, 79% yield) as a white solid. M+1 (obs)=277.8; $R_t$=3.23.

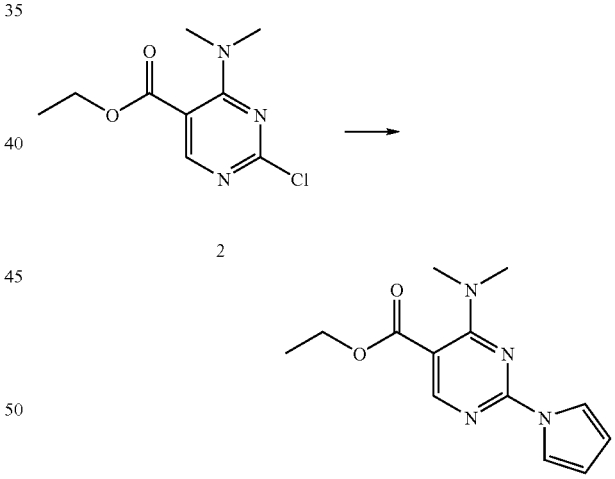

2

27

To a stirring solution of pyrrole (23 mg, 0.33 mmol) and anhydrous THF (0.50 mL) in a 2 mL microwave vessel was added sodium hydride (5.0 mg, 0.12 mmol, 60% in mineral oil). The mixture was stirred at ambient temperature for 10 minutes. To this solution was added 2 (25 mg, 0.11 mmol). The solution was then heated via microwave to 150° C. for 5 minutes. The solution was purified by HPLC (10% to 99% $CH_3CN$) to obtain 27 as a trifluoroacetic acid salt (30 mg, 0.08 mmol, 74% yield) as a white solid. M+1 (obs)=261.0; $R_t$=4.28.

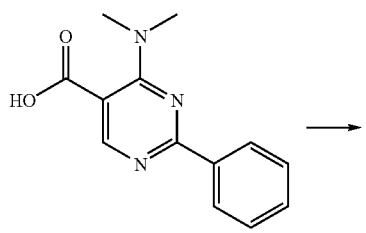

10

To a stirring solution of 10 (500 mg, 1.84 mmol), thionyl chloride (1.50 mL) and benzene (10 mL) in a 100 mL three-necked round-bottomed flask equipped with a magnetic stirrer and reflux condenser, was added a single drop of DMF. The solution was heated at reflux for 2 hours. The solution was concentrated under reduced pressure and the residue was azeotroped with toluene (2×10 mL). The residue was dissolved in CH$_2$Cl$_2$ (10 mL) follwed by the addition of Et$_3$N (0.50 mL, 3.60 mmol) and hydrazine (0.11 mL, 3.6 mmol). The solution was stirred at ambient temperature for 30 minutes. The mixture was evaporated to dryness under reduced pressure. The residue was purified by silica gel chromatography using (90% CH$_2$Cl$_2$, 10% MeOH) to obtain 28 (350 mg, 1.36 mmol, 74% yield) as a white solid. M+1 (obs)=258.0; R$_t$=1.66.

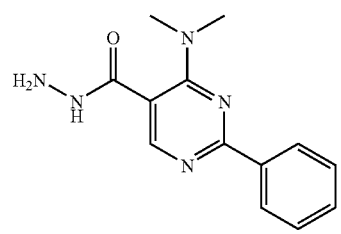

28

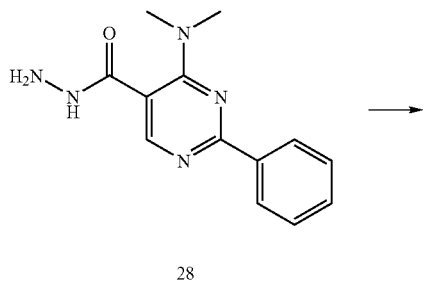

29

To a stirring solution of 28 (20 mg, 0.13 mmol), Et$_3$N (0.05 mL, 0.39 mmol), and CH$_2$Cl$_2$ (3.0 mL)) in a 50 mL three-necked round-bottomed flask equipped with a magnetic stirrer, was added propionyl chloride (0.02 mL, 0.26 mmol). The solution was stirred at ambient temperature for 30 minutes. The mixture was partitioned between CH$_2$Cl$_2$ and H$_2$O. The organic portion was dried (MgSO$_4$) and evaporated to dryness under reduced pressure. The residue was dissolved in anhydrous CH$_3$CN (2 mL) followed by the addition of POCl$_3$ (0.06 mL, 0.65 mmol). The solution was heated via microwave to 170° C. for 5 minutes in a 5 mL microwave vessel. The solution was purified by HPLC (10% to 99% CH$_3$CN) to obtain 29 as a trifluoroacetic acid salt (33 mg, 0.08 mmol, 59% yield) as a white solid. M+1 (obs)=296.4; R$_t$=3.18.

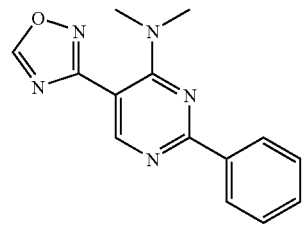

20

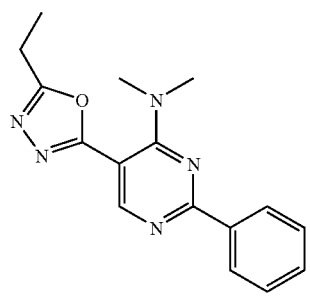

30

To a stirring solution of 20 (100 mg, 0.41 mmol), hydroxylamine hydrochloride (68 mg, 0.98 mmol) and anhydrous EtOH (0.50 mL) in a 10 mL three-necked round-bottomed flask equipped with a magnetic stirrer and reflux condenser, was added Et$_3$N (0.14 mL, 1.00 mmol) in a single portion. The suspension was heated at reflux for 24 hours. The solution was concentrated under reduced pressure and the residue was poured onto ice (100 g). The mixture was partitioned between CH$_2$Cl$_2$ and H$_2$O. The organic portion was dried (MgSO$_4$) and evaporated to dryness under reduced pressure. The residue was dissolved in anhydrous CH$_2$Cl$_2$ (2.0 mL) followed by the addition of Et$_3$N (0.17 mL, 1.20 mmol), and Acetyl chloride (92 mg, 1.20 mmol). The solution was then stirred at ambient temperatues for 1 hour. The solution was concentrated under reduced pressure. The residue was dissolved in anhydrous DMF (0.50 mL) followed by the addition of 1,1'-carbonyldiimidazole (11 mg, 0.07 mmol). The solution was heated at 115° C. for 1 hour. The solution was purified by HPLC (10% to 99% CH$_3$CN) to obtain 30 as a trifluoroacetic acid salt (19 mg, 0.05 mmol, 12% yield) as a white solid. M+1 (obs)=282.2; R$_t$=3.02.

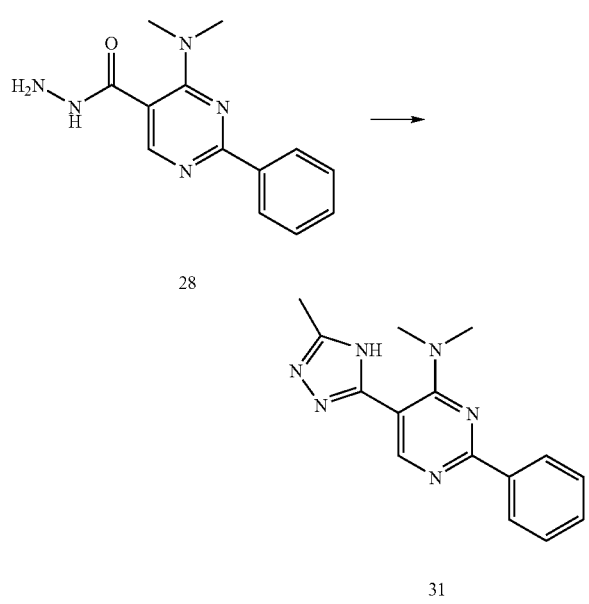

28

31

To a stirring solution of acetamidine hydrochloride (44 mg, 0.47 mmol) and anhydrous EtOH (10 mL) in a 50 mL three-necked round-bottomed flask equipped with a magnetic stirrer, was added sodium methoxide (0.94 mL, 0.047 mmol, 0.5 M in MeOH) in a single portion. The suspension was stirred at ambient temperature for 30 minutes. The mixture was filtered and to the filtrate was added 28 (80 mg, 0.31 mmol). The solution was stirred at ambient temperature for 24 hours. The mixture was partitioned between $CH_2Cl_2$ and $H_2O$. The organic portion was dried ($MgSO_4$) and evaporated to dryness under reduced pressure. The residue was dissolved in a solution of xylenes/octanol (2.0 mL, 20/1). The solution was then heated at reflux for 17 hours with the incorporation of a Dean-Stark apparatus for removal of $H_2O$. The solution was concentrated under reduced pressure and purified by HPLC (10% to 99% $CH_3CN$) to obtain 31 as a trifluoroacetic acid salt (79 mg, 0.20 mmol, 43% yield) as a white solid. M+1 (obs)=282.1; $R_t$=3.01.

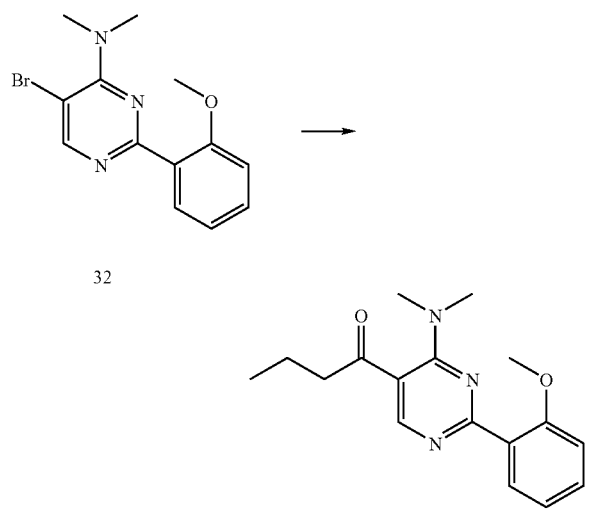

32

33

To a stirring solution of 32 (50.0 mg, 0.16 mmol) and toluene (1.0 mL) in a 20 mL two-necked round-bottomed flask equipped with a magnetic stirrer was added n-butyl-lithium (0.10 mL, 0.16 mmol, 1.60 M in hexane) dropwise at −78 °C. over a period of 2 minutes. The mixture was stirred at −78 °C. for 5 minutes followed by the dropwise addition of butyraldehyde (0.02 mL, 0.24 mmol) over a 2 minute period. The mixture was allowed to warm to room temperature over a period of 20 minutes. The resulting solution was then portioned between saturated aqueous $NH_4Cl$ and EtOAc. The organic portion dried ($MgSO_4$) and evaporated to dryness under reduced pressure. The obtained oil was dissolved in $CH_2Cl_2$ (5.0 mL) followed by the addition of manganese(IV) oxide (139 mg, 1.6 mmol). The mixture was stirred at ambient temperature for 17 hours. The mixture was filtered through a bed of Celite® and the filtrate was concentrated under reduced pressure. The residue was purified by silica gel chromatography using (10% EtOAc, 90% Hexane) to obtain 33 (15 mg, 0.05 mmol, 31% yield) as a clear oil. M+1 (obs)=300.3; $R_t$=2.55.

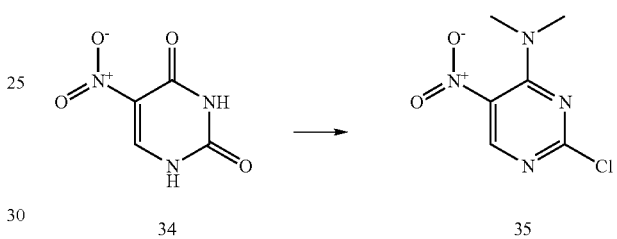

34          35

A stirring solution of 34 (10.0 g, 63.6 mmol), phosphorus oxychloride (25.0 mL), and N,N-dimethylaniline(17.0 g, 140 mmol) in a 200 mL three-necked round-bottomed flask equipped with a magnetic stirrer was heated at 80° C. for a period of 20 minutes. The solution was concentrated under reduced pressure. The residue was residue was poured into ice-water (300 g) and the mixture was basified with saturated aqueous $NaHCO_3$ solution. The mixture was partitioned between $CH_2Cl_2$ and water. The organic portion was dried ($MgSO_4$) and cooled to −78° C. To this solution was added Et3N (8.70 mL, 63.0 mmol) followed by the dropwise addition of dimethylamine (31.8 mL, 63.6 mmol, 2.0 M in THF) at −78° C. over a period of 10 minutes. The mixture was concentrated under reduced pressure. The residue was purified by silica gel chromatography using (30% EtOAc, 70% Hexane) to obtain 35 (3.9 g, 19.2 mmol, 30% yield) as a yellow solid. $^1$H NMR ($CDCl_3$) δ3.01 (s, 6H), 8.62(s, 1H).

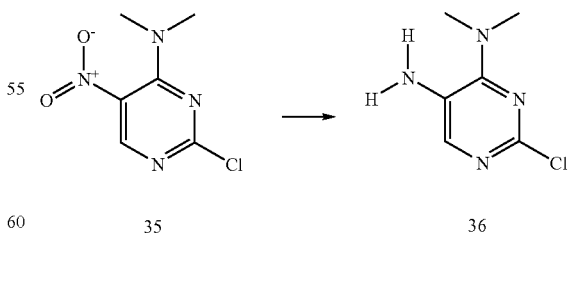

35          36

To a stirring solution of 35 (500 mg, 2.0 mmol) and acetic acid (3.0 mL) in a 50 mL single-necked round-bottomed flask equipped with a magnetic stirrer was added zinc dust (810 mg, 1.2 mmol) portionwise over a period of 5 minutes. The mixture was stirred at ambient temperature for 1 hour. The mixture was poured into a solution of saturated aqueous NaHCO₃ (100 mL). The mixture was filtered and partitioned between CH₂Cl₂ and water. The organic portion was dried (MgSO₄) and concentrated under reduced pressure. The residue was purified by silica gel chromatography using (30% EtOAc, 70% Hexane) to obtain 36 (50 mg, 0.29 mmol, 15% yield) as a tan solid. M+1 (obs)=173.2; $R_t$=2.96.

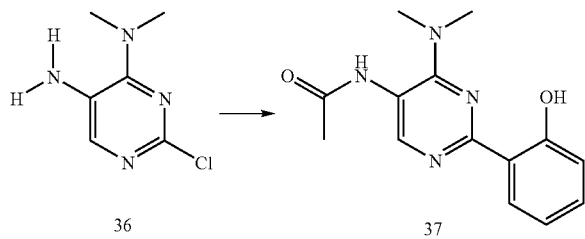

To a stirring solution of 36 (50.0 mg, 0.29 mmol), Et₃N (59.0 mg, 0.58 mmol), and anhydrous CH₂Cl₂ (10.0 mL) in a 50 mL single-necked reaction vessel equipped with a magnetic stirrer was added acetyl chloride (34.0 mg, 0.43 mmol) in a single portion. The mixture was stirred at room temperature for 20 minutes. The solution concentrated under reduced pressure and the residue was purified via silica gel chromatography using (3% MeOH, 97% CH₂Cl₂) to obtain the amide intermediate. The amide intermediate was added to a microwave vessel followed by the addition of CH₃CN (0.50 mL), 2-(4,4,55-tetramethyl-[1,3,2]dioxaborolan-2-yl)-phenol (83 mg, 0.38 mmol) Pd(PPh₃)₄ (30.0 mg, 0.03 mmol), and sodium carbonate (0.50 mL, 0.40 M in H₂O). The mixture was heated via microwave irradiation at 170° C. for 5 minutes. The mixture was filtered and the filtrate purified by HPLC (10% to 99% CH₃CN) to obtain 37 as a trifluoroacetic acid salt (26 mg, 0.07 mmol, 23% yield) as a white solid. M+1 (obs)=273.2; $R_t$=1.77.

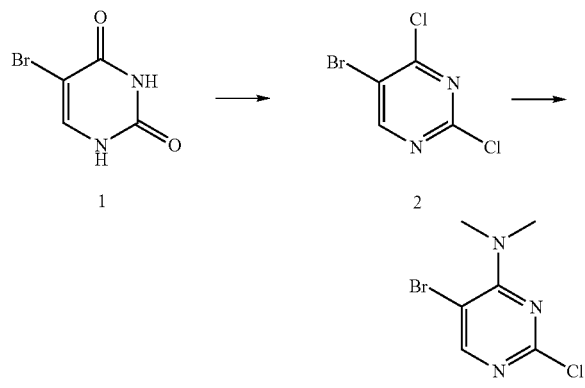

A solution of 5-bromouracil 1 (6.00 g, 31.4 mmol), N,N-dimethylaniline (12.0 mL, 94.7 mmol) in phosphoryl chloride (18 mL) was heated to 120° C. for 2 h. After cooling to RT, the reaction mixture was concentrated in vacuo. The residue was dissolved in CH₂Cl₂ (100 mL), and the pH was adjusted to pH 8-9 by careful addition of a saturated aqueous NaHCO₃ solution. The phases were separated, and the aqueous phase was extracted with CH₂Cl₂ (2×100 mL). The combined organic extracts were dried over MgSO₄ and concentrated in vacuo to give compound 2 which was used without further purification in the next reaction step: To a solution of compound 2 (ca. 31 mmol) in THF (100 mL) at −78° C. was slowly added a solution of dimethylamine in THF (2.0 M, 13.8 mL, 27.6 mmol) over 15 Min. The cooling bath was removed and stirring was continued for 2 h at RT. The solvent was removed in vacuo. Chromatography over silica (EtOAc in hexanes, 0-15%) afforded compound 3 (2.7 g, 36%) as a yellow solid. LC/MS (10-99%) m/z: 238, retention time: 3.19 min. ¹H-NMR (400 MHz, DMSO): δ 8.29 (s, 1H), 3.20 (s, 6H).

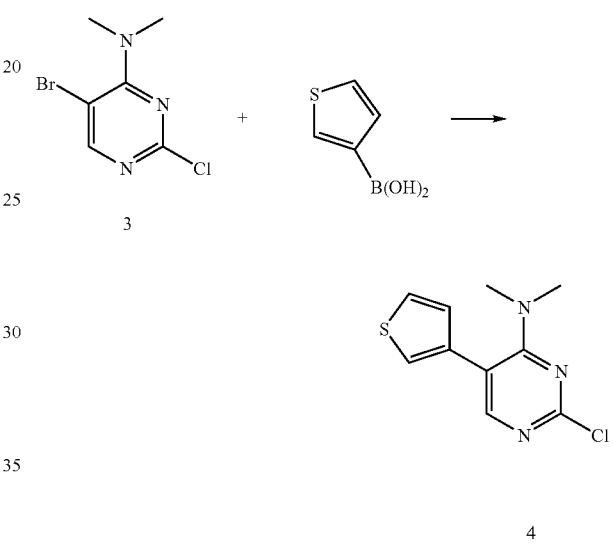

A mixture of compound 3 (237 mg, 1.00 mmol), 3-thiophene boronic acid (128 mg, 1.00 mmol), Pd(PPh₃)₄ (58 mg, 0.05 mmol, 5 mol %) and aqueous Na₂CO₃ (0.4 M, 5 mL, 2.00 mmol) in acetonitrile (5 mL) was heated to reflux for 75 Min. After cooling to RT, CH₂Cl₂ (10 mL) was added and the phases were separated. The aqueous phase was extracted with CH₂Cl₂ (2×10 mL), and the combined organic extracts were dried over MgSO₄ and concentrated in vacuo. Chromatography over silica (EtOAc in hexanes, 0-20%) afforded compound 4 (132 mg, 55%) as a yellow oil. LC/MS (10-99%) m/z: 241, retention time: 3.61 min. ¹H-NMR (400 MHz, DMSO): δ 7.98 (s, 1H), 7.65 (m, 1H), 7.57 (m, 1H), 7.17 (m, 1H), 2.86 (s, 6H).

-continued

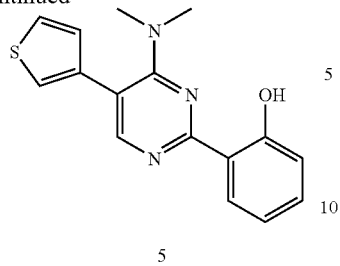

5

A mixture of compound 4 (36 mg, 0.15 mmol), 2-(4,4,5,5)-tetramethyl-1,3,2-dioxaborolan-2-yl)phenol (32 μL, 0.15 mmol), Pd(PPh$_3$)$_4$ (17 mg, 0.015 mmol, 10 mol %) and aqueous Na$_2$CO$_3$ (0.4 M, 0.75 mL, 0.30 mmol) in DME (0.75 mL) was heated by mirowave irradiation to 180° C. for 600 s. The reaction mixture was filtered and purified by preparative HPLC to give compound 5 as a white solid (TFA salt). LC/MS (10-99%) m/z: 298, retention time: 2.89 min.

The characterizaton data for compounds of general formula I prepared by the above methods or methods similar to those above is depicted in Table 3 below.

TABLE 3

| Cmpd No. | LC/MS (m/z) Obs. [M + H]$^+$ | LCMS RT Min |
| --- | --- | --- |
| 1 | 242.1 | 2.95 |
| 2 | 274.2 | 2.76 |
| 3 | 280.20 | 1.08 |
| 4 | 316.00 | 3.14 |
| 5 | 314.00 | 3.27 |
| 6 | 273.10 | 2.76 |
| 7 | 358.00, | 3.27, |
|   | 358.00 | 3.39 |
| 8 | 326.30 | 3.33 |
| 9 | 300.20 | 3.27 |
| 10 | 350.20 | 3.83 |
| 11 | 325.20 | 3.18 |
| 12 | 427.00 | 3.11 |
| 13 | 299.4 | 2.31 |
| 14 | 332.2 | 3.57 |
| 15 | 328.30 | 2.52 |
| 16 | 314.00 | 3.78 |
| 17 | 296.2 | 3.97 |
| 18 | 287.20 | 1.69 |
| 19 | 298.2 | 3.10 |
| 20 | 342.20 | 3.42 |
| 21 | 262.00 | 3.55 |
| 22 | 308.00, | 3.23, |
|   | 308.30 | 3.09 |
| 23 | 368.20 | 3.29 |
| 24 | 320.00 | 2.87 |
| 25 | 356.20 | 3.07 |
| 26 | 287.00 | 2.58 |
| 27 | 281.20 | 2.13 |
| 28 | 353.00 | 4.91 |
| 29 | 288.2 | 3.21 |
| 30 | 378.3 | 4.12 |
| 31 | 271.18 | 3.06 |
| 32 | 320.10 | 3.11 |
| 33 | 340.30 | 4.19 |
| 34 | 304.10 | 3.50 |
| 35 | 326.4 | 1.74 |
| 36 | 324.00 | 4.65 |
| 37 | 288.00 | 3.51 |
| 38 | 228.2 | 3.42 |
| 39 | 306.00 | 4.48 |
| 40 | 328.00 | 4.31 |
| 41 | 340.20 | 3.60 |
| 42 | 300.4 | 3.08 |
| 43 | 313.20, | 3.93, |

TABLE 3-continued

| Cmpd No. | LC/MS (m/z) Obs. [M + H]$^+$ | LCMS RT Min |
| --- | --- | --- |
|  | 327.40 | 4.07 |
| 44 | 340.20 | 3.60 |
| 45 | 339.00 | 4.91 |
| 46 | 299.30 | 3.76 |
| 47 | 375.27 | 4.34 |
| 48 | 314.10 | 3.36 |
| 49 | 326.20 | 2.66 |
| 50 | 388.00 | 3.66 |
| 51 | 357.20 | 2.19 |
| 52 | 328.2 | 3.58 |
| 53 | 314.00 | 2.40 |
| 54 | 314.10 | 2.67 |
| 55 | 343.20 | 2.12 |
| 56 | 405.4 | 2.96 |
| 57 | 300.00 | 3.69 |
| 58 | 306.10 | 3.88 |
| 59 | 258.0 | 3.22 |
| 60 | 328.20 | 3.05 |
| 61 | 410.29 | 3.84 |
| 62 | 332.00 | 4.75 |
| 63 | 272.2 | 2.85 |
| 64 | 296.00 | 3.75 |
| 65 | 360.2 | 4.11 |
| 66 | 292.00 | 2.36 |
| 67 | 271.4 | 2.00 |
| 68 | 300.30 | 3.10 |
| 69 | 300.20 | 3.37 |
| 70 | 364.00 | 3.11 |
| 71 | 327.2 | 2.60 |
| 72 | 272.20 | 2.41 |
| 73 | 328.20 | 1.89 |
| 74 | 344.00 | 2.47 |
| 75 | 329.00 | 3.55 |
| 76 | 330.00 | 2.94 |
| 77 | 342.00 | 3.36 |
| 78 | 400.00 | 3.41 |
| 79 | 284.00 | 2.88 |
| 80 | 312.20 | 3.49 |
| 81 | 286.10, | 3.49, |
|  | 286.10, | 3.16, |
|  | 286.10 | 2.86, |
|  |  | 3.25 |
| 82 | 334.20 | 2.56 |
| 83 | 326.2 | 3.55 |
| 84 | 312.00 | 2.45 |
| 85 | 290.30 | 3.49 |
| 86 | 311.21 | 3.21 |
| 87 | 326.2 | 3.82 |
| 88 | 346.2 | 3.94 |
| 89 | 259.20 | 3.37 |
| 90 | 364.00 | 3.80 |
| 91 | 390.2 | 4.04 |
| 92 | 314.00 | 3.72 |
| 93 | 333.00 | 3.66 |
| 94 | 308.20 | 3.46 |
| 95 | 340.00 | 2.79 |
| 96 | 344.00 | 3.65 |
| 97 | 313.20 | 3.79 |
| 98 | 314.00 | 3.00 |
| 99 | 286.10 | 2.81 |
| 100 | 273.30 | 3.50 |
| 101 | 302.00 | 3.76 |
| 102 | 294.00 | 4.80 |
| 103 | 312.2 | 3.62 |
| 104 | 379.00 | 5.09 |
| 105 | 309.20 | 2.82 |
| 106 | 342.2 | 2.84 |
| 107 | 364.2 | 3.19 |
| 108 | 335.20 | 3.53 |
| 109 | 346.00 | 2.67 |
| 110 | 244.4 | 2.05 |
| 111 | 278.00 | 4.06 |
| 112 | 408.30 | 5.41 |
| 113 | 317.00 | 3.28 |
| 114 | 334.23 | 3.39 |
| 115 | 339.80 | 3.57 |

TABLE 3-continued

| Cmpd No. | LC/MS (m/z) Obs. [M + H]⁺ | LCMS RT Min |
|---|---|---|
| 116 | 326.00 | 3.56 |
| 117 | 351.00 | 3.06 |
| 118 | 294.40 | 1.77 |
| 119 | 288.00 | 3.80 |
| 120 | 336.0 | 3.87 |
| 121 | 336.20 | 3.25 |
| 122 | 290.00 | 3.00 |
| 123 | 376.26 | 3.80 |
| 124 | 324.20 | 1.17 |
| 125 | 339.2 | 2.80 |
| 126 | 297.4 | 2.23 |
| 127 | 378.00 | 2.99 |
| 128 | 278.0 | 3.09 |
| 129 | 330.20 | 2.90 |
| 130 | 261.00 | 4.28 |
| 131 | 301.40 | 3.77 |
| 132 | 342.00 | 2.95 |
| 133 | 318.00 | 3.41 |
| 134 | 334.2 | 3.46 |
| 135 | 301.40 | 3.86 |
| 136 | 316.00 | 3.04 |
| 137 | 282.2 | 2.66 |
| 138 | 314.10 | 3.15 |
| 139 | 288.00 | 3.51 |
| 140 | 338.00 | 3.12 |
| 141 | 285.19 | 3.00 |
| 142 | 297.20 | 3.71 |
| 143 | 286.1 | 3.39 |
| 144 | 300.40 | 3.09 |
| 145 | 359.80 | 2.79 |
| 146 | 300.30 | 2.55 |
| 147 | 328.00 | 3.75 |
| 148 | 300.4 | 3.08 |
| 149 | 314.2 | 3.26 |
| 150 | 342.00 | 3.52 |
| 151 | 306.2 | 3.36 |
| 152 | 298.20 | 2.96 |
| 153 | 304.0 | 3.28 |
| 154 | 325.22 | 3.40 |
| 155 | 244.4 | 3.11 |
| 156 | 270.2 | 3.07 |
| 157 | 299.30 | 3.35 |
| 158 | 387.28 | 4.49 |
| 159 | 300.20 | 3.45 |
| 160 | 358.00 | 2.60 |
| 161 | 295.00 | 3.50 |
| 162 | 364.00 | 3.10 |
| 163 | 312.0 | 3.38 |
| 164 | 295.20 | 3.59 |
| 165 | 274.00 | 3.08 |
| 166 | 354.00 | 3.42 |
| 167 | 286.2 | 2.87 |
| 168 | 318.00 | 4.58 |
| 169 | 443.10 | 3.66 |
| 170 | 302.2 | 2.56 |
| 171 | 262.00, 262.00 | 3.19, 2.54 |
| 172 | 347.24 | 3.84 |
| 173 | 332.20 | 2.40 |
| 174 | 300.40 | 3.12 |
| 175 | 299.30 | 3.66 |
| 176 | 361.00 | 1.94 |
| 177 | 290.00 | 3.96 |
| 178 | 300.4 | 3.28 |
| 179 | 309.20 | 2.76 |
| 180 | 314.10 | 3.23 |
| 181 | 302.2 | 3.34 |
| 182 | 380.00 | 3.31 |
| 183 | 259.20 | 3.57 |
| 184 | 273.30 | 3.39 |
| 185 | 264.00 | 4.28 |
| 186 | 348.00 | 3.27 |
| 187 | 311.00 | 4.48 |
| 188 | 302.00 | 4.01 |
| 189 | 278.0 | 3.79 |
| 190 | 374.26 | 3.70 |
| 191 | 265.00 | 2.81 |
| 192 | 348.00 | 3.99 |
| 193 | 301.40 | 1.77 |
| 194 | 341.20 | 2.06 |
| 195 | 376.2 | 3.67 |
| 196 | 361.2 | 2.93 |
| 197 | 328.20 | 3.28 |
| 198 | 300.20 | 3.20 |
| 199 | 354.0 | 3.67 |
| 200 | 328.00 | 3.58 |
| 201 | 348.24 | 3.44 |
| 202 | 350.2 | 3.44 |
| 203 | 287.00 | 2.41 |
| 204 | 345.00 | 2.09 |
| 205 | 328.4 | 3.26 |
| 206 | 351.00 | 3.06 |
| 207 | 386.00 | 3.53 |
| 208 | 306.2 | 2.84 |
| 209 | 328.30 | 2.48 |
| 210 | 262.00 | 2.64 |
| 211 | 258.2 | 2.44 |
| 212 | 333.2 | 2.59 |
| 213 | 316.20 | 3.16 |
| 214 | 287.8 | 2.99 |
| 215 | 259.00 | 2.83 |
| 216 | 302.00 | 2.78 |
| 217 | 302.00 | 3.95 |
| 218 | 332.00 | 3.20 |
| 219 | 322.20 | 2.65 |
| 220 | 355.80 | 4.22 |
| 221 | 345.2 | 3.31 |
| 222 | 288.00 | 3.03 |
| 223 | 328.00 | 4.03 |
| 224 | 335.40 | 4.26 |
| 225 | 373.00 | 2.10 |
| 226 | 304.00 | 4.29 |
| 227 | 260.0 | 3.94 |
| 228 | 290.30 | 3.21 |
| 229 | 347.24 | 4.05 |
| 230 | 243.4 | 1.88 |
| 231 | 373.27 | 4.17 |
| 232 | 311.2 | 2.39 |
| 233 | 316.00 | 4.24 |
| 234 | 272.20 | 2.53 |
| 235 | 355.80 | 4.04 |
| 236 | 409.30 | 5.06 |
| 237 | 356.00 | 3.97 |
| 238 | 378.2 | 3.90 |
| 239 | 314.00 | 2.58 |
| 240 | 301.20 | 3.13 |
| 241 | 313.30, 327.30 | 3.50, 3.35 |
| 242 | 328.00 | 2.85 |
| 243 | 404.2 | 4.21 |
| 244 | 388.27 | 3.81 |
| 245 | 248.00 | 3.59 |
| 246 | 279.20 | 2.99 |
| 247 | 333.23 | 4.35 |
| 248 | 292.2 | 3.72 |
| 249 | 282.00 | 3.01 |
| 250 | 293.00 | 1.99 |
| 251 | 295.00 | 0.80 |
| 252 | 323.20 | 2.20 |
| 253 | 273.20 | 1.77 |
| 254 | 225.1 | 3.83 |
| 255 | 289.4 | 2.41 |
| 256 | 282.20 | 3.02 |
| 257 | 282.10 | 3.01 |
| 258 | 297.20 | 2.83 |
| 259 | 296.20 | 3.23 |
| 260 | 426.20 | 4.01 |
| 261 | 253.2 | 4.09 |
| 262 | 274.4 | 3.90 |
| 263 | 283.30 | 3.79 |
| 264 | 283.00 | 1.99 |
| 265 | 362.00 | 2.46 |

TABLE 3-continued

| Cmpd No. | LC/MS (m/z) Obs. $[M + H]^+$ | LCMS RT Min |
|---|---|---|
| 266 | 290.00 | 3.41 |
| 267 | 275.80 | 3.07 |
| 268 | 306.2 | 3.11 |
| 269 | 259.80 | 2.46 |
| 270 | 293.00 | 2.13 |
| 271 | 262.0 | 3.37 |
| 272 | 317.9 | 4.24 |
| 273 | 384.10 | 3.43 |
| 274 | 251.0 | 4.07 |
| 275 | 282.00 | 2.69 |
| 276 | 296.40 | 3.18 |
| 277 | 265.2 | 4.23 |
| 278 | 322.20 | 3.63 |
| 279 | 264.0 | 2.34 |
| 280 | 295.00 | 0.90 |
| 281 | 282.20 | 2.96 |
| 282 | 304.2 | 2.96 |
| 283 | 260.2 | 2.96 |
| 284 | 284.00 | 2.44 |
| 285 | 308.20 | 3.25 |
| 286 | 296.4 | 3.46 |
| 287 | 231.20 | 1.85 |
| 288 | 278.0 | 2.83 |
| 289 | 234.2 | 2.83 |
| 290 | 300.00 | 2.55 |
| 291 | 310.20 | 3.40 |
| 292 | 374.00 | 2.67 |
| 293 | 220.2 | 2.25 |
| 294 | 294.00 | 3.63 |
| 295 | 306.20 | 2.88 |
| 296 | 279.0 | 4.63 |
| 297 | 267.00 | 2.83 |
| 298 | 285.00 | 2.12 |
| 299 | 281.00 | 2.22 |
| 300 | 272.0 | 2.97 |
| 301 | 244.2 | 3.36 |
| 302 | 258.0 | 2.81 |
| 303 | 306.2 | 3.34 |
| 304 | 264.20 | 2.28 |

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

B) VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 µL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells are loaded with 80 µL of the CC2-DMPE solution. Plates are incubated in the dark for 30 minutes at room temperature.
4) While the cells are being stained with coumarin, a 15 µL oxonol solution in BS#2 is prepared. In addition to DiSBAC$_2$(3), this solution should contain 0.75 mM ABSC1 and 30 µL veratridine (prepared from 10 mM EtOH stock, Sigma #V-5754).
5) After 30 minutes, CC2-DMPE is removed and the cells are washed twice with 225 µL of BS#2. As before, the residual volume should be 40 µL.
6) Upon removing the bath, the cells are loaded with 80 µL of the DiSBAC$_2$(3) solution, after which test compound, dissolved in DMSO, is added to achieve the desired test concentration to each well from the drug addition plate and mixed thoroughly. The volume in the well should be roughly 121 µL. The cells are then incubated for 20-30 minutes.
7) Once the incubation is complete, the cells are ready to be assayed on VIPR® with a sodium addback protocol. 120 µL of Bath solution #1 is added to stimulate the NaV dependent depolarization. 200 µL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460 \text{ nm}} - \text{background}_{460 \text{ nm}})}{(\text{intensity}_{580 \text{ nm}} - \text{background}_{580 \text{ nm}})}$$

The data is further reduced by calculating the initial ($R_i$) and final ($R_f$) ratios. These are the average ratio values during part or all of the pre-stimulation period, and during sample points during the stimulation period. The response to the stimulus $R_r = R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound
Solutions [mM]
Bath Solution #1: NaCl 160, KCl 4.5, CaCl$_2$ 2, MgCl$_2$ 1, HEPES 10, pH 7.4 with NaOH
Bath Solution #2 TMA-Cl 160, CaCl$_2$ 0.1, MgCl$_2$ 1, HEPES 10, pH 7.4 with KOH (final K concentration~5 mM)
CC2-DMPE: prepared as a 5 mM stock solution in DMSO and stored at −20° C.
DiSBAC$_2$(3): prepared as a 12 mM stock in DMSO and stored at −20° C.
ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:
100 mg/mL Pluronic F-127 (Sigma #P2443), in dry DMSO
10 mM DiSBAC$_2$(3) (Aurora #00-100-010) in dry DMSO
10 mM CC2-DMPE (Aurora #00-100-008) in dry DMSO
200 mM ABSC1 in H$_2$O
Hank's Balanced Salt Solution (Hyclone #SH30268.02) supplemented with 10 mM HEPES (Gibco #15630-080)

Loading Protocol:

2×CC2-DMPE=20 μM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 μL of 2×CC2-DMPE is to wells containing washed cells, resulting in a 10 μM final staining concentration. The cells are stained for 30 minutes in the dark at RT.

2×DISBAC$_2$(3) with ABSC1=6 μM DISBAC$_2$(3) and 1 mM ABSC1: The required amount of 10 mM DISBAC$_2$(3) is added to a 50 ml conical tube and mixed with 1 μL 10% pluronic for each mL of solution to be made and vortexed together. Then HBSS/HEPES is added to make up 2× solution. Finally, the ABSC1 is added.

The 2×DiSBAC$_2$(3) solution can be used to solvate compound plates. Note that compound plates are made at 2× drug concentration. Wash stained plate again, leaving residual volume of 50 μL. Add 50 μL/well of the 2×DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents
Assay Buffer #1
140 mM NaCl, 4.5 mM KCl, 2 mM CaCl$_2$, 1 mM MgCl$_2$, 10 mM HEPES, 10 mM glucose, pH 7.40, 330 mOsm
Pluronic stock (1000×): 100 mg/mL pluronic 127 in dry DMSO
Oxonol stock (3333×): 10 mM DiSBAC$_2$(3) in dry DMSO
Coumarin stock (1000×): 10 mM CC2-DMPE in dry DMSO
ABSC1 stock (400×): 200 mM ABSC1 in water Assay Protocol
1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\ nm} - \text{background}_{460\ nm})}{(\text{intensity}_{580\ nm} - \text{background}_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), CdCl2 (0.4), NiCl2 (0.1), TTX ($0.25 \times 10^{-3}$).

Current-Clamp Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM): 150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

Compounds of the invention as shown in Table 2 were found modulate voltage-gated sodium channels.

Assays for Detecting and Measuring CaV Inhibition Properties of Compounds

A) Optical Methods for Assaying CaV Inhibition Properties of Compounds:

Compounds of the invention are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See. Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR®) (See Gonzalez, J. E., K. Oades, et al. (1999) "Cell-based assays and instrumentation for screening ion-channel targets" Drug Discov Today 4(9): 431-439).

VIPR® Optical Membrane Potential Assay Method with Electrical Stimulation

The following is an example of how CaV2.2 inhibition activity is measured using the optical membrane potential method. Other subtypes are performed in an analogous mode in a cell line expressing the CaV of interest.

HEK293 cells stably expressing CaV2.2 are plated into 96-well microtiter plates. After an appropriate incubation period, the cells are stained with the voltage sensitive dyes CC2-DMPE/DiSBAC2(3) as follows.

Reagents:
100 mg/mL Pluronic F-127 (Sigma #P2443), in dry DMSO
10 mM $DiSBAC_6(3)$ (Aurora #00-100-010) in dry DMSO
10 mM CC2-DMPE (Aurora #00-100-008) in dry DMSO
200 mM Acid Yellow 17 (Aurora #VABSC) in $H_2O$
370 mM Barium Chloride (Sigma Cat# B6394) in $H_2O$ Bath X
160 mM NaCl (Sigma Cat# S-9888)
4.5 mM KCl (Sigma Cat# P-5405)
1 mM MgCl2 (Fluka Cat# 63064)
10 mM HEPES (Sigma Cat# H-4034)
pH 7.4 using NaOH Loading Rotocol:

2×CC2-DMPE=20 μM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 μL of 2×CC2-DMPE is added to wells containing washed cells, resulting in a 10 μM final staining concentration. The cells are stained for 30 minutes in the dark at RT.

2×CC2DMPE & $DISBAC_6(3)$=8 μM CC2DMPE & 2.5 μM $DISBAC_6(3)$: Vortex together both dyes with an equivalent volume of 10% pluronic (in DMSO). Vortex in required amount of Bath X with beta-cyclodextrin. Each 96well cell plate will require 5 ml of 2×CC2DMPE. Wash plate with ELx405 with Bath X, leaving a residual volume of 50 μL/well. Add 50 μL of 2×CC2DMPE & $DISBAC_6(3)$ to each well. Stain for 30 minutes in the dark at RT.

1.5×AY17=750 μM AY17 with 15 mM $BaCl_2$: Add Acid Yellow 17 to vessel containing Bath X. Mix well. Allow solution to sit for 10 minutes. Slowly mix in 370 mM $BaCl_2$. This solution can be used to solvate compound plates. Note that compound plates are made at 1.5× drug concentration and not the usual 2×. Wash CC2 stained plate, again, leaving residual volume of 50 μL. Add 100 uL/well of the AY17 solution. Stain for 15 minutes in the dark at RT. Run plate on the optical reader.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Assay Protocol

Insert or use electrodes into each well to be assayed.

Use the current-controlled amplifier to deliver stimulation wave pulses for 3-5 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\ nm} - \text{background}_{460\ nm})}{(\text{intensity}_{580\ nm} - \text{background}_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as mibefradil, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for CaV Activity and Inhbition of Test Compounds

Patch clamp electrophysiology was used to assess the efficacy of calcium channel blockers expressed in HEK293 cells. HEK293 cells expressing CaV2.2 have been visually identified and probed with fine tip glass electrodes connected to an amplifier (Axon Instruments). The "voltage clamp" mode has been used to assess the compound's IC50 holding the cells at −100 mV. The results of these experiments have contributed to the definition of the efficacy profile of the compounds.

Voltage-Clamp Assay in HEK293 Cells Expressing CaV2.2

CaV2.2 calcium currents were recorded from HEK293 cells using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording.

Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +20 mV for 50 ms at frequencies of 0.1, 1, 5, 10, 15, and 20 Hz. Blocking effects were allowed to plateau before proceeding to the next test concentration.

Solutions

Intracellular solution (in mM): Cs—F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), BaCl$_2$ (10), KCl (5.33), KH$_2$PO$_4$ (0.44), MgCl$_2$ (0.5), MgSO$_4$ (0.41), NaHCO$_3$ (4), Na$_2$HPO$_4$ (0.3), glucose (5.6), HEPES (10).

Following these procedures, representative compounds of the present invention were found to possess desired N-type calcium channel modulation activity and selectivity.

The invention claimed is:

1. A compound having formula IA:

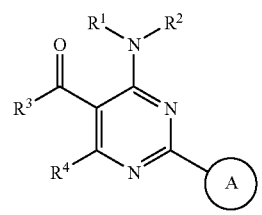

IA or a pharmaceutically acceptable salt thereof, wherein:
R$^1$ and R$^2$ are each hydrogen; or
both R$^1$ and R$^2$ independently selected from methyl, ethyl, cyclopropyl, n-propyl, propenyl, cyclobutyl, (CO)OCH$_2$CH$_3$, (CH)$_2$OCH$_3$, CH$_2$(CO)OCH$_2$CH$_3$, CH$_2$(CO)OCH$_3$, CH(CH$_3$)CH$_2$CH$_3$, or t-butyl, or n-butyl; or
R$^1$ and R$^2$, taken together with the nitrogen atom to which they are bound, form ring bb, dd, ee, ff, or gg;

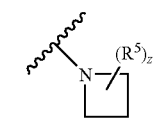

bb

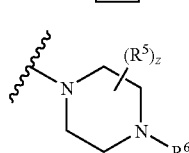

dd

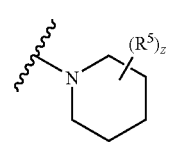

ee

-continued

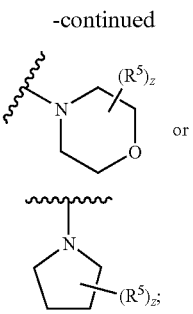

ff gg wherein z is 0-4;
ring A is a-phenyl ring-optionally substituted at one or more carbon atoms with 0-5 occurrences of —$R^7$;
$R^3$ is selected from —$CF_2H$, —$CF_3$, —$CHCl_2$, —$CHBr_2$, $CH_2CN$, —$CH_2OR'$, —$CH_2SR'$, —$CH_2N(R')_2$, —$N(R')_2$, —$(CH_2)_2N(R')_2$, —$(CH_2)_2OR'$, —$(CH_2)_2SR'$, —$COR'$, —$CON(R')_2$, or —$S(O)_2N(R')_2$ or an optionally substituted group selected from $C_{2-8}$ aliphatic, $C_{6-10}$ aryl, aryl($C_{1-6}$)alkyl, a heteroaryl ring having 5-10 ring atoms, or a heterocyclyl ring having 3-10 ring atoms;
$R^4$ is selected from hydrogen, halogen, CN, $NO_2$, or an optionally substituted group selected from $C_{1-6}$alkyl, aryl, aryl($C_{1-6}$)alkyl, —$N(R')_2$, —$CH_2N(R')_2$, $OR'$, —$CH_2OR'$, $SR'$, —$CH_2SR'$, $COOR'$, —$NRCOR'$, —$(CH_2)_2N(R')_2$, —$(CH_2)_2OR'$, —$(CH_2)_2SR'$, —$COR'$, —$CON(R')_2$, or —$S(O)_2N(R')_2$;
each occurrence of $R^5$ is independently selected from halogen, CN, $NO_2$, or an optionally substituted group selected from $C_{1-6}$alkyl, aryl, aryl($C_{1-6}$)alkyl, —$N(R')_2$, —$CH_2N(R')_2$, $OR'$, —$CH_2OR'$, $SR'$, —$CH_2SR'$, $COOR'$, —$NRCOR'$, —$NRC(O)OR'$, —$(CH_2)_2N(R')_2$, —$(CH_2)_2OR'$, —$(CH_2)_2SR'$, —$COR'$, —$CON(R')_2$, or —$S(O)_2N(R')_2$;
each occurrence of $R^7$ is independently selected from halogen, CN, $NO_2$, or an optionally substituted group selected from $C_{1-6}$alkyl, aryl, aryl($C_{1-6}$)alkyl, —$N(R')_2$, —$CH_2N(R')_2$, $OR'$, —$CH_2OR'$, $SR'$, —$CH_2SR'$, $COOR'$, —$NRCOR'$, —$(CH_2)_2N(R')_2$, —$(CH_2)_2OR'$, —$(CH_2)_2SR'$, —$COR'$, —$CON(R')_2$, or —$S(O)_2N(R')_2$;
wherein each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur; and
$R^6$ is selected from R', —$COR'$, —$CO_2(C_{1-6}$ aliphatic), —$CON(R')_2$, or —$SO_2R'$, provided that
l) when $R^1$ is hydrogen and $R^2$ is hydrogen, ring A is optionally substituted phenyl, $R^3$ is unsubstituted phenyl, then $R^4$ is not SMe, =S, Me, or unsubstituted phenyl;
r) when $R^1$ and $R^2$ taken together form a N-pyrrolidinyl ring, $R^3$ is —$NHCH_2$(4-trifluoromethylphenyl), $R^4$ is H, then ring A is not 3,4-dimethoxyphenyl, or 2-methoxyphenyl; and
s) when $R^1$ and $R^2$ are both hydrogen, then $N(R')_2$ is not $NH_2$;
t) when $R^1$ and $R^2$ are both methyl, then $N(R')_2$ is not NH-tetrazolyl;
u) when $R^1$ is methyl, and $R^2$ is —$(CH_2)_2$—OH, $R^4$ is hydrogen, ring A is unsubstituted phenyl, then $N(R')_2$ is not $NH_2$;
v) when $R^1$ and $R^2$ are both hydrogen, $N(R')_2$ is $NH_2$, NH-(optionally substituted phenyl), N(optionally substituted C1-6 aliphatic)(optionally substituted phenyl), or NH(6,7,8,9-tetrahydro-5H-benzocyclohepten-6-yl) and $R^4$ is hydrogen, then ring A is not 1-imidazolyl 1-piperidyl, unsubstituted phenyl, optionally substituted 2-oxo-imidazolidin-1-yl or 1-[(2-fluorophenyl)methyl]-1H-indazol-3-yl.

2. The compound according to claim 1, wherein $R^1$ and $R^2$ are identical.

3. The compound according to claim 1, wherein $R^6$ is hydrogen, or an optionally substituted group selected from $C_{1-6}$alkyl, aryl, aryl($C_{1-6}$)alkyl, —$N(R')_2$, —$CH_2N(R')_2$, —$CH_2OR'$, —$CH_2SR'$, —$(CH_2)_2N(R')_2$, —$(CH_2)_2OR'$, —$(CH_2)_2SR'$, —$COR'$, —$CON(R')_2$, or —$S(O)_2N(R')_2$.

4. The compound according to claim 3, wherein $R^6$ is independently H, Me, $CF_3$, ethyl, propyl, butyl, pentyl, $CO(C_1-C_4$alkyl), —$CONH_2$, —$COO(C_1-C_4$alkyl), —$CH_2OH$, —$SO_2NH_2$, $SO_2N(CH_3)_2$, or optionally substituted phenyl.

5. The compound according to claim 1, wherein $R^4$ is hydrogen, halogen, CN, $NO_2$, or an optionally substituted group selected from $C_{1-6}$alkyl, aryl, aryl($C_{1-6}$)alkyl, —$N(R')_2$, —$CH_2N(R')_2$, $OR'$, —$CH_2OR'$, $SR'$, —$CH_2SR'$, $COOR'$, —$NRCOR'$, —$(CH_2)_2N(R')_2$, —$(CH_2)_2OR'$, —$(CH_2)_2SR'$, —$COR'$, —$CON(R')_2$, or —$S(O)_2N(R')_2$.

6. The compound according to claim 5, wherein $R^4$ is H, Cl, Br, F, $CF_3$, Me, Et, CN, $NO_2$, —COOH, $NH_2$, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, $SO_2N(CH_3)_2$, piperidinyl, piperazinyl, morpholino, or an optionally substituted group selected from $C_{1-4}$alkoxy, phenyl, phenyloxy, benzyl, or benzyloxy.

7. The compound of claim 1, wherein $R^3$ is —$CF_3$, ethyl, propyl, butyl, pentyl, $CO(C_1-C_4$alkyl), —$CONH_2$, —COO($C_1-C_4$alkyl), —$CH_2OH$, —$SO_2NH_2$, $SO_2N(CH_3)_2$, or optionally substituted phenyl.

8. The compound according to claim 1, wherein ring A is phenyl, and wherein ring A has 0-2 occurrences of —$R^7$.

9. The compound according to claim 8, wherein ring A is unsubstituted phenyl.

10. The compound according to claim 8, wherein each $R^7$ is independently H, Cl, Br, F, $CF_3$, Me, Et, CN, $NO_2$, —COOH, $NH_2$, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, —$SO_2N(CH_3)_2$, piperidinyl, piperazinyl, morpholino, or an optionally substituted group selected from $C_{1-4}$alkoxy, phenyl, phenyloxy, benzyl, or benzyloxy.

11. The compound according to claim 1, wherein $R^1$ and $R^2$ are both methyl, ethyl, or propyl, $R^3$ is ethyl, propyl or butyl, and ring A is phenyl having up to one $R^7$ substituent selected from R', halogen, $NO_2$, or CN.

12. The compound according to claim 1, wherein $R^1$ and $R^2$ are both methyl, ethyl, or propyl, or $R^1$ and $R^2$, taken together form an optionally substituted 1-pyrrolidinyl or 1-piperidinyl, $R^3$ is optionally substituted ethyl, propyl, butyl, or phenyl, and ring A is phenyl having up to one $R^7$ substituent selected from R', halogen, $NO_2$, or CN.

13. The compound according to claim 12, wherein, $R^1$ and $R^2$ both are methyl or ethyl, $R^3$ is ethyl or propyl, $R^4$ is hydrogen, and ring A is a 2-substituted phenyl, wherein said ring A substituent is selected from R', halogen, $NO_2$, or CN.

14. The compound according to claim 1, wherein $R^1$ and $R^2$ include methyl or ethyl, $R^3$ is optionally substituted ethyl, or propyl, ring A is phenyl having up to one $R^7$ substituent selected from R', halogen, $NO_2$, or CN.

15. The compound according to claim 14, wherein $R^1$ and $R^2$ are both methyl or ethyl, $R^3$ is ethyl or propyl, $R^4$ is hydrogen, and ring A is phenyl optionally substituted with halo, or OH.

16. The compound according to claim 1, wherein $R^1$ and $R^2$ are both methyl, ethyl, or propyl; or $R^1$ and $R^2$, taken together form a 1-azetidinyl or 1-pyrrolidinyl ring, $R^3$ is optionally substituted ethyl, propyl, butyl, or phenyl, and ring A is phenyl having up to one $R^7$ substituent selected from R', halogen, $NO_2$, or CN.

17. The compound according to claim 1, wherein $R^1$ and $R^2$ are both methyl or ethyl, $R^3$ is ethyl or propyl, $R^4$ is hydrogen, and ring A is phenyl optionally substituted with halo, or OH.

18. The compound according to claim 1, wherein $R^1$ and $R^2$ are both methyl or ethyl, $R^3$ is propyl, n-butyl, or isobutyl, $R^4$ is hydrogen, and ring A is phenyl having up to two substituents selected from halo, OH, OMe, $OCF_3$, or $C_{1-4}$ aliphatic.

19. The compound according to claim 1, having formula IIIA:

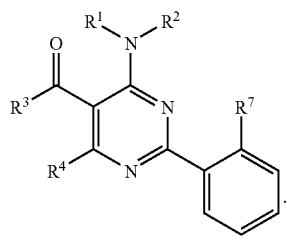

20. The compound according to claim 1 wherein said compound is selected from:

| Cmpd # | Compound |
|---|---|
| 8 | 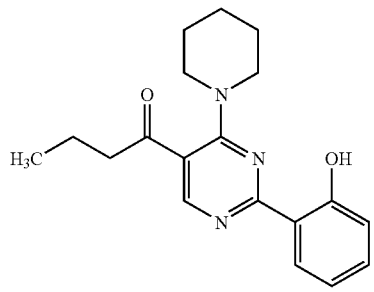 |
| 13 | ![structure] |
| 17 | ![structure] |
| 18 | ![structure] |
| 35 | ![structure] |
| 41 | ![structure] |
| 44 | ![structure] |

-continued

| Cmpd # | Compound |
|---|---|
| 48 | (structure) |
| 53 | (structure) |
| 60 | (structure) |
| 67 | (structure) |
| 68 | (structure) |
| 80 | (structure) |

-continued

| Cmpd # | Compound |
|---|---|
| 81 | (structure) |
| 99 | (structure) |
| 125 | (structure) |
| 126 | (structure) |
| 144 | (structure) |
| 146 | (structure) |

-continued
| Cmpd # | Compound |
|---|---|
| 152 | 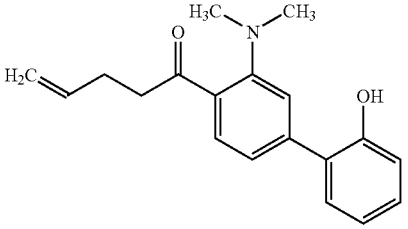 |
| 153 | 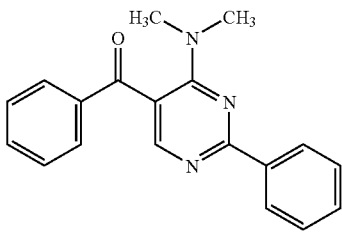 |
| 156 | 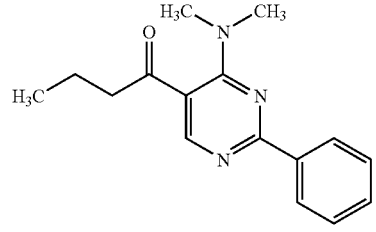 |
| 193 | 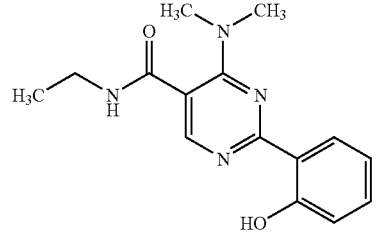 |
| 212 | 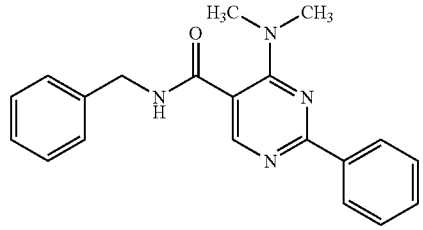 |
-continued
| Cmpd # | Compound |
|---|---|
| 230 | 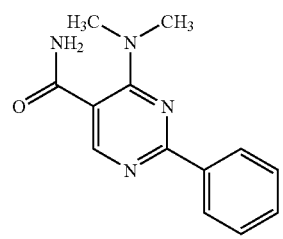 |
| 232 | 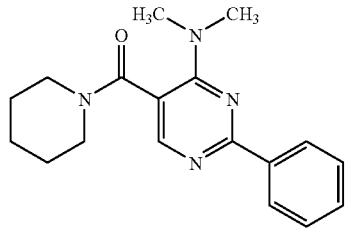 |
| 234 | 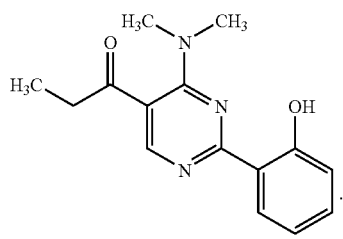 |
21. A composition comprising a compound according to any one of claims 1, 2, 3-6, 8, 10, 11, 12, 13, 14, 15, 16, 17, 18, 19, or 20 and a pharmaceutically acceptable carrier, vehicle, or diluent.
22. The composition according to claim 21 comprising an additional therapeutic agent.
* * * * *